United States Patent [19]

Tanaka et al.

[11] Patent Number: 5,053,548
[45] Date of Patent: Oct. 1, 1991

[54] BIPHENYL DERIVATIVE COMPOSITION FOR NERVE CELL DEGENERATION REPAIRING OR PROTECTIVE AGENT AND PROCESS FOR PREPARING A PHENYL DERIVATIVE CONTAINED IN THE COMPOSITION

[75] Inventors: Tatsuyoshi Tanaka; Yoji Sakurai; Hiroshi Okazaki; Takashi Hasegawa; Yoshiyasu Fukuyama, all of Tokushima, Japan

[73] Assignee: Otsuka Pharmaceutical Co., Ltd., Tokyo, Japan

[21] Appl. No.: 476,913

[22] Filed: Feb. 8, 1990

[30] Foreign Application Priority Data

Feb. 8, 1989 [JP] Japan .................................. 1-28983
Nov. 16, 1989 [JP] Japan .................................. 1-299415

[51] Int. Cl.$^5$ ............................................ C07C 39/21
[52] U.S. Cl. .................................... 568/47; 548/203; 548/537; 548/556; 564/219; 564/337; 568/33; 568/47; 568/331; 568/636; 568/643; 568/660; 568/730
[58] Field of Search ............... 568/730, 643, 660, 636, 568/47, 331, 33; 564/337, 214; 548/537, 556, 203

[56] References Cited

U.S. PATENT DOCUMENTS

| | | | |
|---|---|---|---|
| 3,471,576 | 10/1969 | Klesper et al. | 568/730 |
| 3,481,989 | 12/1969 | Vesely et al. | 568/730 |
| 3,639,636 | 2/1972 | Barnhart | 568/730 |
| 4,115,590 | 9/1978 | Lerner | 568/730 |
| 4,174,447 | 11/1979 | Fields | 568/730 |
| 4,188,274 | 2/1980 | Fields | 568/730 |
| 4,195,154 | 3/1980 | Kaiser et al. | 568/730 |
| 4,599,451 | 7/1986 | Wojtkowski . | |

FOREIGN PATENT DOCUMENTS

| | | | |
|---|---|---|---|
| 19274 | 7/1983 | Australia | 568/730 |
| 012354 | 1/1984 | European Pat. Off. | 568/730 |
| 1645263 | 10/1965 | Fed. Rep. of Germany | 568/730 |
| 122513 | 4/1972 | German Democratic Rep. | 568/730 |
| 4516478 | 11/1970 | Japan | 568/730 |
| 5025537 | 6/1975 | Japan | 568/730 |
| 5054409 | 6/1975 | Japan | 568/730 |
| 5567494 | 5/1980 | Japan | 568/730 |
| 56-9724 | 2/1981 | Japan | 568/730 |
| 135432 | 4/1981 | Japan | 868/730 |
| 133281 | 2/1982 | Japan | 568/730 |
| 193420 | 3/1982 | Japan | 568/730 |
| 578295 | 3/1982 | Japan | 568/730 |
| 59-9528 | 4/1984 | Japan | 568/730 |
| 165338 | 12/1984 | Japan | 568/730 |
| 181044 | 1/1985 | Japan | 568/730 |
| 60-72801 | 8/1985 | Japan | 568/730 |
| 118301 | 7/1986 | Japan | 568/730 |
| 239246 | 5/1988 | Japan | 568/730 |
| 1107208 | 8/1970 | United Kingdom | 568/730 |

*Primary Examiner*—Robert Gerstl
*Attorney, Agent, or Firm*—Sughrue, Mion, Zinn Macpeak & Seas

[57] ABSTRACT

There is disclosed a biphenyl derivative of the formula (B):

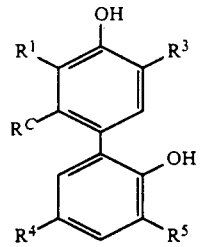

wherein $R^1$, $R^3$, $R^4$, $R^5$ and $R^c$ are as defined or its salt, a composition for nerve cell degeneration repairing or protecting agent containing a phenyl derivative selected from compounds (1) to (4) and (B) as defined, and a process for preparing a phenyl derivative contained in the composition.

16 Claims, 4 Drawing Sheets

BIPHENYL DERIVATIVE COMPOSITION FOR NERVE CELL DEGENERATION REPAIRING OR PROTECTIVE AGENT AND PROCESS FOR PREPARING A PHENYL DERIVATIVE CONTAINED IN THE COMPOSITION

BACKGROUND OF THE INVENTION

This invention relates to a biphenyl derivative, a composition for nerve cell degeneration repairing or protecting agent, and process for preparing a phenyl derivative contained in the composition.

Recently it is indicated that in the senile dementia such as Alzheimer disease, the central cholinergic nervous system has a serious change and that the function deteriorates (Perry, E. K. and Perry, R. H.: "Biochemistry of Dimentia", John Wiley & Sons, p. 135, 1980).

Therefore, a compound having repairability (survival effect and expanding effect of nerve process) and protective action can be efficiently used as a therapeutic or preventive agent for defects of intelligent learning such as senile dementia by Alzheimer disease, Down syndrome, Huntington chorea, amnesia and defects of memory, and sequelae and mental disorders based on the deteriorated function of the central cholinergic nervous system caused by cranio-cerebral injuries, cerebral operation, drug intoxication, circulatory disorders, cerebral metabolic disorders and encephalitis (J. W. Geddes, et al.: Science, 230, 1179–1181, 1985).

Conventionally, as compounds having the nerve cell degeneration repairability as mentioned above, only NGF (nerve growth factor), $GM_1$ (ganglioside) or the like have been known. The NGF is described in the Neuroscience (Hefti, F., et al. 14, 55–68, 1985), the Journal of Neuroscience (Franz Hefti, 6, 2155–2162, 1986), the proceedings of the Natural Academy of Science of the U.S.A. (L. R. Williams, et al., Proc. Natl. Acad. Sci. U.S.A., 83, 9231–9235, 1986) and the Science (L. E. Kromer, 235, 214–216, 1986). The $GM_1$ is described in the Science (Fred J. Roisen, et al., 214, 577–578, 1981), the Brain Res. (M. V. Sofroniew, et al., 398, 393–396, 1986), the Brain Res. (M. Gradkowska, et al., 375, 417–422, 1986).

SUMMARY OF THE INVENTION

This invention relates to a nerve cell degeneration repairing or protecting agent containing as its active ingredient at least one selected from the group consisting of compounds identified by general formulas (1), (2), (3), (4) and (A), which are shown below.

Biphenyl derivative represented by the General formula (1):

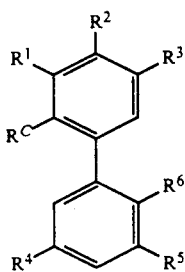
(1)

[where $R^1$ is a hydrogen atom, lower alkyl group, lower alkenyl group, or phenyl group which may have a hydroxyl group, lower alkyl group or lower alkenyl group as subsitituent on its phenyl ring, cycloalkenyl group, halogen atom or lower alkanoyl group. $R^2$ is a hydroxy group, lower alkanoyloxy group, lower alkenyloxy group or alkoxy group which may have lower alkoxy group, tetrahydropyranyloxy group or hydroxyl group as substitutent. $R^3$ is a hydroxyl group, hydrogen atom, lower alkyl group which may have a lower alkoxy group or hydroxy group, lower alkenyl group, cycloalkenyl group, phenyl group or halogen atom, lower alkanoyl group which may have a halogen atom as substituent, or thiazolyl group or group:

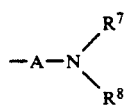

(where A is a lower alkylene group. $R^7$ and $R^8$ are, the same or different, a hydrogen atom, lower alkyl group or lower alkanoyl group. Moreover, $R^7$ and $R^8$ may form saturated or unsaturated heterocyclic ring of five or six members with or without nitrogen atom or oxygen atom together with a nitrogen atom with which they are combined. The heterocyclic ring may have an amide group which may have lower alkyl group as substituent or an oxo group) or group:

(where $R^{7a}$, $R^{7b}$ and $R^{7c}$ are lower alkyl groups, respectively. A is a lower alkylene group). $R^4$ is a hydrogen atom, lower alkyl group which may have a hydroxyl group or lower alkoxy group as substitutent, lower alkoxy group, phenyl group, phenyl-lower alkyl group, phenoxy group, lower alkenyl group, lower alkylthio group, lower alkylsulfinyl group, lower alkylsulfonyl group, halogen atom, lower alkoxy-lower alkyl group or lower alkanoyl group. $R^5$ is a hydrogen atom, hydroxyl group, lower alkyl group, lower alkoxy group, lower alkenyl group, cycloalkenyl group, amino-lower alkyl group which may have lower alkyl group as substituent, lower alkanoyl group which may have a halogen atom as substituent or thiazolyl group which may have lower alkyl group as substituent. $R^6$ is a hydroxyl group, lower alkenyloxy group, lower alkanoyloxy group or alkoxy group which may have lower alkoxy group, tetrahydropyranyloxy group or hydroxyl group as substituent. $R^C$ is a hydrogen atom or lower alkyl group.]; a compound represented by general formula (2):

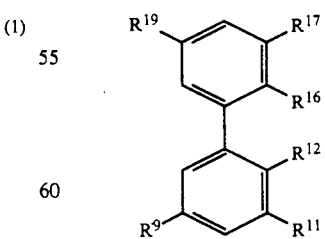

[where $R^{16}$ is a hydroxyl group, lower alkenyloxy group, cycloalkenyloxy group, alkoxy group [which may have lower alkoxy group, tetrahydropylanyloxy group, halogen atoms, lower alkanoyloxy group, carboxy group, hydroxyl group, group:

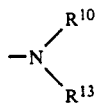

(where $R^{10}$ and $R^{13}$ are, the same or different, hydrogen atom, lower alkyl group or lower alkanoyl group, and moreover, these $R^{10}$ and $R^{13}$ may form a heterocyclic ring of five or six members through with a nitrogen atom to which they are combined), lower alkylthio group, lower alkoxycarbonyl group, phenylthio group which may have hydroxyl group or lower alkyl group as a substituent on the phenyl ring or phthalimido group as a substitutent], group:

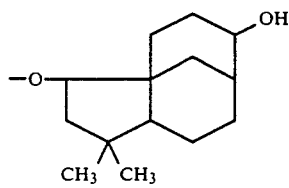

or group:

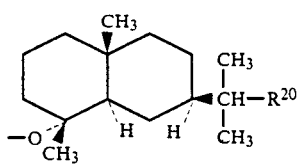

(where $R^{20}$ is a lower alkanoyloxy group). $R^9$ is a lower alkenyl group. $R^{11}$ is a hydrogen atom, cycloalkenyl group or lower alkenyl group. $R^{12}$ is a hydroxyl group, lower alkenyloxy group, cycloalkenyloxy group or lower alkanoyloxy group. These $R^{12}$ and $R^{16}$ may be mutually combined to be a lower alkylene dioxy group. $R^{17}$ is a hydrogen atom, cycloalkenyl group, lower alkenyl group or group:

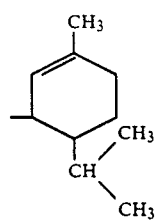

$R^{19}$ is a lower alkenyl group. However, when $R^{17}$ is group:

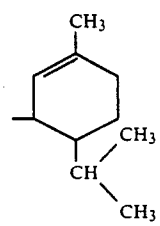

$R^{12}$ and $R^{16}$ are hydroxyl groups, $R^{11}$ is a hydrogen atom, $R^{19}$ and $R^9$ are allyl groups. When $R^{16}$ is group:

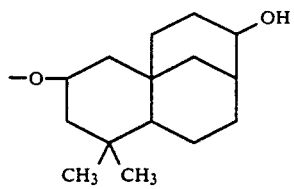

$R^9$ and $R^{19}$ are allyl groups, $R^{12}$ is a hydroxyl group, and $R^{11}$ and $R^{17}$ are hydrogen atoms. Moreover, when $R^{16}$ is group:

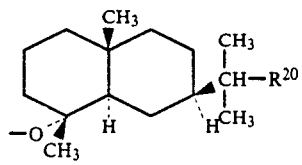

$R^9$ and $R^{19}$ are allyl groups, $R^{12}$ is a lower alkanoyloxy group, and $R^{11}$ and $R^{17}$ are hydrogen atoms.]; a compound represented by the general formula (3):

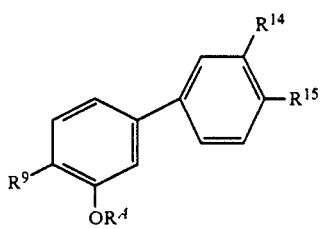

[where $R^9$ is a hydrogen atom or lower alkenyl group. $R^{14}$ is a lower alkenyloxy group or hydroxyl group. $R^{15}$ is a hydrogen atom or lower alkenyl group. $R^A$ is a hydrogen atom or lower alkenyl group.];

a compound represented by the general formula (4):

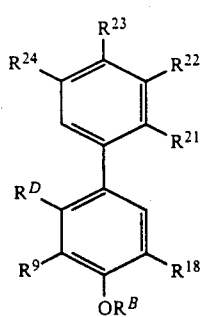

[where $R^9$ is a hydrogen atom or lower alkenyl group. $R^{18}$ is a hydrogen atom, hydroxyl group, lower alkoxy group or lower alkenyl group. $R^{21}$ and $R^{24}$ are hydrogen atoms or lower alkenyl groups. $R^{22}$ is a hydrogen atom, lower alkenyloxy group, hydroxyl group or lower alkenyl group. $R^{23}$ is a hydrogen atom, lower alkenyl group, lower alkenyloxy group or hydroxyl group. $R^B$ is a hydrogen atom, lower alkyl group or lower alkenyl group. However, $R^{22}$ and $R^{23}$ can not be hydroxyl groups simultaneously. $R^D$ is a hydrogen atom or lower alkyl group.]; and a phenyl derivative represented by the general formula (A):

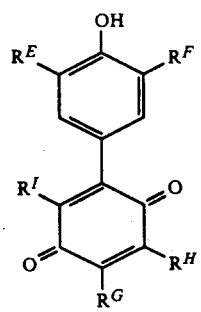

(A)

[where $R^E$, $R^F$ and $R^I$ are lower alkyl groups respectively. $R^G$ and $R^H$ are lower alkoxy groups.].

Biphenyl derivative represented by the general formula (1) includes a new biphenyl derivative represented by the general formula (B);

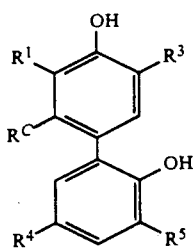

(B)

[where R1, R3, R4, R5 and Rc are the same meanings as mentioned above.].

The compounds represented by aforementioned general formulas (1), (2), (3), (4) and (A) have an effect of remarkably promoting the life of nerve cells and growth of nerve process as well as increasing the enzyme activation of choline acetyl transferase (ChAT) which is an acetylcholine synthesizing enzyme in the cholinergic nervous system. Therefore, the compounds shown by the aforementioned general formulas (1), (2), (3), (4) and (A) have an action to promote the life and growth of cholinergic nerve cells of the central nervous system specifically, and further have a protective action against the disorder of chloinergic nerve cells.

Each group specified in this specification is described in details below.

As example of lower alkyl group, alkyl groups of one to six carbon atoms in straight chain or branched chain shape such as methyl, ethyl, propyl, isopropyl, butyl, tert-butyl, pentyl and hexyl groups can be listed.

As example of lower alkenyl group, alkenyl groups of two to six carbon atoms in straight chain or branched chain shape such as vinyl, allyl, 2-butenyl, 3-butenyl, 1-methylallyl, 2-pentenyl and 2-hexenyl groups can be listed.

As example of phenyl groups which may have hydroxyl group, lower alkyl group or lower alkenyl group as substituent on its phenyl ring, phenyl groups which may have one to three hydroxyl groups, alkenyl groups of two or six carbon atoms in straight chain or branched chain shape, or alkyl groups of one to six carbon atoms in straight chain or branched chain shape such as phenyl, 2-hydroxyphenyl, 3-hydroxyphenyl, 4-hydroxyphenyl, 4-vinylphenyl, 3-allylphenyl, 2-(2-butenyl)-phenyl, 4-(3-butenyl)phenyl, 3-(1-methylallyl)phenyl, 4-(2-pentenyl)phenyl, 2-(2-hexenyl)phenyl, 4-methylphenyl, 3-ethylphenyl, 2-propylphenyl, 4-n-butylphenyl, 3-pentylphenyl, 2-hexylphenyl, 2-hydroxy-3-allyl-5-ethylphenyl, 3,4,5-trimethylphenyl, 2,4,6-trihydroxyphenyl, 2,4-dihydroxyphenyl, 2,6-dimethylphenyl, 2,4-dimethylphenyl, 3,4-dimethylphenyl, 2-hydroxy-3-allylphenyl, 2-methyl-3-allylphenyl groups can be listed.

As halogen atoms, for example, fluorine atom, chlorine atom, bromine atom and iodine atom can be listed.

As example of lower alkanoyl group, alkanoyl groups of one to six carbon atoms in straight chain or branched chain shape such as formyl, acetyl, propionyl, butyryl, isobutyryl, pentanoyl, tert-butylcarbonyl, hexanoyl groups can be listed.

As example of alkoxy group which may have lower alkoxy group, tetrahydropyranyloxy group or hydroxyl group as substituent, alkoxy groups of one to twelve carbon atoms in straight chain or branched chain shape which may have alkoxy group of one to six carbons in straight chain or branched chain shape as substituent, tetrahydropyranyloxy group or hydroxyl group such as methoxy, ethoxy, propoxy, isopropoxy, butoxy, tert-butoxy, pentyloxy, hexyloxy, heptyloxy, octyloxy, nonyloxy, decyloxy, undecyloxy, dodecyloxy hydroxymethoxy, 2-hydroxyethoxy, 1-hydroxyethoxy, 3-hydroxypropoxy, 4-hydroxybutoxy, 1,1-dimethyl-2-hydroxyethoxy, 5-hydroxypentyloxy, 6-hydroxyhexyloxy, 2-methyl-3-hydroxypropoxy, 7-hydroxyheptyloxy, 8-hydroxyoctyloxy, 9-hydroxynonyloxy, 10-hydroxydecyloxy, 11-hydroxyundecyloxy, 12-hydroxydodecyloxy, (2-tetrahydropyranyloxy)methoxy, 2-(3-tetrahydropyranyloxy)ethoxy, 1-(2-tetrahydropyranyloxy)ethoxy, 3-(3-tetrahydropyranyloxy)propoxy, 4-(2-tetrahydropyranyloxy)butoxy, 1,1-dimethyl-2-(4-tetrahydropyranyloxy)ethoxy, 5-(2-tetrahydropyranyloxy)pentyloxy, 6-(3-tetrahydropyranyloxy)hexyloxy, 2-methyl-3-(4-tetrahydropyranyloxy)propoxy, methoxymethoxy, 3-methoxypropoxy, 4-ethoxybutoxy, 6-propxyhexyloxy, 5-isopropoxypentyloxy, 1,1-dimethyl-2-butoxyethoxy, 2-methyl-3-tert-butoxypropoxy, 2-pentyloxyethoxy, hexyloxymethoxy groups can be listed.

As example of cycloalkenyl group, cycloalkenyl groups of three to eight carbon atoms such as cyclopropenyl, cyclobutenyl, cyclopentenyl, cyclohexenyl, cycloheptenyl, cylooctenyl groups can be listed.

As example of lower alkylene group, alkylene groups of one to six carbon atoms in straight or branched chain shape such as methylene, ethylene, trimethylene, 2-methyl trimethylene, 2,2-dimethyl trimethylene, 1-methyl trimethylene, methyl methylene, ethyl methylene, tetramethylene, pentamethylene and hexamethylene groups can be listed.

As example of amide groups which may have lower alkyl group, amide groups which may have one to two alkyl groups of one to six carbon atoms in a straight chain or branched chain shape such as carbamoyl, methyl amide, ethyl amide, propyl amide, isopropyl amide, butyl amide, tert-butyl amide, pentyl amide, hexyl amide, dimethyl amide, diethyl amide, dipropyl amide, dibutyl amide, dipentyl amide, dihexyl amide, N-methyl-N-ethyl amide, N-ethyl-N-propyl amide, N-methyl-N-butyl amide and N-methyl-N-hexyl amide groups can be listed.

As example of saturated or unsaturated hetrocycles of five or six members formed with or without the medium of nitrogen or oxygen atom together with nitrogen atom to which $R^7$ and $R^8$ are combined, piperadinyl group, piperidinyl group, morphorino group, pyrrolidinyl group and imidazolyl group can be listed.

As example of the above-mentioned heterocycles substituted by amide group which may have lower alkyl groups as a substituent, or oxo group, heterocycles substituted by amide group, which may have one to two alkyl groups of one to six carbon atoms in a straight chain or branched chain shape or oxo group such as 4-methyl amide-1-piperidinyl, 4-ethyl amide-1-piperidinyl, 2-dimethyl amide-1-piperidinyl, 3-propyl amide morphorino, 3-tert-butyl amide-1-piperidinyl, 3-pentyl amide-1-pyrrolidinyl, 2-hexyl amide-1-piperidinyl, 2-diethyl amide morphorino, 4-dipropyl amide-1-piperidinyl, 2-dibutyl amide-1-pirrolidinyl, 2-methyl amide-1-pirrolidinyl, 2-carbamoyl-1-pirrolidinyl, 2-dipentyl amide-1-pirrolidinyl, 3-dihexylamide-1-pirrolidinyl, 2-(N-ethyl-N-methyl amide)-1-pirrolidinyl, 4-(N-ethyl-N-propyl amide)-1-piperadinyl, 2-imidazolone-1-yl, 2-methyl amide-1-imidazolyl, 2-oxo-1-pirrolidinyl, 4-oxo-1-piperidinyl, 3-oxo-1-piperadinyl, 2-oxomorphorino groups can be listed.

As example of lower alkoxy group, alkoxy groups of one to six carbon atoms in a straight or branched chain shape such as methoxy, ethoxy, propoxy, isopropoxy, butoxy, tert-butoxy, pentyloxy, hexyloxy groups can be listed.

As example of phenyl-lower alkyl group, phenylalkyl groups of which alkyl part is an alkyl group of one to six carbon atoms in a straight or branched chain shape such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl groups can be listed.

As example of lower alkylthio group, alkylthio groups of one to six carbon atoms in a straight or branched chain shape such as methylthio, ethylthio, propylthio, isopropylthio, butylthio, tert-butylthio, pentylthio, hexylthio groups can be listed.

As example of lower alkylsulfinyl group, alkylsulfinyl groups of one to six carbon atoms in a straight or branched shape such as methylsulfinyl, ethylsulfinyl, isopropylsulfinyl, butylsulfinyl, tert-butylsulfinyl, pentylsulfinyl and hexylsulfinyl groups can be listed.

As lower alkylsulfonyl group, alkylsulfonyl groups of one to six carbon atoms in a straight or branched chain shape such as methylsulfonyl, ethylfulfonyl, isopropylsulfonyl, butylsulfonyl, tert-butylsulfonyl, pentylsulfonyl and hexylsulfonyl groups can be listed.

As example of amino-lower alkyl group which may have lower alkyl group as substituent, alkyl groups of one to six carbon atoms in a straight or branched chain shape as substituent which have amino group which may have one to two alkyl groups of one to six carbon atoms in a straight or branched chain shape, such as aminomethyl, 1-aminoethyl, 2-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, ethylaminomethyl, propylaminomethyl, isopropylaminomethyl, butylaminomethyl, tert-butylaminomethyl, pentylaminomethyl, hexylaminomethyl, dimethylaminomethyl, diethylaminomethyl, dipropylaminomethyl, dibutylaminomethyl, dipentylaminomethyl, dihexylaminomethyl, N-methyl-N-ethylaminomethyl, N-ethyl-N-propylaminomethyl, N-methyl-N-butylaminomethyl, N-methyl-N-hexylaminomethyl, 2-methylaminoethyl, 1-ethylaminoethyl, 3-propylaminopropyl, 4-butylaminobutyl, 1,1-dimethyl-2-pentylaminoethyl, 5-hexylaminopentyl, 6-dimethylaminohexyl, 2-diethylaminoethyl, 1-(N-methyl-N-hexylamino)ethyl, 3-dihexylaminopropyl, 4-dibutylaminobutyl, 2-(N-methyl-N-pentylamino)ethyl groups can be listed.

As example of cycloalkenyloxy group, cycloalkenyloxy groups of three to eight carbon atoms such as cyclopropenyloxy, cyclobutenyloxy, cyclopentenyloxy, cyclohexenyloxy, cycloheptenyloxy, cyclooctenyloxy groups can be listed.

As example of lower alkanoyloxy group, alkanoyloxy groups of one to six carbon atoms in a straight or branched chain shape such as formyloxy, acetyloxy, propionyloxy, butyryloxy, isobutyryloxy, pentanoyloxy, tert-butylcarbonyloxy, hexanoyloxy groups can be listed.

As example of lower alkoxycarbonyl group, alkoxycarbonyl groups of one to six carbon atoms in a straight or branched chain shape such as methoxycarbonyl, ethoxycarbonyl, propoxycarbonyl, isopropoxycarbonyl, butoxycarbonyl, tert-butyoxycarbonyl, pentyloxycarbonyl, hexyloxycarbonyl groups can be listed.

As example of alkoxy group which may have lower alkoxy group, tetrahydropyranyloxy group, halogen atom, lower alkanoyloxy group, carboxy group, hydroxyl group, group:

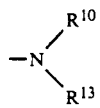

lower alkylthio group, lower alkoxycarbonyl group, phenylthio group which may have hydroxyl group or lower alkyl group as substituent on the phenyl ring, or phthalimids group as substituent, in addition to a lower alkoxy group which may have a lower alkoxy, tetrahydropyranyloxy or hydroxyl group, alkoxy group, which may have alkoxy group of one to six carbon atoms in a straight or branched chain shape, tetrahydropyranyloxy group, halogen atom, alkanoyloxy group of one to six carbon atoms in a straight or branched chain shape, carboxyl group, hydroxyl group, group:

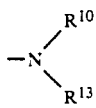

(where $R^{10}$ and $R^{13}$ are the same or different, hydrogen atom, alkyl group of one to six carbons in a straight or branched chain shape, or alkanoyl group of one to six carbon atoms in straight or branched chain shape, these $R^{10}$ and $R^{13}$ may form a heterocyclic ring composed of five or six members together with nitrogen atom to which they are combined), alkylthio group of one to six carbon atoms in straight or branched chain shape, alkoxycarbonyl group of one to six carbon atoms in straight or branched chain shape, phenylthio group which may have hydroxyl group or alkyl group of one to six carbon atoms in straight or branched chain shape on the phenyl ring as substituent or phthalimide group as a substituent such as aminomethoxy, 1-aminoethoxy, 2-aminoethoxy, 3-aminopropoxy, 4-aminobutyoxy, 5-aminopentyloxy, 6-aminohexyloxy, 1,1-dimethyl-2-aminoethoxy, 2-methyl-3-aminopropoxy, methylaminomethoxy, ethylaminomethoxy, propylaminomethoxy, isopropylaminomethoxy, butylaminomethoxy, tert-butylaminomethoxy, pentylaminomethoxy, hexylaminomethoxy, dimethylaminomethoxy, diethylaminomethoxy, dipropylaminomethoxy, dibutylaminomethoxy, 2-dipentylaminoethoxy, dihexylaminomethoxy, N-methyl-N-ethylaminoethoxy, N-ethyl-N-propylaminomethoxy, N-methyl-N-butylaminomethoxy, N-methyl-N-hexylaminomethoxy, 1-methylaminoethoxy, 2-ethylaminoethoxy, 3-propylaminopropoxy, 4-butylaminobutoxy, 1,1-dimethyl-2-pentylaminoethoxy, 5-hexylaminopentyloxy, 6-dimethylaminohexyloxy, 2-diethylaminoethoxy, 1-(N-methyl-N-hexylamino)ethoxy, 3-dihexylaminopropoxy, 4-dibutylaminobutoxy, 2-(N-methyl-N-pentylamino)ethoxy, formylaminomethoxy, acetylaminomethoxy, propionylaminomethoxy, butyrylaminomethoxy, isobutyrylaminomethoxy, pentanoylaminomethoxy, tert-butylcarbonylaminomethoxy, hexanoylaminomethoxy, 2-acetylaminoethoxy, 1-formylaminoethoxy, 3-acetylaminopropoxy, 4-butyrylaminobutoxy, 5-hexanoylaminopentyloxy, 6-pentanoylaminohexyloxy, 2-(N-ethyl-N-acetylamino)ethoxy, 3-(N-methyl-N-acetylamino)propoxy, methylthiomethoxy, 2-methylthioethoxy, 1-ethylthioethoxy, 3-propylthiopropoxy, 4-isopropylthiobutoxy, 5-butylthiopentyloxy, 6-pentylthiohexyloxy, 1,1-dimethyl-2-hexylthioethoxy, 2-methyl-3-methylthiopropoxy, methoxycarbonylmethoxy, 2-ethoxycarbonylethoxy, 1-propoxycarbonylethoxy, 3-isopropoxycarbonylpropoxy, 4-butoxycarbonylbutoxy, 5-pentyloxycarbonylpentoxy, 6-hexyloxycarbonylhexyloxy, 4-ethoxycarbonylethoxy, phthalimidemethoxy, 2-phthalimideethoxy, 1-phthalimideethoxy, 3-phthalimidepropoxy, 4-phthalimidebutoxy, 5-phthalimidepentyloxy, 6-phthalimidehexyloxy, fluoro methoxy, 2-chloroethoxy, 5-bromohexyloxy, 3-iodopropoxy, 1-chloroethoxy, 4-bromobutoxy, 5-iodopentyloxy, 6-acetyloxyhexyloxy, propionyloxymethoxy, 2-butyryloxyethoxy, 1-pentanoyloxyethoxy, 3-hexanoyloxypropoxy, 4-acetyloxybutoxy, 5-acetyloxypentyloxy, carboxymethoxy, 1-carboxyethoxy, 2-carboxyethoxy, 3-carboxypropoxy, 4-carboxybutoxy, 5-carboxypentyloxy, 6-carboxyhexyloxy, 6-(1-pyrrolidinyl)hexyloxy, 6-(1-imidazolyl)hexyloxy, 6-(3,5-di-t-butyl-4-hydroxyphenylthio)hexyloxy, (1-piperadinyl)methoxy, 2-(1-piperidinyl)ethoxy, 3-morphorinopropoxy, 4-(1-pyrrolidinyl)butoxy, 5-(1-imidazolyl)pentyloxy, phenylthiomethoxy, 2-(4-methylphenylthio)ethoxy, 1-(2-hydroxyphenylthio)ethoxy, 3(2,4-dihydroxyphenylthio)propoxy, 4-(2,6-dimethylphenylthio)butyoxy, 5-(2-hydroxy-3-t-butylphenylthio)pentyloxy groups can be listed.

As example of lower alkenyloxy group, alkenyl group of two to six carbon atoms in straight or branched chain shape such as vinyloxy, allyloxy, 2-butenyloxy, 3-butenyloxy, 1-methylallyloxy, 2-pentenyloxy, 2-hexenyloxy groups can be listed.

As example of heterocycle composed of five or six members formed together with a nitrogen atom to which $R^{10}$ and $R^{13}$ are combined, piperadinyl group, piperidinyl group, morphorino group, pyrrolidinyl group and imidazolyl group can be listed.

As example of phenylthio group which may have hydroxyl group or lower alkyl group on the phenyl ring as substituent, phenylthio group which may have one to three hydroxyl groups or alkyl groups of one to six carbons in straight or branched chain shape on the phenyl ring as substituent such as phenylthio, 2-hydroxyphenylthio, 3-hydroxyphenylthio, 4-hydroxyphenylthio, 4-methylphenylthio, 3-ethylphenylthio, 2-propylphenylthio, 4-n-butylphenylthio, 3-pentylphenylthio, 2-hexylphenylthio, 4-hydroxy-3,5-di-t-butylphenylthio, 3,4,5-trimethylphenylthio, 2,4-dihydroxyphenylthio, 2,6-dimethylphenylthio or 2-hydroxy-3-t-butylphenylthio groups can be listed.

As lower alkyl groups which may have lower alkoxy group or hydroxyl group as substitutional group, in addition to the aforementioned lower alkyl groups, alkyl groups of one to six carbon atoms in straight or branched chain shape which may have alkoxy group of one to six carbon atoms in straight of branched chain shape or hydroxyl group as substituent such as hydroxymethyl, 2-hydroxyethyl, 1-hydroxyethyl, 3-hydroxypropyl, 4-hydroxybutyl, 1,1-dimethyl-2-hydroxyethyl, 5-hydroxypentyl, 6-hydroxyhexyl, 2-methyl-3-hydroxypropyl, methoxymethyl, 1-ethoxyethyl, ethoxymethyl, 3-methoxypropyl, 4-ethylbutyl, 6-propoxyhexyl, 5-isopropoxypentyl, 1,1-dimethyl-2-butoxyethyl, 2-methyl-3-tert-butoxypropyl, 2-pentyloxyethyl or hexyloxymethyl group can be listed.

As example of lower alkanoyl group which may have halogen atom as substituent, in addition to the aforementioned lower alkanoyl groups, alkanoyl groups of one to six carbon atoms in straight or branched chain shape which may have one to three halogen atoms as substituent such as 2,2,2-trifluoroacetyl, 2,2,2-trichloroacetyl, 2-chloroacetyl, 2-bromoacetyl, 2-fluoroacetyl, 2-iodoacetyl, 2,2-difluoroacetyl, 2,2-dibromoacetyl, 3,3,3-trifluoropropionyl, 3,3,3-trichloropropionyl, 3-chloropropionyl, 2,3-dichloropropionyl, 4,4,4-trichlorobutylyl, 4-fluorobutylyl, 5-chloropentanoyl, 3-chloro-2-methylpropionyl, 6-bromohexanoyl or 5,6-dibromohexanoyl group can be listed.

As example of thiazolyl group which may have lower alkyl group as substituent, those of one to six carbon atoms in straight or branched chain shape as substitutional group such as thiazolyl, 2-methylthiazolyl, 4-ethylthiazolyl, 5-propylthiazolyl, 2-n-butylthiazolyl, 4-pentylthiazolyl or 5-hexylthiazolyl group can be listed.

Out of compounds represented by general formulas (1) or (2) in this invention, compounds (5), (6) or (7) as shown below are produced, for example, by a method described below.

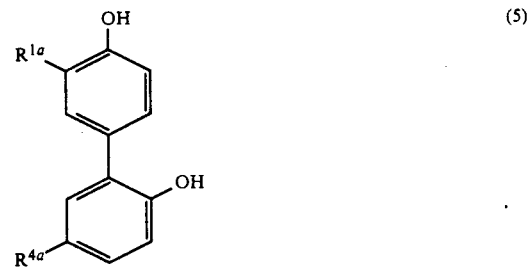

(5)

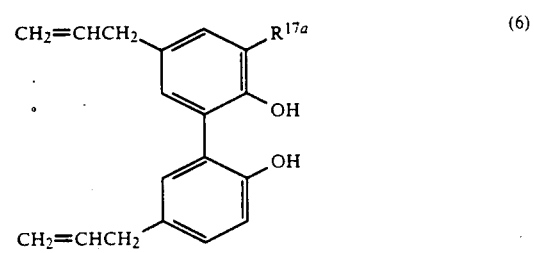

(6)

-continued (7)

[structure: biphenyl with CH₂=CHCH₂ groups, $R^{16a}$, and OH]

[where $R^{1a}$ and $R^{4a}$ are both allyl groups. $R^{17a}$ is a hydrogen atom or group:

[structure with CH₃ groups and CH(CH₃)₂]

$R^{16a}$ is group:

[structure: bicyclic with -O-, OH, and two CH₃ groups] .]

Compounds (5), (6) and (7) are extracted and isolated from *Magnolia obovata* T$_{HUNB}$ (a Japanese drug "Wakoboku"). The extraction and isolation is performed, for example, by the following method. First of all, *Magnolia obovata* T$_{HUNB}$ is extracted by using a known polar solvent such as ethyl acetate or methanol, the liquid extract is filtrated, the filtered liquid is concentrated under the reduced pressure to obtain a primary extract, and the object compound is obtained from the extract by using various methods utilizing chemical or physical property of the object compound. In order to obtain the object compound, such known methods of using difference in solubilities between the object compound and impurities, of using difference in absorptive affinities to absorbents such as activated charcoal, amberite, silica gel, ion-exchange resin and Sephadex, of using difference in partition rates between the two liquids, or a combination of these methods can be used. More preferably, such method that the primary extract is put in a silica gel column chromatography to extract by using an appropriate solvent such as mixed solvent of n-hexane and ethyl acetate, the liquid extract is concentrated under the reduced pressure, and after refining the concentrated liquid by using silica gel column chromatography, Sephadex is applied to elute the object component by using an appropriate solvent such as methanol may be used.

In compound (5), in order to obtain a compound of which both $R^{1a}$ and $R^{4a}$ are propyl, groups, the compound (5) obtained by the extraction and isolation may be applied to a catalytic reduction by using a catalyst such as palladium-carbon.

A compound shown by a general formula (8):

(8)

[structure: biphenyl with CH₂=CHCH₂ groups, $R^{16b}$, and $R^{12a}$]

[where $R^{12a}$ is a lower alkanoyloxy group, $R^{16b}$ is a group:

[structure: decalin system with CH₃ groups, -O-, H, and CH-R²⁰]

(where $R^{20}$ is the same as defined above)] is produced by reacting a compound shown by general formula $$(R^{25})_2O \quad (9)$$

or general formula $$R^{25}X \quad (10)$$

[where $R^{25}$ is a lower alkanoyl group, and X is a halogen atom] to the compound extracted and isolated by aforementioned method.

The above lower-alkanoylating reaction is performed in the presence or absence of basic compound. As example of basic compound to be used, alkali metals such as metallic sodium, metallic potassium, and hydroxides, carbonates or bicarbonates of such alkali metals, or organic bases such as N,N-dimethylaminopyridine pyridine or piperidine can be listed. This reaction is proceeded either with or without a solvent. As example of solvent, there are ketones such as acetone and methylethyl ketone, ethers such as diethyl ether and dioxane, aromatic hydrocarbons such as benzene, toluene and xylene, water and pyridine. While at least approximately same molar ratio of the compound shown by general formula (9) or (10) is used, generally, it is preferable to use from the same molar ratio to excessively larger molar ratio. Although the reaction proceeds at temperature between 0° to 200° C., it is generally preferable to proceed the reaction at 0° to 150° C. The reaction time is generally about 0.5 to 5 days.

Reaction formula-1

[structures (11) and (12) with substituents $R^1$, $R^2$, $R^3$, $R^4$, $R^5$, $R^6$, $R^c$, B, C]

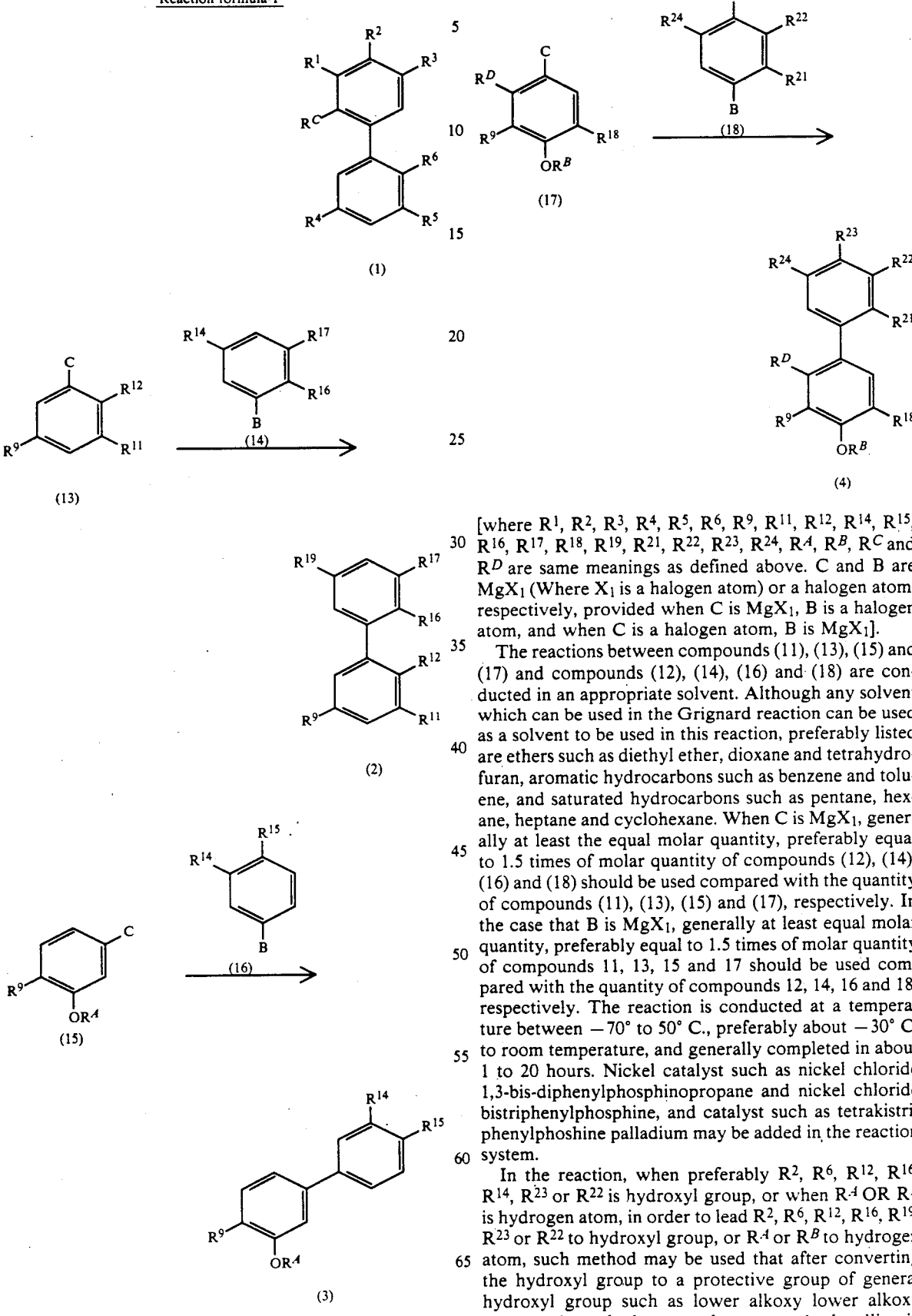

[where $R^1$, $R^2$, $R^3$, $R^4$, $R^5$, $R^6$, $R^9$, $R^{11}$, $R^{12}$, $R^{14}$, $R^{15}$, $R^{16}$, $R^{17}$, $R^{18}$, $R^{19}$, $R^{21}$, $R^{22}$, $R^{23}$, $R^{24}$, $R^A$, $R^B$, $R^C$ and $R^D$ are same meanings as defined above. C and B are $MgX_1$ (Where $X_1$ is a halogen atom) or a halogen atom, respectively, provided when C is $MgX_1$, B is a halogen atom, and when C is a halogen atom, B is $MgX_1$].

The reactions between compounds (11), (13), (15) and (17) and compounds (12), (14), (16) and (18) are conducted in an appropriate solvent. Although any solvent which can be used in the Grignard reaction can be used as a solvent to be used in this reaction, preferably listed are ethers such as diethyl ether, dioxane and tetrahydrofuran, aromatic hydrocarbons such as benzene and toluene, and saturated hydrocarbons such as pentane, hexane, heptane and cyclohexane. When C is $MgX_1$, generally at least the equal molar quantity, preferably equal to 1.5 times of molar quantity of compounds (12), (14), (16) and (18) should be used compared with the quantity of compounds (11), (13), (15) and (17), respectively. In the case that B is $MgX_1$, generally at least equal molar quantity, preferably equal to 1.5 times of molar quantity of compounds 11, 13, 15 and 17 should be used compared with the quantity of compounds 12, 14, 16 and 18, respectively. The reaction is conducted at a temperature between $-70°$ to $50°$ C., preferably about $-30°$ C. to room temperature, and generally completed in about 1 to 20 hours. Nickel catalyst such as nickel chloride 1,3-bis-diphenylphosphinopropane and nickel chloride bistriphenylphosphine, and catalyst such as tetrakistriphenylphoshine palladium may be added in the reaction system.

In the reaction, when preferably $R^2$, $R^6$, $R^{12}$, $R^{16}$, $R^{14}$, $R^{23}$ or $R^{22}$ is hydroxyl group, or when $R^A$ OR $R^B$ is hydrogen atom, in order to lead $R^2$, $R^6$, $R^{12}$, $R^{16}$, $R^{19}$, $R^{23}$ or $R^{22}$ to hydroxyl group, or $R^A$ or $R^B$ to hydrogen atom, such method may be used that after converting the hydroxyl group to a protective group of general hydroxyl group such as lower alkoxy lower alkoxy group and tetrahydropyranyloxy group by handling in the same conditions as in the reaction of compounds (1f) and (21) of reaction formula-9 which is shown below, the Grignard reaction is conducted, and then, $R^2$ or $R^6$ in compound (1) is hydrolyzed in the same conditions as in the hydrolysis of lower alkoxy group which has tetrahydropyranyloxy group as its substituent.

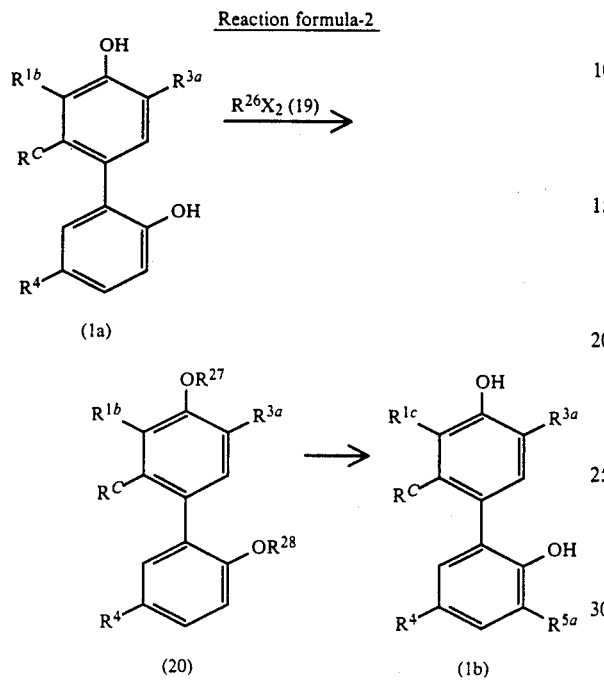

Reaction formula-2

[where $R^4$ and $R^C$ are same meanings as mentioned before, $R^{1b}$ and $R^{3a}$ are the same meanings as $R^1$ and $R^3$, respectively, provided that at least one of $R^{1b}$ and $R^{3a}$ is hydrogen atom, $R^{5a}$ is a hydrogen atom, lower alkenyl group or cycloalkenyl group, $X_2$ is a halogen atom, $R^{26}$ is a lower alkenyl group or cycloalkenyl group, $R^{27}$ and $R^{28}$ are hydrogen atom, lower alkenyl group or cycloalkenyl group. However, $R^{27}$ and $R^{28}$ must not hydrogen atoms simultaneously, $R^{1c}$ and $R^{3b}$ are the same meanings as $R^1$ and $R^3$, respectively, provided that at least one of $R^{1c}$ and $R^{3b}$ should be lower alkenyl group or cycloalkenyl group.]

The reaction between compounds (1a) and (19) is conducted in the presence of a basic compound in an appropriate solvent. As example of a solvent to be used in this reaction, water, lower alcohols such as methanol, ethanol, propanol, ethers such as diethyl ether, tetrahydrofuran, dioxane, ethylene glycol monomethyl ether, aromatic hydrocarbons such as benzene, toluene, xylene, esters, such as methyl acetate, ethyl acetate, ketones such as acetone, methylethyl ketone, polar solvents such as acetonitrile, dimethylformamide, dimethylsulfoxide, hexamethylphosphoric triamide, or mixture of these solvents can be listed. As usable basic compound, there are, for example, inorganic bases such as sodium hydroxide, potassium hydroxide, sodium carbonate, potassium carbonate, sodium bicarbonate, potassium bicarbonate, sodium hydride, alkali metals such as metallic sodium, metallic potassium, alcoholate of alkali metals such as sodium ethylate, sodium methylate organic bases such as triethyl amine, pyridine, N,N-dimethyl aniline, N-methyl morphorine, 4-methyl aminopyridine, 1,5-diazabicyclo[4,3,0]nonen-5DBN), 1,8-diazabicyclo[5,4,0]undecen-7(DBU), 1,4-diazabicyclo[2,2,2]octane(DABCO). Generally, compound (19) is used at equal molar ratio, preferably equal to five times of molar ratio against compound (1a). The reaction is performed generally at 0° to 150° C., preferably at room temperature to 100° C., and it is completed generally in about 0.5 to 20 hours.

The reaction which leads compound (20) to compound (1b) is called the Claisen rearrangement, which is performed in an appropriate solvent by heating. As a solvent to be used in this reaction, there are, for example, solvents having high boiling points such as dimethylformamide, tetrahydronaphthalene, N-N-dimethylaniline and diphenylether. The reaction is completed generally at 100° to 250° C., preferably at 150° to 250° C. in about 1 to 30 hours.

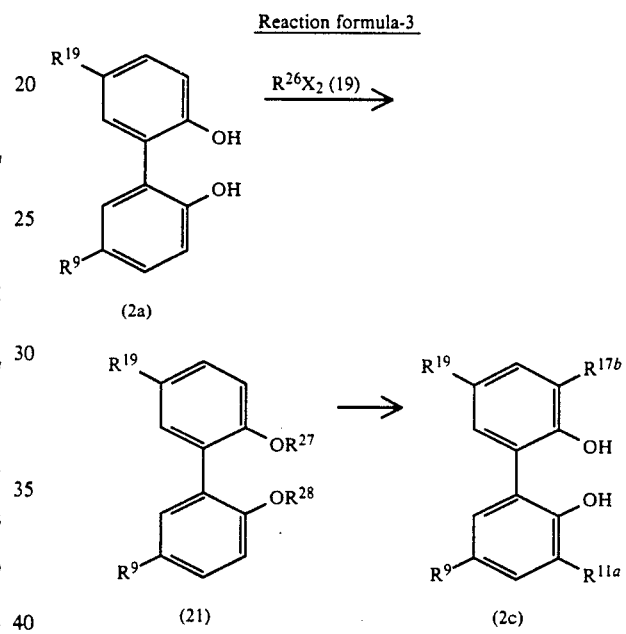

Reaction formula-3

[where $R^9$, $R^{10}$, $R^{19}$, $R^{22}$, $R^{26}$, $R^{27}$, $R^{28}$ and $X_2$ are the same meanings as mentioned above, $R^{11a}$ and $R^{17b}$ are hydrogen atom, lower alkenyl group or cycloalkenyl group. However, $R^{11a}$ and $R^{17b}$ must not be hydrogen atoms simultaneously.]

The reaction between compounds (2a) and (19) can be performed in the same conditions as in the reaction between compounds (1a) and (19) in the aforementioned reaction formula-2.

The reaction which leads compound (21) to compound (2c) is conducted in the same conditions as in the reaction which leads compound (20) to compound (1b) in the aforementioned reaction formula-2.

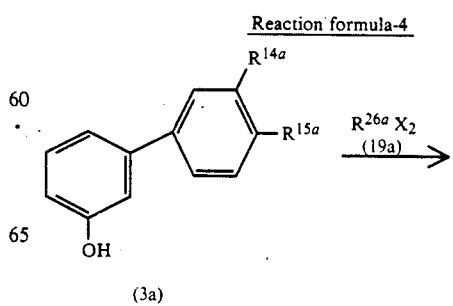

Reaction formula-4

-continued
Reaction formula-4

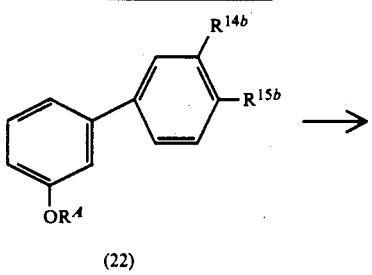

(22)

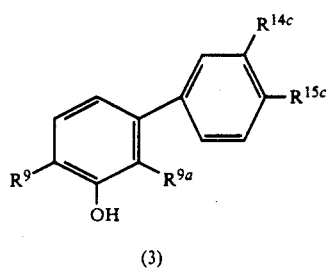

(3)

[where $R^9$, $R^A$ and $X_2$ are the same meanings as mentioned above. $R^{26a}$ is lower alkenyl group. $R^{9a}$ is a hydrogen atom or lower alkenyl group. $R^{14a}$ and $R^{15a}$ are mutually different and a hydrogen atom or hydroxyl group, $R^{14b}$ and $R^{15b}$ are mutually different and hydrogen atom, hydroxyl group or lower alkenyloxy group, $R^{14c}$ and $R^{15c}$ are mutually different and hydrogen atom, hydroxyl group or lower alkenyl group. However, when one of $R^9$ and $R^{9a}$ is lower alkenyl group, the other must be hydrogen atom. In addition, when one of $R^{14b}$ and $R^{15b}$ is hydroxyl group, the other should be hydrogen atom, and $R^A$ should be lower alkenyl group. Moreover, when one of $R^{14b}$ and $R^{15b}$ is lower alkenyloxy group, the other should be hydrogen atom. Furthermore, when one of $R^{14c}$ and $R^{15c}$ is lower alkenyl group, the other should be hydroxyl group.]

The reaction between compound (3a) and compound (19a) is performed in the same conditions as that of compounds (1a) and (19) of aforementioned reaction formula-2.

The reaction which leads compound (22) to compound (3) is performed in the same conditions as that of compounds (20) and (1b).

Reaction formula-5

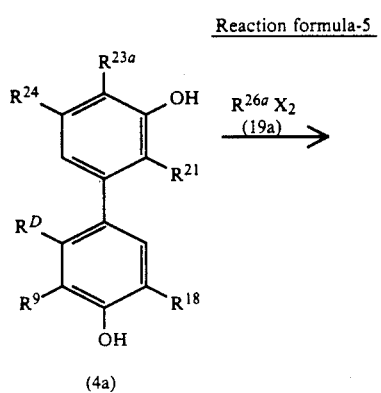

Reaction formula-5

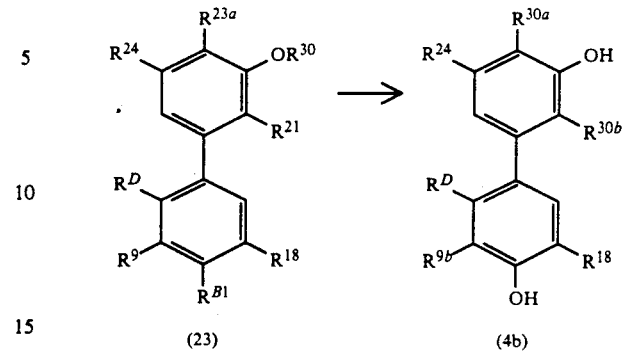

[where $R^9$, $R^{18}$, $R^{21}$, $R^{24}$, $R^{26a}$, $R^D$ and $X_2$ are the same meanings as mentioned above. However, in the case that at least one of $R^9$ and $R^{19}$ and at least one of $R^{21}$ and $R^{23a}$ should be hydrogen atoms. $R^{B1}$ is a hydrogen atom or lower alkenyl group. $R^{9b}$ is a hydrogen atom or lower alkenyl group. $R^{18a}$ is the same meanings as $R^{18}$. $R^{23a}$ is a hydrogen atom or lower alkenyl group. $R^{30}$, $R^{30a}$ and $R^{30b}$ are hydrogen atom or lower allkenyl group. However, $R^{30}$ and $R^{B1}$ must not be hydrogen atoms simultaneously.]

The reaction between compounds (4a) and (19a) is performed in the same conditions as in the reaction between compounds (1a) and (19) of aforementioned reaction formula-2.

The reaction which leads compound (23) to compound (4b) is performed in the same conditions as in the reaction which leads compound (20) to compound (1b) of aforementioned reaction formula-2.

Reaction formula-6

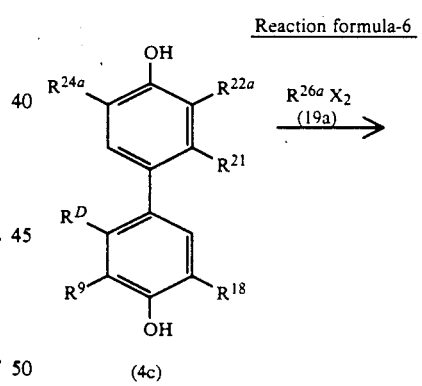

(4c)

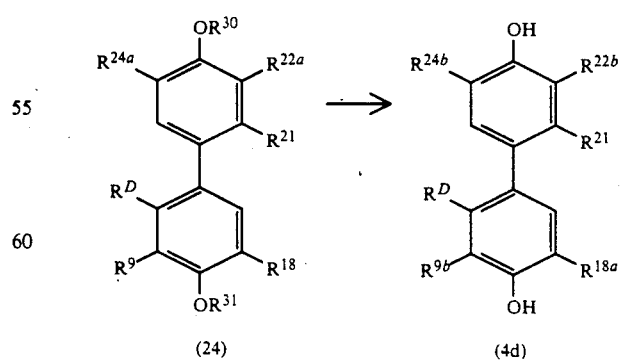

(24)                (4d)

[where $R^9$, $R^{18}$, $R^{21}$, $R^{24}$, $R^{26a}$, $R^{30}$, $R^{9b}$ $R^{18a}$, $R^D$ and $X_2$ are the same meanings as mentioned above. $R^{22a}$ is a hydrogen atom or lower alkenyl group. $R^{24a}$ is a hydrogen atom or lower alkenyl group. $R^{31}$ is a hydrogen atom or lower alkenyl group. However, at least either $R^{22a}$ or $R^{24a}$ is a hydrogen atom. $R^{22b}$ and $R^{24b}$ are hydrogen atom or lower alkenyl group. However, $R^{30}$ and $R^{31}$ must not be hydrogen atom simultaneously.].

The reaction between compounds (4c) and (19a) is performed in the same conditions as in the reaction between compounds (1a) and (19) of aforementioned reaction formula-2.

The reaction which leads compound (24) to compound (4d) is performed in the same conditions as in the reaction which leads compound (20) to compound (1b) of aforementioned reaction formula-2.

Reaction formula-7

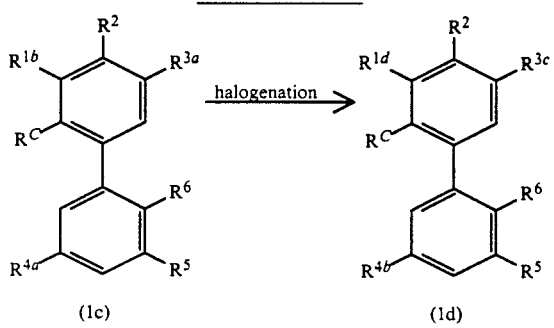

[where $R^2$, $R^5$, $R^C$ and $R^6$ are the same meanings as mentioned above. $R^{1b}$, $R^{3a}$ and $R^{4a}$ are the same meanings as $R^1$, $R^3$ and $R^4$, respectively. However, at least one of $R^{1b}$, $R^{3a}$ or $R^{4a}$ should be hydrogen atom. $R^{1d}$, $R^{3c}$ and $R^{4b}$ are the same meanings as $R^1$, $R^3$ and $R^4$, respectively. However, at least one of $R^{1d}$, $R^{3c}$ and $R^{4d}$ should be halogen atom.]

The halogenation reaction of compound (1c) is performed in an appropriate solvent in the presence of a halogenating agent. As a halogenating agent to be used in the reaction, there are, for example, halogen molecules such as bromine and chlorine, iodine chloride, sulfuryl chloride, N-succinimide halide such as N-bromosuccinimide and N-chloro succinimide. Generally, the halogenating agent is used at equal molar ratio to ten times molar ratio, preferably equal molar to five times molar ratio against compound (1c). As a usable solvent, there are, for example, hydrocarbon halides such as dichloromethane, dichloroethane, chloroform and carbon tetrachloride, aliphatic acids such as acetic acid and propionic acid. The reaction is performed generally at 0° C. to the boiling point of the solvent, preferably at about 0° to 50° C. and completed generally in about 0.5 to 10 hours approximately.

Reaction formula-8

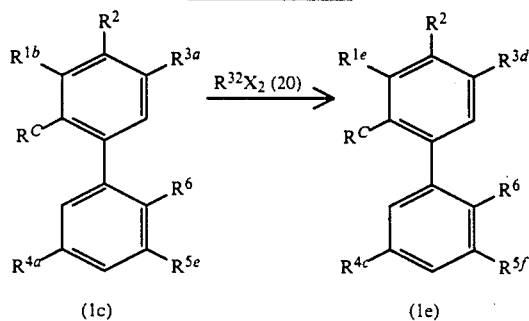

[where $X_2$, $R^2$, $R^6$, $R^{1b}$, $R^C$ $R^{3a}$ and $R^{4a}$ are the same meanings as mentioned above. $R^{1e}$, $R^{3d}$ and $R^{4c}$ are the same meanings as $R^1$, $R^3$ and $R^4$, respectively. $R^{5e}$ and $R^{5f}$ are the same meanings as $R^5$. However, at least one of $R^{1b}$, $R^{3a}$, $R^{4a}$ and $R^{5e}$ should be hydrogen atom, and at least one of $R^{1e}$, $R^{3d}$, $R^{5f}$ and $R^{4c}$ should be lower alkanoyl group. $R^{32}$ is lower alkanoyl group.]

The reaction which leads compound (1c) to compound (1e) is performed in the presence of an acid, in the presence or absence of an appropriate solvent. As an acid to be used in the reaction, there are, for example, aluminium chloride, zinc chloride, iron chloride, tin chloride, boron trifluoride, boron tribromide and concentrated sulfuric acid. As usable solvent, for example, aromatic hydrocarbons such as carbon disulfide, nitrobenzene and chlorobenzene, or halogenated hydrocarbons such as dichloromethane, dichloroethane, trichloroethane and tetrachloroethane may be listed. The reaction is performed generally at 0° to 200° C. preferably at room temperature to 180° C. and completed generally in about 10 minutes to 15 hours. Generally, compound (20) is used at equal molar ratio, preferably equal to five times molar ratio against compound (1c).

In the case that $R^2$ or $R^6$ is a hydroxyl group, while sometimes these are lower-alkanoylated simultaneously, they can be easily separated. In aftermentioned compound (1) or (2), in the same conditions as in the hydrolysis reaction used in the case that $R^2$, $R^3$ or $R^{16}$ is lower alkoxy lower alkoxy, the above compound can be hydrolyzed to lead to a compound where $R^2$ or $R^6$ is a hydroxyl group.

Reaction formula-9

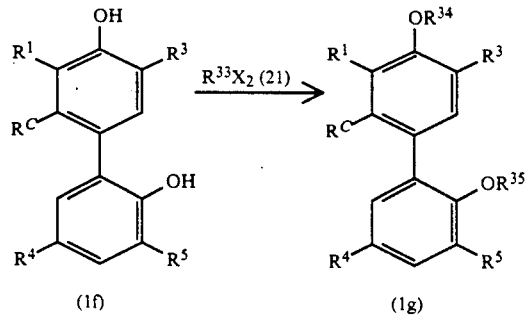

[where $R^1$, $R^3$, $R^4$, $R^5$, $R^C$ and $X_2$ are the same meanings as mentioned above. $R^{33}$ is an alkyl group which may have lower alkoxy group, tetrahydropyranyloxy group or hydroxyl group as substituent. $R^{34}$ and $R^{35}$ are hydrogen atom or alkyl group which may have lower alkyl group, tetrahydropyranyloxy group or hydroxyl group as substituent. However, $R^{34}$ and $R^{35}$ should not be hydrogen atoms simultaneously.]

The reaction between compounds (1f) and (21) is performed in the same conditions as in the reaction between compounds (1a) and (19) of aforementioned reaction formula-2.

A compound which has lower alkyl group for $R^{34}$ or $R^{35}$ in compound (1g) can be produced by using alkylating agent such as diazomethane or dialkyl sulfate such as dimethyl sulfate.

In the case that at least one of $R^3$ and $R^5$ in compound (1f) is a hydroxyl group, while the hydroxyl group may sometimes react with compound (21) simultaneously, it can be easily separated.

Reaction formula-10

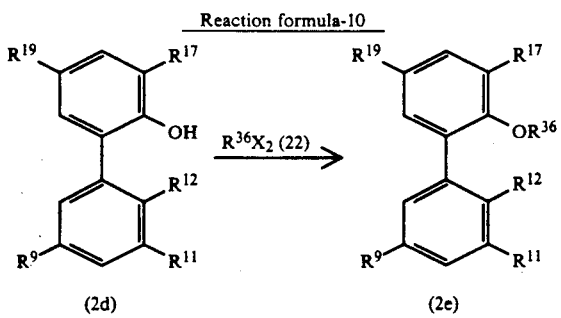

(2d)   (2e)

[where $R^9$, $R^{11}$, $R^{12}$, $R^{17}$, $R^{19}$ and $X_2$ are the same meanings as mentioned above. $R^{36}$ is an alkyl group which may have lower alkoxy group, tetrahydropyranyl group, hydroxyl group, halogen atom, lower alkanoyloxy group, carboxy group, group:

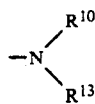

(where $R^{10}$ and $R^{13}$ are the same meanings as mentioned above), lower alkylthio group, phenylthio group which may have hydroxyl group or lower alkyl group of the phenyl ring as substitutional group or phthalimide group as substituent.]

In the reaction between compounds (2d) and (22); except that equal molar to 1.5 times molar ratio of compound (22) to the ratio of compound (2d) is preferably used, the conditions of performing the reaction are the same as in the reaction between compounds (1a) and (19) of aforementioned reaction formula-2. A compound which has lower alkyl group for $R^{36}$ of compound (2e) can also be produced by using alkylating agent such as diazomethane or dialkyl sulfate such as dimethyl sulfate.

Reaction formula-11

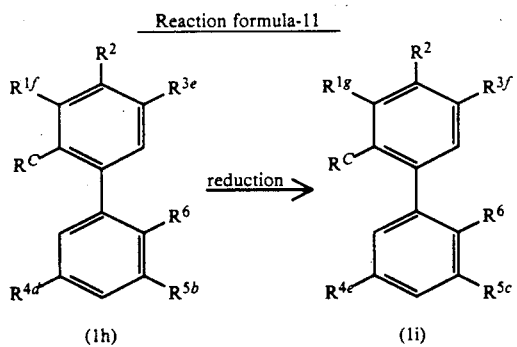

(1h)   (1i)

[where $R^2$, $R^C$ and $R^6$ are the same meanings as mentioned above. $R^{1f}$, $R^{3e}$, $R^{4d}$ and $R^{5b}$ are the same as $R^1$, $R^3$, $R^4$ and $R^5$, respectively. However, at least one of $R^{1f}$, $R^{3e}$, $R^{4d}$ and $R^{5b}$ is a lower alkenyl group. $R^{1g}$, $R^{3f}$, $R^{4e}$ and $R^{5c}$ are the same as $R^1$, $R^3$, $R^4$ and $R^5$, respectively. However, at least one of $R^{1g}$, $R^{3f}$, $R^{4e}$ and $R^{5c}$ should be a lower alkyl group.]

The reduction reaction of component (1h) is performed by conducting a catalytic reduction in an appropriate solvent in the presence of a catalyst. As usable solvent in this reaction, there are, for example, water, acetic, acid, alcohols such as methanol, ethanol, isopropyl alcohol, hydrocarbons such as hexane, cyclohexane, ethers such as diethylene glycol dimethyl ether, dioxane, tetrahydrofuran, diethyl ether, esters such as ethyl acetate, methyl acetate, polar solvents such as dimethylformamide or mixtures of these solvents. As usable catalysts, palladium, palladium-black, palladium-carbon, platinum, platinum oxide, copper chromite, Raney nickel or the like are listed. Generally catalyst should be used at 0.02 times to equal ratio to compound (1h). The reaction should be performed generally at $-20°$ to $100°$ C., preferably at about $0°$ to $70°$ C. with general hydrogen pressure of 1 to 10 atm, and it is completed approximately in about 0.5 to 20 hours.

Reaction formula-12

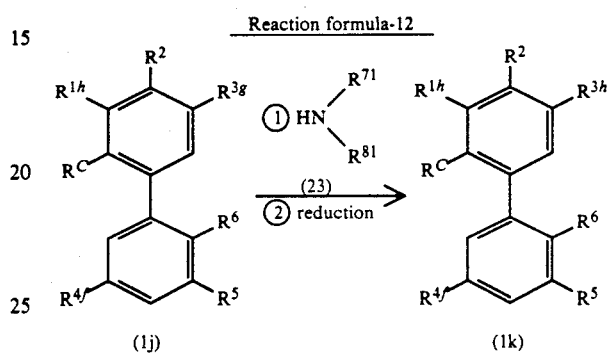

(1j)   (1k)

[where $R^2$, $R^C$ and $R^6$ are the same meanings as mentioned above. $R^{1h}$ is $R^1$ except for lower alkanoyl group. $R^{4f}$ is $R^4$ except for lower alkanoyl group. $R^{3g}$ is a lower alkanoyl group. $R^{71}$ and $R^{81}$ are $R^7$ and $R^8$, respectively, except for lower alkanoyl group. $R^{5g}$ is $R^5$ except for lower alkanoyl group which may have a halogen atom as substituent. $R^{3h}$ is group:

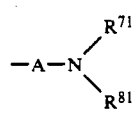

(where A, $R^{71}$ and $R^{81}$ are the same meanings as mentioned above). ]

The reaction between a compound shown by general formula (1j) and a compound shown by general formula (23) is performed with or without an appropriate solvent in the presence or absence of a dehydrant. As usable solvent in the reaction, there are, for example, alcohols such as methanol, ethanol and isopropyl alcohol, aromatic hydrocarbons such as benzene, toluene and xylene, halogenated hydrocarbons such as dichloromethane, dichloroethane, chloroform and carbon tetrachloride, non-protonic polar solvents such as dimethylformamide, dimethylacetoamide and N-methylpyrrolidone or mixtures of these solvents. As dehydrants, there are, for example, desiccating agents which are generally used for dehydrating solvents such as molecular sieve, mineral acids such as hydrochloric acid, sulfuric acid and boron trifluoride, and organic acids such as p-toluene sulfonate. The reaction is performed generally at room temperature to $250°$ C., preferably at $50°$ to $200°$ C., and completed generally in about 1 to 48 hours. The ratio of a compound shown by general formula (23) for use is not specifically limited, but generally at least equal molar ratio, preferably equal molar ratio to excessively larger ratio to the compound shown by general formula (1j) should be used. As for dehydrant, in the case of desiccating agent, generally excessively larger ratio should be used, and in the case that an acid is used, equal ratio to catalyst should be used. A compound shown by following general formula:

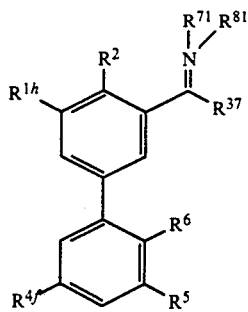

(where $R^{37}$ is a hydrogen atom or lower alkyl) which is thus obtained is applied to the succeeding reduction reaction without isolation.

Various methods can be employed for this reduction reaction, for example, conditions of reduction reaction of aforementioned compound (1h) may be used, and preferably a method of using a hydrogenating reductant is used. As example of usable hydrogenating reductant, lithium aluminum hydride, sodium boron hydride, diborane or the like can be listed. The reductant is used at least equal molar ratio, preferably equal to 18 times molar ratio of compound (1j). This reduction reaction is generally performed by using an appropriate solvent such as water, lower alcohols such as methanol, ethanol, isopropyl alcohol, ethers such as tetrahydrofuran, diethyl ether and diglyme, generally at $-60°$ to $50°$ C., preferably $-30°$ C. to room temperature for approximately in about 10 minutes to 5 hours. In the case that lithium aluminum hydride or diboran is used as reductant, it is preferable to use anhydrous solvent such as diethyl ether, tetrahydrofuran and diglyme.

Reaction formula-13

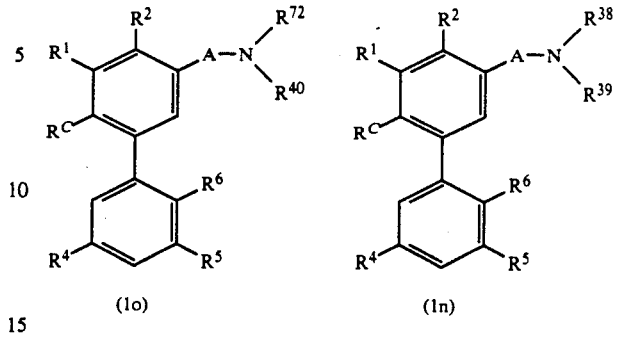

-continued
Reaction formula-13

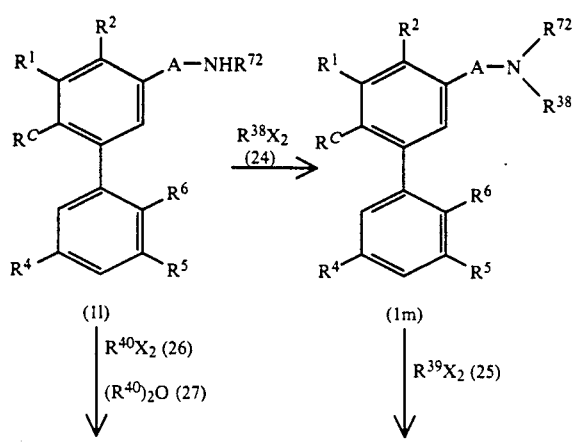

[where $R^1$, $R^2$, $R^4$, $R^6$, $R^C$ and $X_2$ are the same meanings as mentioned above. $R^{72}$ is a hydrogen atom or lower alkyl group. $R^{38}$ and $R^{39}$ are lower alkyl groups. $R^{40}$ is a lower alkanoyl group.]

The reaction between compounds (12) and (24), and that between a compound which has a hydrogen atom as $R^{72}$ in compound (1m) and compound (25) are performed in an appropriate inert solvent in the presence of dehalogenating hydrogen agent. As inert solvent used in this reaction, halogenated hydrocarbons such as dichloromethane and chloroform, ethers such as tetrahydrofuran and diethyl ether, aromatic hydrocarbons such as benzene, toluene, xylene, esters such as methyl acetate and ethyl acetate, and polar solvents such as dimethylformamide, dimethyl sulfoxide, hexamethylphosphoric triamide, acetonitrile, acetone, acetic acid, pyridine and water can be listed. As usable dehalogenating hydrogen agent, there are, for example, organic bases such as triethylamine, trimethylamine, pyridine, dimethyl aniline, N-methylmorpholine, 4-dimethyl aminopyridine, 4-(1-pyrrolidinyl)pyridine, 1,5-diazabicyclo[4,3,0]nonen-5 (DBM), 1,8-diazabicyclo[5,4,0]undecen-7 (DBU), 1,4-diazabicyclo[2,2,2]octane (DABCO), sodium acetate and the like, inorganic bases such as sodium hydride, potassium carbonate, sodium carbonate, potassium bicarbonate, sodium bicarbonate, potassium hydroxide, sodium hydroxide and the like. Generally at least equal molar ratio, preferably equal to three times molar ratio of compound (24) or (25) is used to compound (11) or (1m). The reaction is performed generally at $-20°$ to $150°$ C., preferably $0°$ to $100°$ C. for approximately in about 5 minutes to 15 hours.

The reaction between compound (11) and compound (26) or (27) is conducted in the presence or absence of a basic compound, preferably in the presence of that, with or without an appropriate solvent.

As example of appropriate solvent, the aromatic hydrocarbons mentioned above, lower alcohols such as methanol, ethanol and propanol, dimethylformamide, dimethylsulfoxide, halogenated hydrocarbons such as chloroform and methylene chloride, acetone, pyridine and the like are listed. At least equal molar ratio, preferably equal to 10 times molar ratio of compound (26) or (27) to compound (10) is used. The reaction is performed at generally room temperature to $150°$ C., preferably room temperature to $100°$ C., for about 0.5 to 15 hours.

In the case of a compound which may be aminolower alkyl group, which may have lower alkyl group as substituent, as substituent of $R^5$ in compound (11) or (1m), the group may sometimes react to compound (24), (25) or (26), but it can be easily separated.

Reaction formula-14

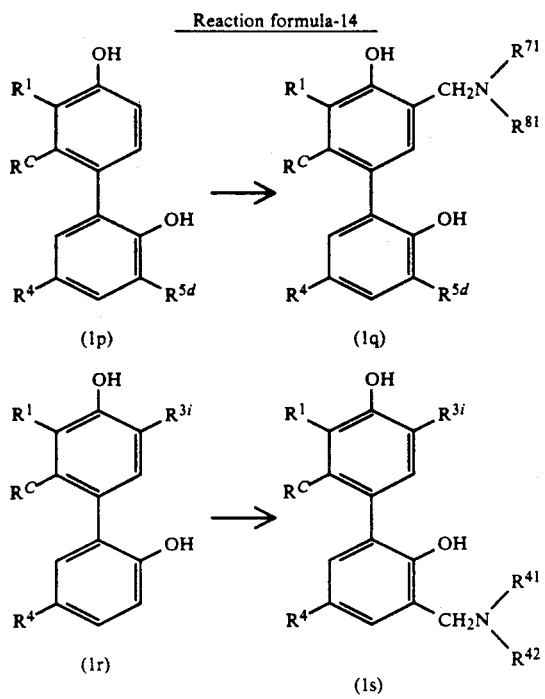

[where $R^1$, $R^4$, $R^{71}$, $R^C$ and $R^{81}$ are the same meanings as mentioned above. $R^{5d}$ and $R^{3i}$ are the same as $R^5$ and $R^3$ except for hydrogen atom, respectively. $R^{41}$ and $R^{42}$ are, the same or different, hydrogen atom or lower alkyl group.]

In order to lead compound (1p) to compound (1q) or compound (1r) to compound (1s), method I of reacting

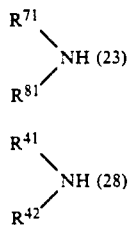

(where $R^{71}$, $R^{81}$, $R^{41}$ and $R^{42}$ are the same meanings as mentioned above) and formaldehyde (Mannich Reaction) and method II of reacting

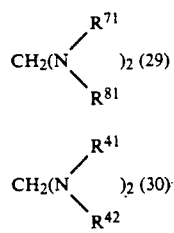

can be used.

By method I, compounds (1p), (23) and formaldehyde or compounds (1r), (28) and formaldehyde are reacted in an appropriate solvent in the presence or absence of an acid. As usable solvent in this reaction, any solvent which is generally used in the Mannich Reaction can be used, and, for example, water, alcohols such as methanol, ethanol and isopropyl alcohol, alkane acids such as acetic acid and propionic acid, acidic anhydrides such as acetic anhydride, polar solvents such as acetone and dimethyl formamide or mixtures of these solvents can be listed. As usable acid, there are, for example, mineral acids such as hydrochloric acid and hydrobromic acid, and organic acids such as acetic acid. As formaldehyde, aqueous solution containing 20 to 40 weight % of formaldehyde, its trimer, polymer (paraformaldehyde) or the like are generally used. Generally equal molar ratio, preferably equal to 10 times molar ratio of compound (23) or (28) should be used to compound (1p) or (1r). As for formaldehyde, at least equal molar ratio, generally excessively larger ratio to compound (1p) or (1r) should be used. The reaction is proceeded generally at 0° to 200° C., preferably at room temperature to approximately 150° C., and it is completed in about 0.5 to 10 hours.

By method II, the reaction is performed in the presence of an acid with or without an appropriate solvent. As usable acid in the reaction, there are, for example, mineral acids such as hydrochloric acid, hydrobromic acid and sulfuric acid, and organic acids such as acetic acid and acetic anhydride, and acetic anhydride is preferably used. As usable solvent in the reaction, those which are used in aforementioned method I can be used. Generally at least equal molar ratio, preferably equal to 5 times molar ratio of compound (29) or (30) is used to compound (1p) or (1r). The reaction is performed generally at 0° to 150° C., preferably at room temperature to approximately 100° C., and it is completed in about 0.5 to 5 hours.

Reaction formula-15

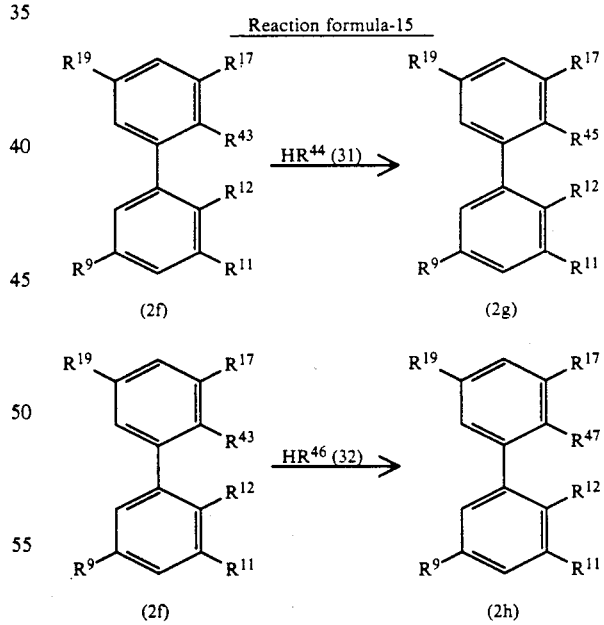

[where $R^9$, $R^{11}$, $R^{12}$, $R^{17}$ and $R^{19}$ are the same meanings as mentioned above. $R^{40}$ is an alloy group which has a halogen atom as substituent. $R^{44}$ is group:

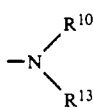

(where $R^{10}$ and $R^{13}$ are the same meanings as mentioned above), lower alkanoyloxy group, lower alkylthio group or phenylthio group which may have hydroxyl group or lower alkyl group as substituent on its phenyl ring. $R^{46}$ is a lower alkoxy group, hydroxyl group, lower alkanoyloxy group or phthalimide group. M is alkali metal such as sodium and potassium or silver. $R^{47}$ is an alkoxy group which has lower alkoxy group, hydroxyl group, lower alkanoyloxy group or phthalimide group as substituent, and $R^{45}$ is alkoxy group which has, as substituent, lower alkanoyloxy group, group:

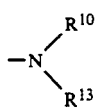

(where $R^{10}$ and $R^{13}$ are the same meanings as mentioned above), lower alkylthio group or phenylthio group which may have hydroxyl group or lower alkyl group as substituent on its phenyl ring.]

The reaction between compounds (2f) and (31) is performed in the same conditions as in the reaction between compounds (1a) and (19) of aforementioned reaction formula-2. Iodinated alkali metals such as sodium iodide and potassium iodide may be added in the reaction system.

In the case that $R^{44}$ is a lower alkylthio group, the reaction may be performed, in addition to compound (2f), by using alkali mineral salts such as sodium and potassium of the compound.

In the reaction conditions, in the case that $R^{12}$ of compound (2f) is hydroxyl group, due to an intramolecular reaction, $R^{45}$ and $R^{12}$ of compound (2g) may be combined to generate a compound which has lower alkylene dioxy group, but this bond can be easily separated.

The reaction between compounds (2f) and (32) is performed by reacting these two compounds in an appropriate solvent. As usable solvents in this reaction, in addition to lower alkane acids such as acetic acid, those which can be used in the reaction between compounds (1a) and (19) of aforementioned reaction formula-2 can be listed. At least equal molar ratio, preferably equal to 1.5 times molar ratio of compound (32) to compound (2f) should be used. The reaction is performed generally at room temperature to 200° C., preferably at room temperature to 150° C., and it is completely generally in about 1 to 5 hours.

Reaction formula-16

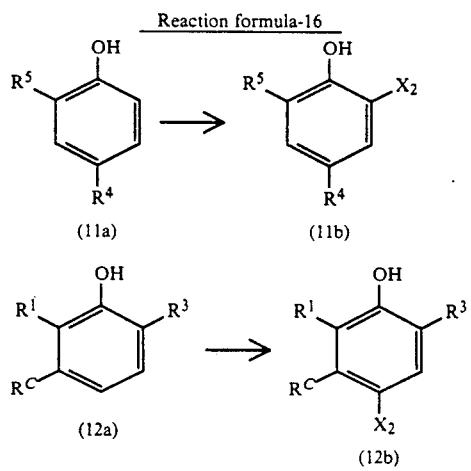

-continued
Reaction formula-16

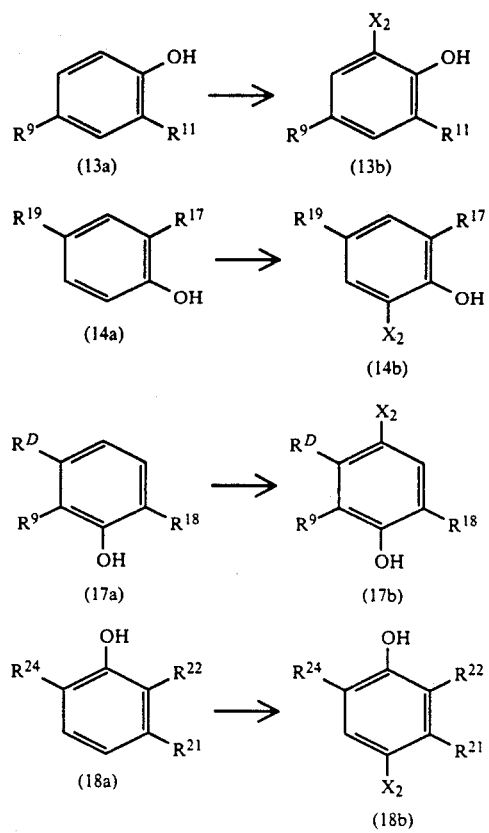

[where $R^4$, $R^5$, $R^1$, $R^3$, $R^9$, $R^{11}$, $R^{17}$, $R^{19}$, $R^{18}$, $R^{21}$, $R^{22}$, $R^{24}$, $R^C$, $R^D$ and $X_2$ are the same meanings as mentioned above.]

The halogenating reaction of compounds (11a), (12a), (13a), (14a), (17a) and (18a) is performed in the same conditions as in the halogenating reaction of aforementioned reaction formula-7. In the reaction, when $R^4$ of compound (11a), $R^1$ or $R^3$ of compound (12a), $R^{18}$ of compound (17a) and $R^{22}$ or $R^{24}$ of compound (18a) are hydrogen atoms. Halogen atom may be introduced in their places in the obtained compounds, but these can be easily separated.

The hydroxyl group of compounds (11b) and (12b) is reacted in the same conditions as in the reaction between compounds (1f) and (21) of aforementioned reaction formula-9 to lead into compounds (11b) and (12b) in which the hydroxyl group is converted to alkoxy group which may have lower alkoxy group, tetrahydropyranyloxy group or hydroxyl group as substituent.

The hydroxyl group of compound (14b) is reacted in the same conditions as in the reaction between compounds (2d) and (22) of aforementioned reaction formula-10 to be lead into compound (14b) in which the hydroxyl group is converted to group-$OR^{36}$ (where $R^{36}$ is same as mentioned before).

The hydroxyl group of general formulas 11b and 12b can be converted to lower alkoxy group by alkylating agents such as dialkyl sulfate such as dimethyl sulphate or diazomethane as same manner as in aforementioned reaction formula-9.

In the case that $R^4$ of a compound shown by general formula-1 is lower alkylthio group, by oxidizing this component, the compound is led to another compound in which $R^4$ is lower alkylsulfinyl group or lower alkylsulfonyl group.

The oxidizing reaction which leads lower alkylthio group to lower alkylsulfinyl group is performed in an appropriate solvent in the presence of an oxidant. As usable solvents in this reaction, there are, for example, water, organic acids such as formic acid, acetic acid and trifluoroacetic acid, alcohols such as methanol and ethanol, halogenated hydrocarbons such as chloroform and dichloromethane. As usable oxidants, any conventionally known oxidant can be used as far as it can oxidize thio group into sulfinyl group or sulfonyl group, and preferably peracids such as performic acid, peracetic acid, petrifluoroacetic acid, perbenzoic acid, m-chloroperbenzoic acid and o-carbonylperbenzoic acid, hydrogen peroxide, sodium meta-periodate, bichromates such as bichromatic acid, sodium bichromate and potassium bichromate, permanganates such as permanganic acid, potassium permanganate and sodium permanganate can be listed.

Generally equal molar quantity, preferably equal to double molar quantity of oxidant should be used to the starting material. The reaction is performed generally at 0° to 40° C., preferably at 0° C. to room temperature, and it is completed generally in about 1 to 10 hours.

The oxidative reaction which leads lower alkylthio group to lower alkylsulfonyl group is performed in the same conditions as in the oxidizing method which leads aforementioned lower alkylthio group to lower alkylsulfinyl group except that at least double molar quantity, preferably 2 to 4 times molar ratio of oxidant to starting material is used.

The reaction which leads lower alkylsulfinyl group to lower alkylsulfonyl group is performed in the same conditions as in the oxidizing method which leads aforementioned lower alklythio group to lower alkylsulfinyl group.

In the cases that $R^2$ or $R^6$ of compound (1) is lower alkoxy group which may have lower alkoxy group as substitutent, that $R^5$ is lower alkoxy group, that $R^{16}$ of compound (2) is lower alkoxy group which may have lower alkoxy group, that $R^{18}$ of compound (4) is lower alkoxy group, or that $R^8$ is lower alkyl group, by heat treatment in a mixture of acids such as hydrobromic acid and hydrochloric acid and solvents such as water, methanol, ethanol and isopropyl alcohol at temperature between 30° to 150° C., preferably 50° to 120° C., the compounds can be led into compound (1), (2) or (4) in which $R^2$, $R^6$ or $R^{16}$ is hydroxyl group. In addition, by hydrolysis, compound (1) or (2) in which $R^2$, $R^6$ or $R^{14}$ is hydroxyl group can be obtained as well. The hydrolysis is performed in an appropriate solvent in the presence of an acid. As solvents, for example, water, lower alcohols such as methanol, ethanol and isopropyl alcohol, ethers such as dioxane and tetrahydrofuran, halogenated hydrocarbons such as dichloromethane, chloroform and carbon tetrachloride, polar solvents such as acetonitrile and mixtures of these solvents can be listed. As acids, for example, mineral acids such as hydrochloric acid, sulfuric acid and hydrobromic acid, Lewis acids such as boron trifluoride, aluminium chloride and boron tribromide, iodides such as sodium iodide and potassium iodide and mixtures of aforementioned Lewis acids and iodides can be listed. The reaction is proceeded generally at room temperature to 150° C., preferably room temperature to 100° C., and normally it is completed in about 0.5 to 15 hours.

In the case that $R^2$ or $R^6$ of compound (1), or $R^{16}$ of general formula-2 is lower alkoxy group which has tetrahydropyranyloxy group as substituent, by hydrolysis, the compound can be led to another compound (1) or (2) in which $R^2$, $R^6$ or $R^{16}$ is alkoxy group which has hydroxyl group as substituent. In the hydrolysis, any reaction condition of general hydrolysis may be applied, and specifically, in the presence of basic compounds such as sodium carbonate, potassium carbonate, sodium hydroxide, potassium hydroxide and barium hydroxide, mineral acids such as sulfuric acid, hydrochloric acid and nitric acid and organic acids such as acetic acid, aromatic sulfonic acid. The reaction is performed in a solvent such as water, alcohols such as methanol, ethanol, isopropyl alcohol, ketones such as acetone, methyl ethylketone, ethers such as dioxane, ethyleneglycol dimethyl ether, solvents such as acetic acid or mixtures of these solvents. The reaction is proceeded generally at room temperature to 200° C., preferably at room temperature to 150° C., and normally it is completed in about 0.5 or 15 hours.

In the case that $R^{12}$ of compound (2) is lower alkanoyloxy group and that $R^2$ or $R^6$ of compound (i) is lower alkanoyloxy group, by employing hydrolysis in the same conditions as in the case that $R^2$, $R^6$, or $R^{16}$ is lower alkoxy group which has tetrahydropropyranyloxy group as substituent, the compound can be led to the other compound (1) in which $R^2$ or $R^6$ is hydroxyl group or still other compound (2) in which $R^{12}$ is hydroxyl group.

In the case that $R^{16}$ of compound (2) is alkoxy group substituted by lower alkanoyloxy, by hydrolysis in the same conditions as in the hydrolysis reaction in the case that $R^2$, $R^6$, or $R^{16}$, is lower alkoxy-lower alkoxy group, the compound is led into the other compound (2) in which $R^{16}$ is alkoxy group substituted by hydroxy group.

In the case that $R^{16}$ of compound (2) is alkoxy group substituted by lower alkoxycarbonyl, by hydrolysis in the same conditions as in the hydrolysis reaction in the case that $R^2$, $R^6$ or $R^{16}$ is lower alkoxy lower-alkoxy group, the compound can be led into the other compound (2) in which $R^{16}$ is alkoxy group substituted by carboxy group.

In the case that $R^{16}$ of compound (2) is alkoxy group substituted by lower alkoxycarbonyl group, by reduction, the compound can be led into the other compound (2) in which $R^{16}$ is alkoxy group substituted by hydroxyl group. The reduction reaction is performed in the same conditions as in the reduction of aforementioned reaction formula-12.

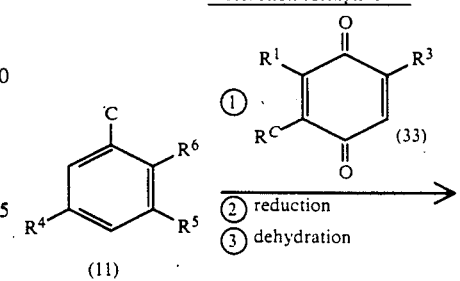

Reaction formula-17

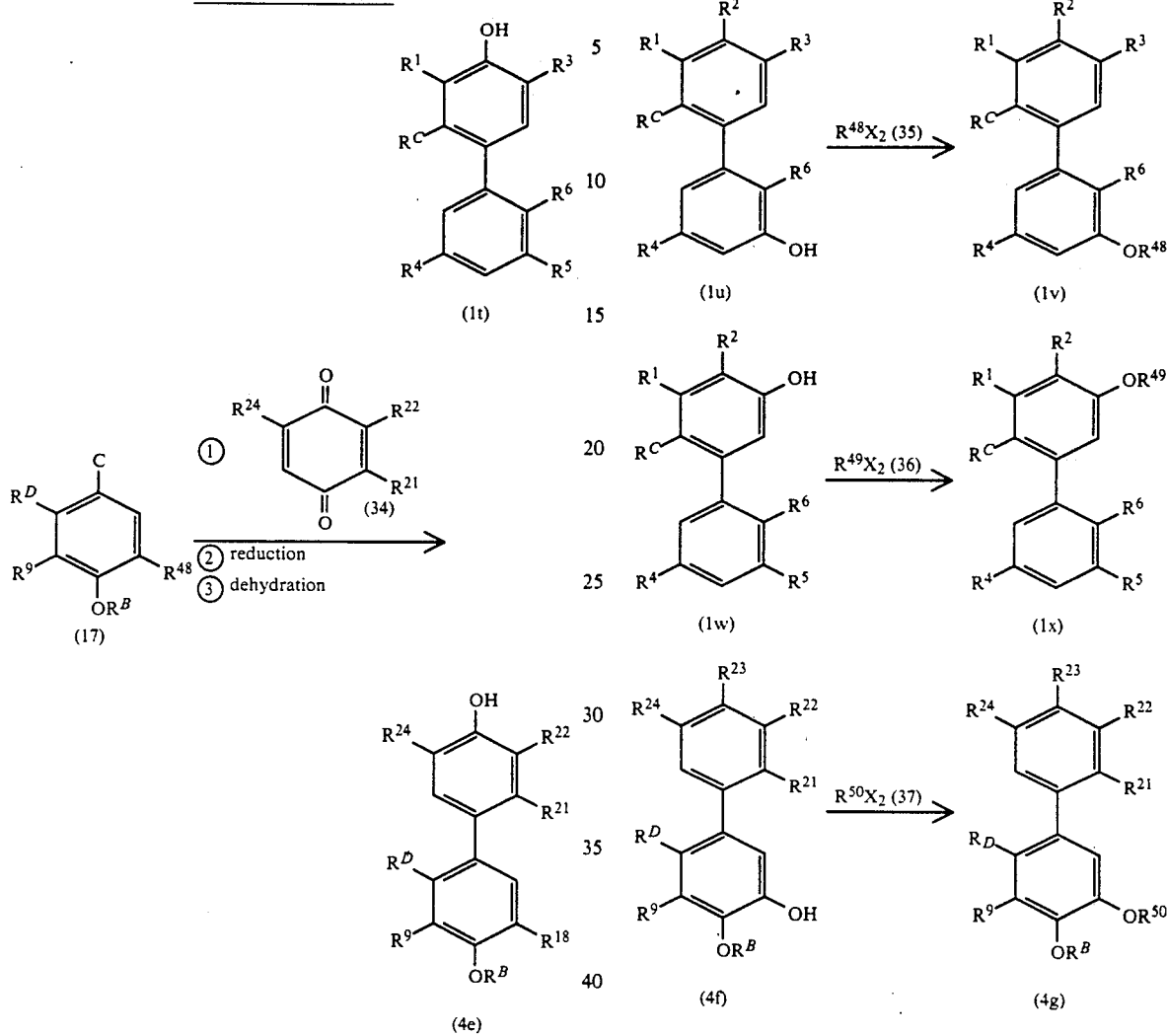

[where C, $R^1$, $R^3$, $R^4$, $R^5$, $R^6$, $R^9$, $R^{18}$, $R^{21}$, $R^{22}$, $R^{24}$, $R^C$, $R^D$ and $R^B$ are same as mentioned before.]

The reactions between compounds (11) and (33), and (17) and (34) are performed in the same conditions as in the reaction between compounds (11) and (12). The succeeding reduction is performed in the same conditions as in the reduction of compound (1j) in aforementioned reaction formula-12 except that the reaction time is approximately about 1 to 15 hours. The succeeding dehydration is performed in the presence of mineral acids such as hydrochloric acid, sulfuric acid and hydrobromic acid in water, lower alcohols such as methanol, ethanol and isopropyl alcohol, ethers such as dioxane and tetrahydrofuran, polar solvents such as acetonitrile and mixtures of these solvents. The reaction is proceeded generally at room temperature to 150° C., preferably at room temperature to 100° C., and it is completed in about 1 to 30 hours normally.

[where $R^1$, $R^2$, $R^3$, $R^4$, $R^6$, $R^C$, $R^{21}$, $R^{22}$, $R^{23}$, $R^{24}$, $R^9$, $R^B$ $R^D$ and $X_2$ are the same meanings as mentioned above. $R^{48}$ is lower alkyl group. $R^{49}$ is lower alkyl group which may have lower alkoxy group or hydroxyl group as substituent. $R^{50}$ is lower alkyl group.]

Reactions between compounds (1u) and (35), compounds (1w) and (36) and compounds (4f) and (37) are performed in the same conditions as in the reaction between compounds (1f) and (21) of aforementioned reaction formula-9.

Compounds which have lower alkyl group for $R^{48}$, $R^{49}$ or $R^{50}$ of compound (1v), (1x) or (4g), respectively can be produced by using alkylating agent such as diazomethane or dialkyl sulfate such as dimethyl sulfate as well.

In the case that at least one of components $R^2$, $R^3$ and $R^6$ of compound (1u) is hydroxyl group, the hydroxyl group may simultaneously react to compound (35), but this can be easily separated. In the case that at least one of components $R^2$, $R^5$ and $R^6$ of compound (1w) is hydroxyl group, the hydroxyl group may simultaneously react with compound (36), but this may be easily separated. In the case that either $R^{23}$ or $R^{22}$ of compound (4f) is hydroxyl group and/or $R^B$ is hydrogen atom, the hydroxyl group may simultaneously react to compound (37), but this can be easily separated.

Reaction formula-19

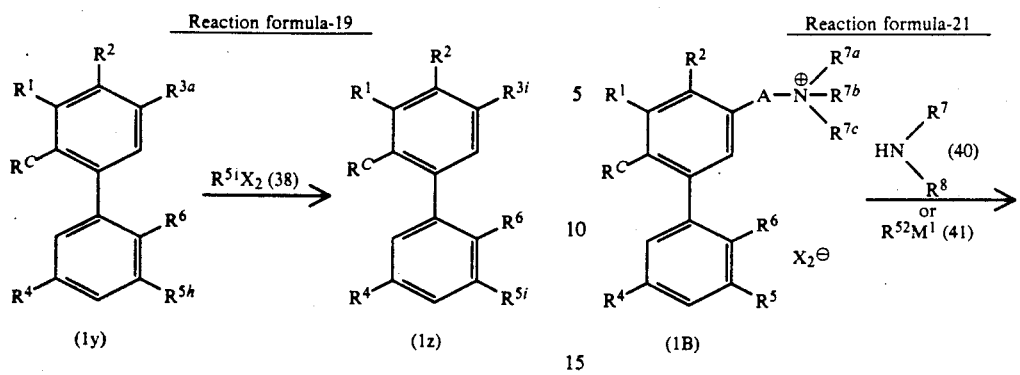

(1y) → (1z)

[where $R^1$, $R^2$, $R^{3a}$, $R^4$, $R^6$, $R^C$ and $X_2$ are the same meanings as mentioned above. $R^{5h}$ is equal to aforementioned $R^5$. However, at least one of $R^{3a}$ and $R^{5h}$ is hydrogen atom. $R^{3i}$ and $R^{5i}$ are equal to aforementioned $R^3$ and $R^5$, respectively. However, at least one of $R^{3i}$ and $R^{5i}$ should be lower alkanoyl group which has halogen atom as substituent. $R^{51}$ is lower alkanoyl group which has halogen atom as substituent.]

The reaction between compounds (1y) and (38) can be performed in the same conditions as in the reaction between compounds (1c) and (20) of aforementioned reaction formula-8.

Reaction formula-20

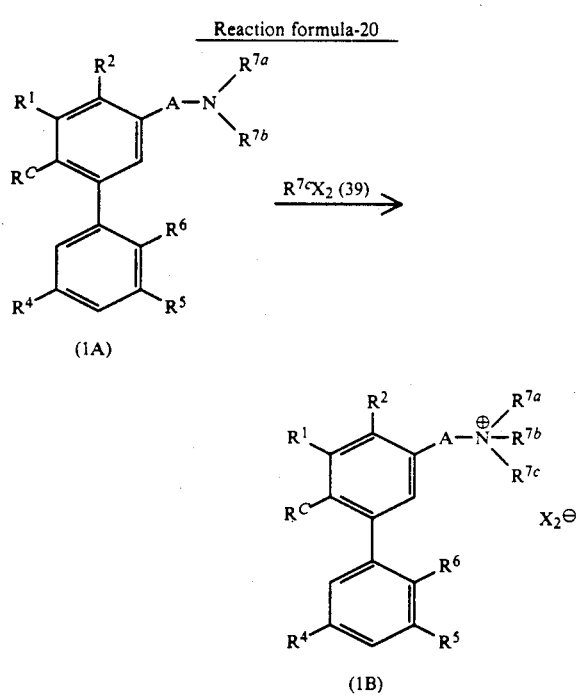

(1A) → (1B)

[where $R^1$, $R^2$, $R^4$, $R^5$, $R^6$, $R^{7a}$, $R^{7b}$, $R^{7c}$, A and $X_2$ are the same meanings as mentioned above.]

The reaction between compounds (1A) and (39) can be performed by reacting them in an appropriate solvent. As usable solvent in this reaction, any solvent which is used in the reaction between compounds (11) and (24) of aforementioned reaction formula-13 can be listed, for example. The reaction is performed generally at −20° to 150° C., preferably 0° to 100° C., which is completed in about 1 to 15 hours. At least equal molar ratio, preferably an excessive ratio of compound (39) should be used to compound (1A).

Reaction formula-21

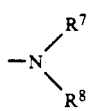

(1B) → (1C)

[where $R^1$, $R^2$, $R^4$, $R^5$, $R^6$, $R^7$, $R^8$, $R^C$, $R^{7a}$, $R^{7b}$, A and $X_2$ are the same meanings as priorly mentioned above. $R^{52}$ is a lower alkoxy group or hydroxyl group. $M^1$ is an alkali metal such as sodium and potassium. $R^{53}$ is group:

$$-N\begin{matrix}R^7\\R^8\end{matrix}$$

(where $R^7$ and $R^8$ are the same meanings as mentioned above) or $R^{52}$.]

The reaction between compounds (1B) and (40) or (41) can be proceeded by reacting them in an appropriate solvent. As usable solvent in this reaction, any solvent which is used in the reaction between compound (1a) and (19) of aforementioned reaction formula-2 can be listed, for example. The reaction is performed generally at room temperature to 150° C., preferably at room temperature to approximately 100° C., which is completed approximately in about 1 to 15 hours. Generally an excessive quantity of compound (40) or (41) should be used to compound (1B).

Reaction formula-22

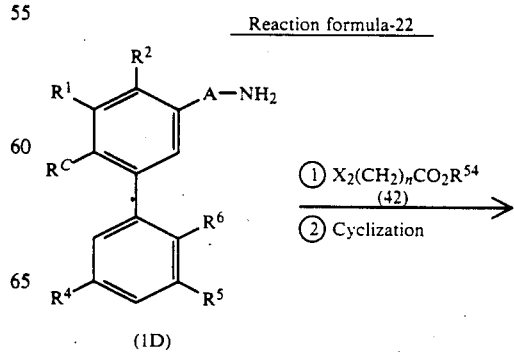

(1D)

-continued
Reaction formula-22

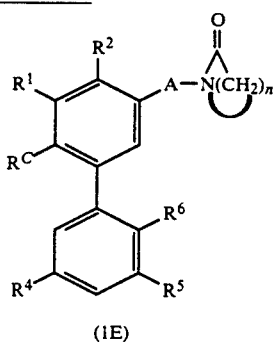

(1E)

[where $R^1$, $R^2$, $R^4$, $R^5$, $R^6$, $R^C$, A and $X_2$ are the same meanings as mentioned above. $R^{54}$ is a hydrogen atom or lower alkyl group. The letter n is 3 or 4.]

The reaction between compounds (1D) and (42) can be performed in the same conditions as in the reaction between compounds (11) and (24) of aforementioned reaction formula-13. The obtained intermediate is applicable in cyclization without isolating. The cyclization can be performed in solvents such as benzene, toluene, xylene and other aromatic hydrocarbons generally at room temperature to 200° C., preferably at room temperature to approximately 150° C. in about 1 to 15 hours.

Reaction formula-23

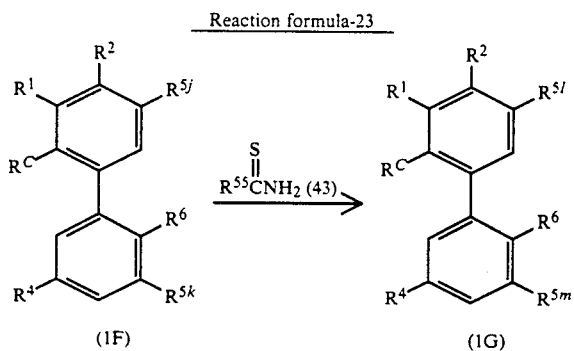

[where $R^1$, $R^2$, $R^C$, $R^4$, $R^6$ and $X_2$ are the same meanings as mentioned above. $R^{55}$ is a lower alkyl group. $R^{5j}$ and $R^{5k}$ are equal to aforementioned $R^5$. However, at least one of $R^{5j}$ and $R^{5k}$ should be group:

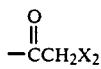

$R^{5l}$ and $R^{5m}$ are equal to aforementioned $R^5$. However, at least one of $R^{5l}$ and $R^{5m}$ should be group:

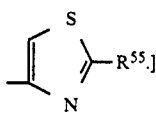

The reaction between compound (1F) and (1G) can be performed in the same solvent as in the reaction between components (1a) and (19) of reaction formula-2 generally at room temperature to 150° C., preferably at room temperature to 100° C. for approximately about 1 to 10 hours. At least equal molar ratio, preferaly equal to three times molar retio of compound (43) should be used to compound (1F).

Reaction formula-24

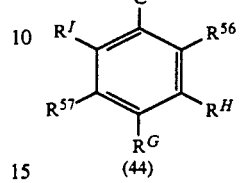

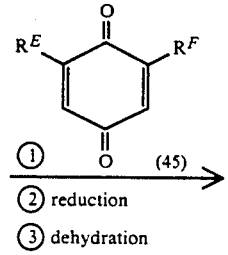

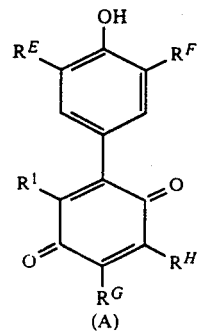

[where A, $R^H$, $R^G$, $R^I$, $R^E$ and $R^F$ are the same meanings as mentioned above. $R^{56}$ and $R^{57}$ are lower alkoxy-lower alkoxy group.]

The reaction between compounds (44) and (45) can be performed in the same conditions as in the reaction between compounds (11) and (33) of aforementioned reaction formula-17.

Object materials thus obtained through the processes can be easily isolated and purified by general separating methods. As the separating methods, extraction by solvent, dilution, recrystallization, column-chromatography, preparative thin layer chromatography or the like can be listed, for example.

Compounds of the invention naturally include their stereo-isomers and optical isomers.

Phenyl derivatives shown by general formulas 1 to 4 and A of this invention can be led into acid-addition salts easily by activating pharmaceutically acceptable acid, and the acid-addition salts are also included in this invention. As aforementioned acid, inorganic acids such as hydrochloric acid, sulfuric acid, phosphoric acid and hydrobromic acid and organic acids such as acetic acid, oxalic acid, succinic acid, maleic acid, fumaric acid, malic acid, tartaric acid, citric acid, malonic acid, methansulfonic acid and benzoic acid can be listed, for example.

Out of phenyl derivatives shown by general formulas 1 to 4 A of this invention, those compounds which have acidic group can easily led salts by activating basic compound which are pharmaceutically acceptable. As example of the basic compound, sodium hydroxide, potassium hydroxide, calcium hydroxide, sodium carbonate and potassium hydrocarbonate can be listed.

Out of phenyl derivatives shown by general formula-1 of the invention, those compounds which have ammonium group can easily form salts together with halogen anions (chlorine anion, bromine anion, fluorine anion, iodine anion) which are pharmaceutically acceptable.

Compound of this invention can be generally used in the form of normal pharmaceutical preparation. Preparation are formulated by using generally used diluents or vehicles such as loading, filler, binding agent, humectant, disintegrator, surface activator and smoother. As pharmaceutical preparation, various forms can be chosen according to treating purposes, and representatively, tablets, pills, powders, liquids, suspensions, emulsions, granules, capsules, suppositories, injections (liquids, emulsions or the like) and ointments can be listed. In forming in shape of tablets, known carriers in this field may be widely used, and for example, vehicles such as lactose, white sugar, sodium chloride, glucose, urea, starch, calcium carbonate, kaoline, crystalline cellulose, silicic acid and other; binding agents such as water, ethanol, propanol, syrupus simplex, solution of glucose, solution of starch, gelatine solution, carboxymethyl cellulose, shellac, methyl cellulose, potassium phosphate, polyvinylpyrrolidone; disintegrator such as dried starch, sodium alginate, agar powder, laminarin powder, calcium carbonate, polyoxyethylene sorbitane, aliphatic esters, sodium laurylhydrosulfate, monoglyceride stearate, starch and lactose, disintegration inhibiting agents such as white sugar, stearine, cacao butter, hydrogenated oil; absorption accelerators such as quaternary ammonium salt and sodium laurylsulfate; humectants such as glycerine and starch, absorbents such as starch, lactose, kaoline, bentonite and colloidal silicic acid; and smoothers such as purified talc, stearate, powdery boric acid and polyethylene glycol. Moreover, when required, general drug coating can be applied to tablets to form sugar-coated tablets, gelatin-coated tablets, enteric-coated tablets, film-coated tablets, double layer tablets or multilayer tablets. In forming the shape of pills, conventionally known carriers in the field can be widely used, and are, for example, vehicles such as glucose, lactose, starch, cacao oil, hardened vegetable oil, kaoline, talc; binding agents such as powdery gum arabic, powdery tragacanth gum, gelatin and ethanol, solubilizers such as laminarin agar; and the like. In forming suppositories, conventionally known carriers can be widely used, and are, for example, polyethylene glycol, cacao oil, higher alcohols, esters of higher alcohols, gelatin and semi-synthetic glyceride. In formulating into injections, it is preferable that liquids, emulsions and suspensions should be sterilized and isotonic with human blood. In formulation of the liquids, emulsions and suspensions, any diluting agent generally used in this field can be used such as water, aqueous solution of lactic acid, ethyl alcohol, propylene glycol, ethoxylated isostearyl alcohol, polyoxide, isostesryl alcohol, polyoxyethylene sorbitan aliphatic acid ester. In this case, sufficient amount of sodium chloride, glucose or glycerin may be contained in the preparation to formulate isotonic solution, and also general dissolution adjuvant, buffer, soothing agent or the like may be added. Moreover, it is also possible to contain coloring agent, conservative, perfume, flavoring, sweetening and other medicine in the preparation when required. In formulating in paste, cream and gel, generally known dilutants in the field can be widely used such as white vaseline, paraffine, glycerin, cellulose derivatives, polyethylene glycol, silicone, bentonite.

The content of compound shown by general formulas 1 to 4 or A, or its salt of this invention to be contained in the preparation is not specifically limited and chosen in wide range appropriately, but generally it is preferable to contain 1 to 70% by weight in the preparation.

Administration method of the preparation is not specifically limited, and they are administered by appropriate method according to the form of the medicine, patient's age, sex and other conditions, degree of decease or the like. For example, tablets, pills, liquids, suspensions, emulsions, granules and capsules are administered orally. Injections are intravenously administered at independently or mixed with general supplemental fluids such as glucose and amino acid, and moreover, when necessary, they are independently administered intramuscularly, intracutaneously, subcutaneously or intraperitoneally. Suppositories are administered intrarectally.

The dose of the pharmaceutical preparation is selected properly according to use, patient's age, sex and other conditions, degree of the decease or the like, and generally it is proper to apply approximately 0.2 to 200 mg daily per 1 kg of body weight of compound shown by general formula 1 to 4 or A which are active ingredients.

EXAMPLES

Reference example 1

Figure 1:
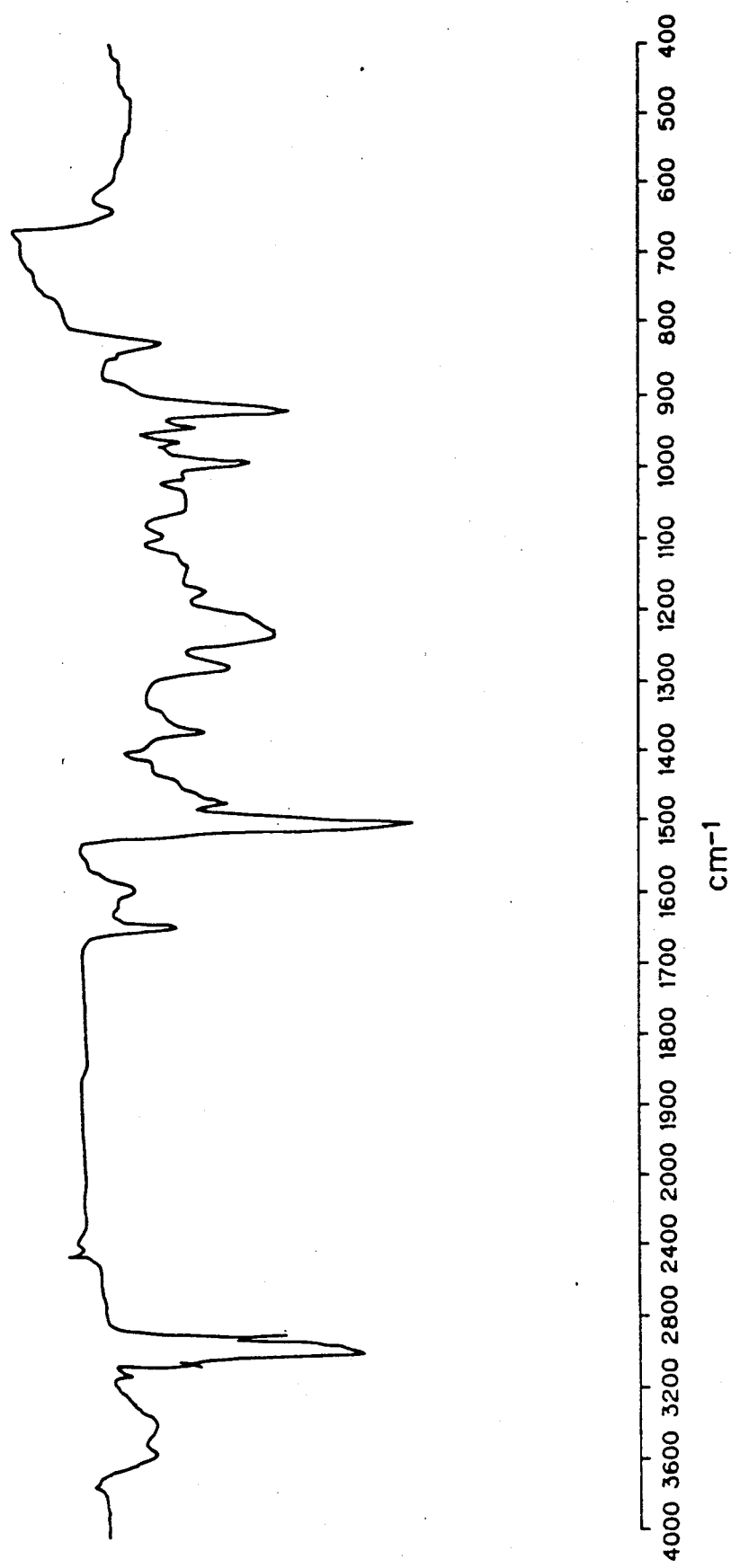
FIGS. 1 and 3 are IR spectra of compounds of this invention.

A solution was prepared by dissolving 105 g of 4-ethylphenol into 500 ml of chloroform. The solution was cooled by ice water bath, followed by dropwise addition of 45 ml of bromine while stirring. The addition was took 1 hour. Then, the reaction mixture was cooled by an ice water bath while stirring for 4 hours, moved into a separatory funnel to wash with water, an aqueous solution saturated with NaCl, 10% water solution of sodium hydrogencarbonate and an aqueous solution saturated with NaCl in turn, and dried with magnesium sulfate anhydride. The solvent in the reactant was distilled off under reduced pressure to yield 173 g of light brown and oily 2-bromo-4-ethylphenol.

NMR (CDCl$_3$) δ: 1.20 (3H, t, J=7.5 Hz); 2.56 (2H, q, J=7.5 Hz), 5.33 (1H, s), 6.92 (1H, d, J=8.0 Hz), 7.04 (1H, dd, J=8.0 Hz, 2.5 Hz), 7.28 (1H, d, J=2.5 Hz).

REFERENCE EXAMPLE 2

A solution was prepared by dissolving 200 g of 2-bromo-4-ethylphenol into 1 liter of 10% water solution of sodium hydroxide. 200 ml of dimethyl sulfate was dropwise added into the solution while stirring at room temperature. The addition was took 3 hours. The reaction mixture was stirred overnight and extracted with dichloromethane. The extract was washed with saturated salt water, dried with magnesium sulfate anhydride, and the solvent remaining in the reaction mixture was removed under reduced pressure. The residue was purified by a vacuum distillation to yield 180 g colorless and oily 2-bromo-4-ethylanisole having a b.p. of 130° C. 4 mmHg).

NMR (CDCl$_3$) δ: 1.20 (3H, t, J=7.5 Hz), 2.57 (2H, q, J=7.5 Hz), 3.87 (3H, s), 6.82 (1H, d, J=8.0 Hz), 7.08 (1H, dd, J=8.0 Hz, 2.5 Hz), 7.38 (1H, d, J=2.5 Hz).

REFERENCE EXAMPLE 3

A solution was prepared by dissolving 14 g of 4-methylthiophenol into 200 ml of chloroform. 5.5 ml of bromine was dropwise added into the solution, and stirred overnight at room temperature. The reaction mixture was washed by water, 10% water solution of sodium hydrogencarbonate and saturated salt water in turn, dried with magnesium sulfate anhydride and concentrated to yield 4-methyl-thio-2-bromophenol.

4-methylthio-2-bromophenol thus obtained was dissolved into 50 ml of dichloromethane and added 20 ml of N, N-diisopropyl-ethylamine thereinto, followed by dropwise addition of 9 ml of chloromethylmethylether with stirring while cooling with ice water bath. The reaction mixture was stirred overnight at room temperature, the solvent in the reaction mixture was distilled away under reduced pressure. Water was added into the distillation residue, the mixture was extracted with diethylether. The extract was washed with 10% water solution of sodium hydroxide and saturated salt water, dried with sodium sulfate and concentrated to yield 23.6 g of 3-bromo-4-methoxymethoxy-thioanisole.

NMR (CDCl$_3$) δ: 2.45 (3H, s), 3.51 (3H, s), 5.21 (2H, s), 7.07 (1H, d, J=8.5 Hz), 7.18 (1H, dd, J=8.5 Hz, 2.0 Hz), 7.48 (1H, d, J=2.0 Hz).

EXAMPLE 1

A mixture was prepared by suspending 7.2 g of metallic magnesium into 40 ml of tetrahydrofuran (THF). The mixture, wherein 1 ml of 2-bromo-4-ethylanisole was added, was stirred at room temperature. After an exothermic reaction occurred, the reaction mixture was diluted with 100 ml of THF, followed by dropwise addition of the solution which was prepared by dissolving 63.5 g of 2-bromo-4-ethylanisole into 160 ml of THF. The addition was took 2 hours. The reaction mixture was stirred for 1 hour, refluxed by heating for further 1 hour and cooled down to 0° C. in internal temperature, wherein 59 g of p-bromoanisole was added thereinto, 0.5 g power of the complex compound of nickel chloride and 1,3-diphenylphosphynopropane (Nidppp Cl$_2$) was added in the reaction mixture, and stirred overnight. The reactant was transferred into ammonium chloride water solution and extracted with diethylether. The extract was washed with an aqueous solution saturated with NaCl, dried with sodium sulfate and concentrated. The concentrate was distilled under reduced pressure to yield 51.6 g of 5-ethyl-2,4'-dimethoxy-biphenyl having a b.p. of 135°–148° C. (0.5 mmHg).

NMR (CDCl$_3$) δ: 1.24 (3H, t, J=7.5 Hz), 2.63 (2H, q, J=7.5 Hz), 3.78 (3H, s), 3.84 (3H, s), 6.89 (1H, d, J=8.5 Hz), 6.95 (2H, d, J=9.0 Hz), 7.05–7.15 (2H, m), 7.47 (2H, d, J=9.0 Hz).

EXAMPLE 2

A mixture was prepared by suspending 0.75 g of metallic magnesium into 20 ml of THF. The mixture, wherein 7.9 g of 3-bromo-4-methoxythioanisole was added, was refluxed by heating until magnesium in the reaction mixture disappears. The reaction mixture was cooled with ice, 7.0 g of 4-methoxybromobenzene was added thereinto and 0.2 g of Nidppp Cl$_2$ were added thereinto. The reaction mixture was stirred overnight in room temperature, ammonium chloride water solution was added thereinto and then extracted with diethylether. The extract was washed with an aqueous solution saturated with NaCl, dried by sodium sulfate and concentrated. The concentrate was purified by a silica gel column-chromatography (n-hexane:ethylacetate=20:1) to yield 6.1 g of 2,4'-bis(methoxymethoxy)-5-methylthio biphenyl.

NMR (CDCl$_3$) δ: 2.47 (3H, s), 3.39 (3H, s), 3.51 (3H, s), 5.08 (2H, s), 5.21 (2H, s), 7.00–7.26 (4H, m), 7.45 (2H, d, J=9.0 Hz).

In a manner analogous to that described in Examples 1 and 2 hereinabove, the compounds, which are obtained from those of pertinent starting materials, were listed in the following Table 1.

TABLE 1

[Structure: biphenyl with R1, R2, R3 on one ring and R4, R5, R6 on the other ring]

| Example | R¹ | R² | R³ | R⁴ | R⁵ | R⁶ | Crystal form (Solvent for recristallization) | Melting point (°C.) (salt) |
|---|---|---|---|---|---|---|---|---|
| 3 | H | OH | H | H | H | OH | White powder (methanol-H₂O) | 164-165 |
| 4 | H | OH | H | —C₂H₅ | H | OH | White powder (H₂O-n-hexan) | 109-111 |
| 5 | H | OH | H | —CH(CH₃)₂ | H | OH | Colorless needle (ethyl acetate-n-hexan) | 93-95 |
| 6 | H | OH | H | —C(CH₃)₃ | H | OH | NMR | |
| 7 | H | OH | H | —CH₂Ph | H | OH | White powder (n-hexan) | 107.5-108.0 |
| 8 | H | OH | H | —Ph | H | OH | Colorless needle (ethyl acetate-n-hexan) | 131-131.5 |
| 10 | H | OH | H | —OPh | H | OH | NMR | |
| 11 | H | OH | H | —SCH₃ | H | OH | White powder (dichloromethane-n-hexan) | 109-111 |
| 12 | —C₂H₅ | OH | H | —C₂H₅ | H | OH | Colorless needle (ethyl acetate-n-hexan) | 122-123 |
| 13 | —Ph | OH | H | —C₂H₅ | H | OH | White powder (n-hexan) | 104-105 |
| 14 | —F | OH | H | —C₂H₅ | H | OH | NMR | |
| 15 | —Br | OH | H | —C₂H₅ | H | OH | NMR | |
| 16 | —C(CH₃)₃ | OH | H | —C₂H₅ | H | OH | Colorless needle (chloroform-n-hexan) | 139-140 |
| 17 | —COCH₃ | OH | H | —COCH₃ | H | OH | Colorless needle (ethyl acetate-n-hexan) | 212-213 |
| 18 | —CH₂CH=CH₂ | OH | H | H | —CH₂CH=CH₂ | OH | White powder (n-hexan) | 51-52 |
| 19 | —C₃H₇ | OH | H | H | —C₃H₇ | OH | NMR | |
| 20 | —CH₂CH=CH₂ | OH | H | —C₂H₅ | —CH₂CH=CH₂ | OH | White powder (n-hexan) | 47-48 |
| 21 | —CH₂CH=CH₂ | OH | H | —Ph | —CH₂CH=CH₂ | OH | NMR | |

TABLE 1-continued

| | | | | | | |
|---|---|---|---|---|---|---|
| 22 | —CH₂CH=CH₂ | OH | H | —CH(CH₃)₂ | OH | NMR |
| 23 | —CH₂CH=CH₂ | OH | H | —CH₂Ph | OH | NMR |
| 24 | —CH₂CH=CH₂ | OH | H | —C(CH₃)₃ | OH | NMR |
| 25 | —CH₂CH=CH₂ | OH | H | —OCH₃ | OH | NMR |
| 26 | —CH₂CH=CH₂ | OH | H | —OPh | OH | NMR |
| 27 | —CH₂CH=CH₂ | OH | H | —SCH₃ | OH | NMR |
| 28 | —CH₂CH=CH₂ | OH | H | —SO₂CH₃ | OH | NMR |
| 29 | —CH₂CH=CH₂ | OH | H | —SOCH₃ | OH | White powder (ethyl acetate-n-hexan) 155.5-156.5 |
| 30 | cyclohexenyl | OH | —CH₂CH=CH₂ | H | OH | NMR |
| 31 | —CH₂CH=CH₂ | OH | —CH₂CH=CH₂ | H | OH | NMR |
| 32 | —CH₂CH=CH₂ | OH | —CH₂N(C₂H₅)₂ | H | OH | NMR |
| 33 | —CH₂CH=CH₂ | OH | —C(CH₃)₃ | —C₂H₅ | OH | Colorless needle (methanol-H₂O) 85-86 |
| 34 | —CH₂CH=CH₂ | OH | —CH₂CH=CH₂ | —CH₂CH=CH₂ | OH | NMR |
| 35 | —CH₂CH=CH₂ | OH | —CH₂CH=CH₂ | cyclohexenyl | OH | NMR |
| 36 | —C₃H₇ | OH | —C₃H₇ | —C₃H₇ | OH | NMR |
| 37 | —CH₂CH=CH₂ | OH | —C₂H₅ | —C₂H₅ | OH | NMR |
| 38 | —CH₂CH=CH₂ | OH | —C₃H₇ | —C₃H₇ | OH | NMR |
| 39 | —CH₂CH=CH₂ | OH | —CH₂CH=CH₂ | —C₃H₇ | OH | NMR |
| 40 | —CH₂CH=CH₂ | OH | —CH₂N(C₂H₅)₂ | —CH₂N(C₂H₅)₂ | OH | Colorless needle (ethanol-diethylether) 145 (Decomposition) (2HCl) |
| 41 | —CH₂CH=CH₂ | OH | —Br | —Br | OH | NMR |
| 42 | —CH₂CH=CH₂ | OH | —COCH₃ | —COCH₃ | OH | NMR |
| 43 | —CH₂CH=CH₂ | OH | F | —C₂H₅ | OH | Colorless needle (dichloromethane-n-hexan) 77-78 |
| 44 | —CH₂CH=CH₂ | OH | —CH₂N-pyrrolidinyl | —C₂H₅ | OH | Light-yellow powder (ethanol-diethylether) 105-108 (HCl) |

TABLE 1-continued

| | | | | | | | |
|---|---|---|---|---|---|---|---|
| 45 | —CH$_2$CH=CH$_2$ | OH | —CH$_2$N(pyrrolidine with CON(CH$_3$)$_2$) | —C$_2$H$_5$ | —CH$_2$CH=CH$_2$ | OH | Light-yellow powder (ethyl acetate-diisopropylether) | 145 (decomp.) (HCl) |
| 46 | —CH$_2$CH=CH$_2$ | OH | —Ph | —C$_2$H$_5$ | —CH$_2$CH=CH$_2$ | OH | NMR |
| 47 | —CH$_2$CH=CH$_2$ | OH | —Br | —C$_2$H$_5$ | —CH$_2$CH=CH$_2$ | OH | NMR |
| 48 | —CH$_2$CH=CH$_2$ | OH | —COCH$_3$ | —C$_2$H$_5$ | —CH$_2$CH=CH$_2$ | OH | NMR |
| 49 | —CH$_2$CH=CH$_2$ | OH | —COCH$_3$ | —CH(OCH$_3$)(CH$_3$) | —CH$_2$CH=CH$_2$ | OH | NMR |
| 50 | —CH$_2$CH=CH$_2$ | OH | —C(CH$_3$)$_3$ | —C$_2$H$_5$ | —CH$_2$CH=CH$_2$ | OH | NMR |
| 51 | —CH$_2$CH=CH$_2$ | OH | —CH(NHCH$_3$)(CH$_3$) | —C$_2$H$_5$ | —CH$_2$CH=CH$_2$ | OH | NMR |
| 52 | —CH$_2$CH=CH$_2$ | OH | —CH(N(CH$_3$)(COCH$_3$))(CH$_3$) | —C$_2$H$_5$ | —CH$_2$CH=CH$_2$ | OH | NMR |
| 53 | —CH$_2$CH=CH$_2$ | OH | H | —C$_2$H$_5$ | H | OCH$_3$ | NMR |
| 54 | —CH$_2$CH=CH$_2$ | OH | H | —(CH$_2$)$_3$OH | H | OCH$_3$ | NMR |
| 55 | —CH$_2$CH=CH$_2$ | OCH$_3$ | H | —CH$_2$CH=CH$_2$ | H | OH | NMR |
| 56 | —CH$_2$CH=CH$_2$ | OH | H | —CH$_2$CH=CH$_2$ | H | OCH$_3$ | NMR |
| 57 | —CH$_2$CH=CH$_2$ | —O(CH$_2$)$_{10}$OH | H | —CH$_2$CH=CH$_2$ | H | OH | NMR |
| 58 | —CH$_2$CH=CH$_2$ | OH | H | —CH$_2$CH=CH$_2$ | H | —O(CH$_2$)$_{10}$OH | NMR |
| 59 | —CH$_2$CH=CH$_2$ | —O(CH$_2$)$_{10}$OH | H | —CH$_2$CH=CH$_2$ | H | —O(CH$_2$)$_{10}$OH | NMR |
| 60 | —CH$_2$CH=CH$_2$ | OH | (2,4-disubstituted phenol: C$_2$H$_5$, CH$_2$CH=CH$_2$, OH) | —C$_2$H$_5$ | —CH$_2$CH=CH$_2$ | OH | NMR |
| 61 | H | OH | H | —C$_2$H$_5$ | H | OH | White powder (methanol-H$_2$O) |
| 62 | H | —OCH$_2$CH=CH$_2$ | H | —C$_2$H$_5$ | H | —OCH$_2$CH=CH$_2$ | NMR | 109-111 |
| 63 | H | OH | H | —SCH$_3$ | H | OH | White powder | 109-111 |

TABLE 1-continued

| | | | | | Crystal form (Solvent for recristallization) |
|---|---|---|---|---|---|
| 64 | H | —OCH₂CH=CH₂ | —SCH₃ | H | (dichloromethane-n-hexan) NMR |
| 65 | —CH₂CH=CH₂ | —OCH₂CH=CH₂ | —CH₂CH=CH₂ | H | NMR |
| 66 | H | OH | —C₂H₅ | H | NMR |
| 67 | H | —OCH₂CH=CH₂ | —C₂H₅ | —COCH₃ | NMR |
| 68 | H | —OCH₂CH=CH₂ | $\begin{array}{c}CH_3\\|\\-CH\\|\\-OCH_3\end{array}$ | —COCH₃ | NMR |
| 69 | H | OH | —C₂H₅ | Br | NMR |
| 70 | Br | OH | —C₂H₅ | Br | NMR | structure: biphenyl with R¹⁹, R¹⁷, R¹⁶ on one ring and R⁹, R¹¹, R¹² on the other ring

| Example | R¹⁹ | R¹⁶ | R¹⁷ | R⁹ | R¹¹ | R¹² | Crystal form (Solvent for recristallization) |
|---|---|---|---|---|---|---|---|
| 71 | —CH₂CH=CH₂ | —CH₂CH=CH₂ | H | —CH₂CH=CH₂ | H | OH | NMR |
| 72 | —CH₂CH=CH₂ | OH | (3-cyclohexenyl-O—) | —CH₂CH=CH₂ | H | OH | NMR |
| 73 | —CH₂CH=CH₂ | —O(CH₂)₁₀OH | H | —CH₂CH=CH₂ | H | OH | NMR |
| 74 | —CH₂CH=CH₂ | OH | —CH₂CH=CH₂ | —CH₂CH=CH₂ | —CH₂CH=CH₂ | OH | NMR |
| 75 | —CH₂CH=CH₂ | —O(CH₂)₂OH | H | —CH₂CH=CH₂ | H | OH | NMR |
| 76 | —CH₂CH=CH₂ | —O(CH₂)₂N(C₂H₅)₂ | H | —CH₂CH=CH₂ | H | OH | NMR |
| 77 | —CH₂CH=CH₂ | —O(CH₂)₂SCH₃ | H | —CH₂CH=CH₂ | H | OH | NMR |
| 78 | —CH₂CH=CH₂ | bonding with R¹² —O—CH₂— —O—CH₂— | H | —CH₂CH=CH₂ | H | — | NMR |

TABLE 1-continued

| No. | | | | | |
|---|---|---|---|---|---|
| 79 | —CH$_2$CH=CH$_2$ | —O(CH$_2$)$_2$NHC$_2$H$_5$ | H | —CH$_2$CH=CH$_2$ | NMR |
| 80 | —CH$_2$CH=CH$_2$ | —O(CH$_2$)$_2$N(C$_2$H$_5$)(COCH$_3$) | H | —CH$_2$CH=CH$_2$ | NMR |
| 81 | —CH$_2$CH=CH$_2$ | —O(CH$_2$)$_3$N(phthalimide) | H | —CH$_2$CH=CH$_2$ | NMR |
| 82 | —CH$_2$CH=CH$_2$ | —O(CH$_2$)$_4$COOC$_2$H$_5$ | H | —CH$_2$CH=CH$_2$ | NMR |
| 83 | —CH$_2$CH=CH$_2$ | —O(CH$_2$)$_{10}$—O(tetrahydropyranyl) | H | —CH$_2$CH=CH$_2$ | NMR |
| 84 | —CH$_2$CH=CH$_2$ | —O(CH$_2$)$_2$Cl | H | —CH$_2$CH=CH$_2$ | NMR |
| 85 | —CH$_2$CH=CH$_2$ | —O(CH$_2$)$_3$COOC$_2$H$_5$ | H | —CH$_2$CH=CH$_2$ | NMR |
| 86 | —CH$_2$CH=CH$_2$ | —O(CH$_2$)$_4$COOH | H | —CH$_2$CH=CH$_2$ | NMR |
| 87 | —CH$_2$CH=CH$_2$ | —O(CH$_2$)$_6$Br | H | —CH$_2$CH=CH$_2$ | NMR |
| 88 | —CH$_2$CH=CH$_2$ | —O(CH$_2$)$_6$OCOCH$_3$ | H | —CH$_2$CH=CH$_2$ | NMR |
| 89 | —CH$_2$CH=CH$_2$ | —O(CH$_2$)$_6$OH | H | —CH$_2$CH=CH$_2$ | NMR |
| 90 | —CH$_2$CH=CH$_2$ | —O(CH$_2$)$_6$—S—(3,5-di-tert-butyl-4-hydroxyphenyl) | H | —CH$_2$CH=CH$_2$ | NMR |
| 91 | —CH$_2$CH=CH$_2$ | —O(CH$_2$)$_6$—N(imidazolyl) | H | —CH$_2$CH=CH$_2$ | NMR |
| 92 | —CH$_2$CH=CH$_2$ | —O(CH$_2$)$_6$—N(pyrrolidinyl) | H | —CH$_2$CH=CH$_2$ | NMR |
| 93 | —CH$_2$CH=CH$_2$ | —O(CH$_2$)$_5$OH | H | —CH$_2$CH=CH$_2$ | NMR |

TABLE 1-continued

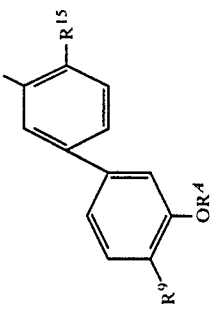

| Example | R⁹ | Rᴬ | R¹⁴ | R¹⁵ | Crystal form (Solvent for recristallization) |
|---|---|---|---|---|---|
| 94 | —CH₂CH=CH₂ | H | OH | —CH₂CH=CH₂ | NMR |

| Example | R⁹ | Rᴮ | R¹⁸ | R²¹ | R²² | R²³ | R²⁴ | Crystal form (Solvent for recristallization) | Melting point (°C.) (salt) |
|---|---|---|---|---|---|---|---|---|---|
| 95 | —CH₂CH=CH₂ | H | H | —CH₂CH=CH₂ | OH | H | H | White powder (n-hexan) | 78–79 |
| 96 | —CH₂CH=CH₂ | H | H | H | H | OH | —CH₂CH=CH₂ | White powder (isopropylether-n-hexan) | 73–74 |
| 97 | —CH₂CH=CH₂ | H | —CH₂CH=CH₂ | H | —CH₂CH=CH₂ | OH | —CH₂CH=CH₂ | NMR | |
| 98 | H | H | H | H | OH | H | H | White powder (diethyl ether-n-hexan) | 194–195 |
| 99 | H | —CH₂CH=CH₂ | H | H | —OCH₂CH=CH₂ | OH | H | NMR | |
| 100 | —CH₂CH=CH₂ | H | H | H | OH | —CH₂CH=CH₂ | H | NMR | |

NMR (CDCl$_3$) δ (ppm):

Compound of Example 6: 1.32 (9H, s, 5.01 (2H, bs), 6.91 (1H, d, J=8.5 Hz), 6.95 (2H, d, J=8.5 Hz), 7.21 (1H, d, J=2.5 Hz), 7.27 (1H, dd, J=8.5 Hz, 2.5 Hz), 7.36 (2H, d, J=8.5 Hz)

Compound of Example 10: 5.07 (1H, s), 5.14 (1H, s), 6.90–7.07 (8H, m), 7.24–7.35 (4H, m)

Compound of Example 14: 1.22 (3H, t, J=7.0 Hz), 2.61 (2H, q, J=7.0 Hz), 5.00 (1H, s), 5.39 (1H, d, J=4.0 Hz), 6.87 (1H, d, J=8.0 Hz), 7.00–7.26 (5H, m)

Compound of Example 15: 1.23 (3H, t, J=7.5 Hz), 2.60 (2H, q, J=7.5 Hz, 5.05 (1H, s), 5.67 (1H, s), 6.86 (1H, d, J=8.0 Hz), 7.00–7.15 (3H, m), 7.35 (1H, dd, J=8.5 Hz, 2.0 Hz), 7.16 (1H, d, J=2.0 Hz).

Compound of Example 19: 1.00 (6H, t, J=7.5 Hz), 1.60–1.75 (4H, m), 2.55–2.70 (4H, m), 4.90 (1H, s), 5.28 (1H, s), 6.85–7.20 (6H, m).

Compound of Example 21: 3.47 (2H, d, J=6.5 Hz), 3.52 (2H, d, J=6.5 Hz), 5.05–5.26 (4H, m), 5.13 (1H, s), 5.36 (1H, s), 5.96–6.20 (2H, m), 6.94 (1H, d, J=8.5 Hz, 7.20–7.47 (7H, m), 7.58 (2H, dd, J=8.5 Hz, 1.5 Hz).

Compound of Example 22: 1.24 (6H, d, J=7.0 hz), 2.85 (1H, sep, J=7.0 Hz), 3.44 (2H, d, J=6.0 Hz), 3.46 (2H, d, J=4.5 Hz), 5.05–5.25 (4H, m), 5.10 (1H, s), 5.17 (1H, s), 5.95–6.20 (2H, m) 6.85–7.00 (3H, m), 7.20–7.25 (2H, m).

Compound of Example 23: 3.41 (2H, d, J=7.0 Hz), 3.44 (2H, d, J=7.0 Hz), 3.91 (2H, s), 5.05–5.25 (4H, m) 5.06 (1H, s), 5.20 (1H, s), 5.95–6.15 (2H, m), 6.85–7.00 (3H, m), 7.15–7.30 (7H, m).

Compound of Example 24: 1.31 (9H, s), 3.46 (4H, d, J=5.5 Hz), 5.05–5.27 (4H, m), 5.08 (1H, s), 5.18 (1H, s), 5.95–6.15 (2H, m), 6.92 (1H, d, J=8.5 Hz), 7.05–7.15 (2H, m), 7.20–7.25 (2H, m).

Compound of Example 25: 3.43 (2H, d, J=7.0 Hz), 3.46 (2H, d, J=6.5 Hz), 3.77 (3H, s), 4.95 (1H, s), 5.05–5.25 (4H, m), 5.12 (1H, s), 5.95–6.12 (2H, m), 6.65 (1H, d, J=3.0 Hz) 6.70 (1H, d, J=3.0 Hz), 6.91 (1H, dd, J=7.0 Hz, 1.5 Hz), 7.20–7.26 (2H, m).

Compound of Example 26: 3.43 (2H, d, J=6.5 Hz), 3.45 (2H, d, J=4.0 Hz), 5.05–5.25 (4H, m), 5.14 (1H, s), 5.19 (1H, s), 5.93–6.10 (2H, m), 6.75–7.06 (6H, m), 7.19–7.33 (4H, m).

Compound of Example 27: 2.46 (3H, s), 3.43 (2H, d, J=8.0 Hz), 3.46 (2H, d, J=6.5 Hz), 5.09–5.26 (4H, m), 5.17 (1H, s), 5.25 (1H, s), 5.95–6.13 (2H, m), 6.92 (1H, d, J=8.5 Hz), 7.07 (1H, d, J=2.5 Hz), 7.10 (1H, d, J=2.5 Hz), 7.19–7.23 (2H, m).

Compound of Example 28: 3.06 (3H, s), 3.46 (2H, d, J=6.5 Hz), 3.49 (2H, d, J=7.0 Hz), 5.12–5.23 (4H, m), 5.65 (1H, s), 5.93 (1H, s), 5.95–6.11 (2H, m), 6.96 (1H, d, J=9.0 Hz), 7.15–7.20 (2H, m), 7.66–7.70 (2H, m).

Compound of Example 30: 1.40–2.20 (5H, m), 2.5–2.8 (1H, m), 3.35 (2H, d, J=6.5 Hz), 3.45 (2H, d, J=6.5 Hz), 3.55–3.65 (1H, m); 5.00–5.25 (4H, m), 5.17 (1H, s), 5.66 (1H, s), 5.80–6.10 (4H, m), 6.90 (1H, d, J=8.5 Hz), 7.00–7.20 (4H, m).

Compound of Example 31: 3.34 (2H, d, J=6.5 Hz), 3.45 (4H, d, J=6.5 Hz), 5.00–5.25 (6H, m), 5.16 (1H, s), 5.31 (1H, s), 5.85–6.15 (3H, m), 6.90 (1H, d, J=8.0 Hz), 7.00–7.40 (4H, m).

Compound of Example 32: 1.13 (6H, t, J=7.0 Hz), 2.65 (4H, q, J=7.0 Hz), 3.34 (2H, d, J=6.5 Hz), 3.43 (2H, d, J=6.5 Hz), 3.80 (2H, s), 5.00–5.15 (4H, m), 5.90–6.15 (2H, m), 6.85–7.15 (5H, m).

Compound of Example 34: 3.25 (2H, d, J=6.5 Hz), 3.30–3.40 (6H, m), 4.95–5.22 (10H, m), 5.80–6.06 (4H, m), 6.80–6.90 (2H, m), 7.00–7.05 (2H, m).

Compound of Example 35: 1.30–2.25 (10H, m), 2.5–2.9 (2H, m), 3.25–3.80 (6H, m), 5.00–5.25 (4H, m), 5.39 (1H, s), 5.65 (1H, s), 5.70–6.20 (6H, m), 7.00–7.20 (4H, m).

Compound of Example 36: 0.92–1.05 (12H, m), 1.60–1.80 (8H, m), 2.45–2.70 (8H, m), 4.74 (1H, s), 5.22 (1H, s), 6.85–7.15 (4H, m).

Compound of Example 37: 1.23 (3H, t, J<7.5 Hz), 1.25 (3H, t, J=7.5 Hz), 2.59 (2H, q, J=7.5 Hz), 2.68 (2H, q, J=7.5 Hz), 3.43 (2H, d, J=6.0 Hz), 3.46 (2H, d, J=6.0 Hz), 5.07–5.29 (4H, m), 5.11 (1H, s), 5.25 (1H, s), 5.95–6.15 (2H, m), 6.90–6.95 (2H, m), 7.06 (1H, d, J=2.5 Hz), 7.14 (1H, d, J=2.0 Hz).

Compound of Example 38: 0.95 (3H, t, J=7.5 Hz), 0.99 (3H, t, J=7.5 Hz), 1.55–1.65 (4H, m), 2.52 (2H, t, J=7.5 Hz), 2.62 (2H, t, J=7.5 Hz), 3.43 (2H, d, J=6.5 Hz), 3.46 (2H, d, J=6.5 Hz), 5.05–5.30 (4H, m), 5.09 (1H, s), 5.25 (1H, s), 5.95–6.15 (2H, m), 6.85–6.95 (2H, m), 7.05–7.15 (2H, m).

Compound of Example 39: 0.99 (6H, t, J=7.5 Hz), 1.60–1.75 (4H, m), 2.62 (4H, t, J=7.5 Hz), 3.32 (2H, d, J=6.5 Hz), 3.45 (2H, d, J=6.5 Hz), 5.00–5.30 )4H, m), 5.10 (1H, s), 5.22 (1H, s), 5.90–6.10 (2H, m), 6.86 (1H, d, J=2.0 Hz), 7.00 (1H, d, J=2.5 Hz), 7.04 (1H, d, J=2.0 Hz), 7.10 (1H, d, J=2.5 Hz).

Compound of Example 41: 3.41 (2H, d, J=6.5 Hz), 3.48 (2H, d, J=6.5 Hz), 5.09–5.20 (4H, m), 5.20 (1H, s), 5.72 (1H, s), 5.91–6.08 (2H, m), 7.15 (1H, d, J=2.0 Hz), 7.19 (1H, d, J=2.5 Hz), 7.23 (1H, d, J=2.5 Hz), 7.44 (1H, d, J=2.0 Hz).

Compound of Example 42: 2.54 (3H, s), 2.62 (3H, s), 3.44 (2H, d, J=6.5 Hz), 3.52 (2H, d, J=6.5 Hz), 5.07–5.28 (4H, m), 5.89–6.20 (2H, m), 6.21 (1H, s), 7.44 (1H, d, J=1.5 Hz), 7.68–7.76 (3H, m), 12.63 (1H, s).

Compound of Example 46: 1.22 (3H, t, J=7.5 Hz), 2.58 (2H, q, J=7.5 Hz), 3.44 (2H, d, J=6.5 Hz), 3.51 (2H, d, J=6.5 Hz), 5.05–5.26 (4H, m), 5.25 (1H, s), 5.44 (1H, s), 5.95–6.15 (2H, m), 6.94–6.96 (2H, m), 7.22–7.26 (2H, m), 7.40–7.60 (5H, m).

Compound of Example 47: 1.22 (3H, t, J=7.5 Hz), 2.58 (2H, q, J=7.5 Hz), 3.43 (2H, d, J=6.5 Hz), 3.48 (2H, d, J=6.5 Hz), 5.05–5.20 (4H, m), 5.08 (1H, s), 5.68 (1H, s), 5.92–6.13 (2H, m), 6.90 (1H, d, J=2.5 Hz), 6.95 (1H, d, J=2.0 Hz), 7.19 (1H, d, J=2.0 Hz), 7.47 (1H, d, J=2.5 Hz).

Compound of Example 48: 1.24 (3H, t, J=7.5 Hz), 2.61 (2H, q, J=7.5 Hz), 2.65 (3H, s), 3.45 (2H, d, J=5.0 Hz) 3.47 (2H, d, J=8.5 Hz), 4.89 (1H, s), 5.00–5.23 (4H, m), 5.94–6.15 (2H, m) 6.93 (1H, d, J=2.0 Hz), 7.00 (1H, d, J=2.0 Hz), 7.48 (1H, d, J=2.0 Hz), 7.73 (1H, d, J=2.0 Hz), 12.65 (1H, s).

Compound of Example 49: 1.45 (3H, d, J=6.5 Hz), 2.66 (3H, s), 3.26 (3H, s), 3.48 (4H, d, J=7.5 Hz), 4.26 (1H, q, J=6.5 Hz), 5.04–5.24 (4H, m), 5.19 (1H, s), 5.94–6.14 (2H, m), 7.05 (1H, d, J=2.0 Hz), 7.09 (1H, d, J=2.0 Hz), 7.48 (1H, d, J=2.0 Hz), 7.73 (1H, d, J=2.0 Hz), 12.70 (1H, s).

Compound of Example 50: 1.23 (3H, t, J=7.5 Hz), 1.42 (9H, s), 2.59 (2H, q, J=7.5 Hz), 3.40–3.50 (4H, m), 5.05–5.35 (4H, m), 5.25 (1H, s), 5.33 (1H, s), 5.95–6.15 (2H, m), 6.92–6.95 (2H, m), 7.07 (1H, d, J=2.0 Hz), 7.26 (1H, d, J=2.0 Hz).

Compound of Example 51: 1.22 (3H, t, J=7.5 Hz), 1.46 (3H, d, J=6.5 Hz), 2.44 (3H, s), 2.58 (2H, q, J=7.5 Hz) 3.40–3.50 (4H, m), 3.85 (1H, q, J=6.5 Hz), 5.00–5.20 (4H, m), 5.95–6.20 (2H, m), 6.90–6.95 (3H, m), 7.10 (1H, d, J=2.0 Hz).

Compound of Example 52: 1.23 (3H, t, J=7.5 Hz), 1.56 (3H, d, J=7.0 Hz), 2.14 (3H, s), 2.60 (2H, q, J=7.5 Hz) 2.87 (3H, s), 3.35-3.55 (4H, m), 5.00-5.20 (5H, m), 5.90-6.15 (3H, m), 6.90 (1H, d, J=2.0 Hz), 6.95 (1H, d, J=2.0 Hz), 7.10-7.20 (2H, m), 9.54 (1H, s).

Compound of Example 53: 1.24 (3H, t, J=7.5 Hz), 2.63 (2H, q, J=7.5 Hz), 3.46 (2H, d, J=6.5 Hz), 3.78 (3H, s) 4.98 (1H, s), 5.10-5.28 (2H, m), 6.00-6.20 (1H, m), 6.80-7.35 (6H, m).

Compound of Example 54: 1.85-1.96 (2H, m), 2.70 (2H, t, J=7.5 Hz), 3.46 (2H, d, J=6.5 Hz), 3.78 (2H, t, J=6.5 Hz), 5.10-5.25 (3H, m), 5.98-6.15 (1H, m), 6.80-7.33 (6H, m).

Compound of Example 55: 3.34 (2H, m), 3.45 (2H, m), (3H, s), 5.04 (2H, m), 5.16 (2H, m), 6.01 (2H, m), 6.90-7.26 (6H, m).

Compound of Example 56: 3.35 (2H, d, J=6.5 Hz), 3.45 (2H, d, J=6.5 Hz), 3.78 (3H, s), 4.98 (2H, m), 5.15 (2H, m), 6.02 (2H, m), 6.63 (1H, d, J=8.0 Hz), 6.95 (1H, d, J=8.0 Hz), 7.17 (2H, m), 7.25 (2H, m).

Compound of Example 57: 1.20-1.90 (16H, m), 3.35 (2H, d, J=7.0 Hz), 3.43 (2H, d, J=6.5 Hz) 3.64 (2H, t, J=6.5 Hz), 4.01 (2H, t, J=7.0 Hz), 5.00-5.25 (5H, m), 5.90-6.10 (2H, m), 6.90-7.25 (6H, m).

Compound of Example 58: 1.20-1.75 (16H, m), 3.36 (2H, d, J=6.5 Hz), 3.44 (2H, d, J=6.0 Hz), 3.70 (2H, t, J=6.5 Hz), 3.92 (2H, t, J=6.0 Hz), 5.00-5.20 (4H, m), 5.75-6.15 (3H, m), 6.83 (1H, d, J=8.0 Hz), 6.87 (1H, d, J=8.5 Hz), 7.00-7.15 (2H, m), 7.30-7.35 (2H, m).

Compound of Example 59: 1.20-1.90 (32H, m), 3.36 (3H, d, J=6.5 Hz), 3.42 (2H, d, J=6.5 Hz), 3.63 (2H, t, J=6.5 Hz), 3.64 (2H, t, J=6.5 Hz), 3.91 (2H, t, J=6.5 Hz), 3.99 (2H, t, J=6.5 Hz), 5.00-5.20 (4H, m), 5.90-6.10 (2H, m), 6.80-6.90 (2H, m), 7.00-7.15 (2H, m), 7.30-7.40 (2H, m).

Compound of Example 60: 1.22 (6H, t, J=7.5 Hz), 2.53-2.67 (4H, m), 3.40-3.55 (6H, m), 5.00-5.20 (6H, m), 5.24 (1H, s), 5.42 (1H, s), 5.74 (1H, s), 6.00-6.20 (3H, m) 6.90-7.10 (4H, m), 7.25-7.35 (2H, m).

Compound of Example 62: 1.24 (3H, t, J=7.5 Hz), 2.63 (2H, q, J=7.5 Hz), 4.50 (2H, dt, J=5.0 Hz, 2.0 Hz) 4.58 (2H, dt, J=5.5 Hz, 1.5 Hz), 5.15-5.48 (4H, m), 5.90-6.11 (2H, m), 6.88 (1H, d, J=8.5 Hz), 6.95 (2H, d, J=9.0 Hz), 7.06 (1H, dd, J=8.5 Hz, 2.5 Hz), 7.15 (1H, d, J=2.5 Hz), 7.49 (2H, d, J=9.0 Hz).

Compound of Example 64: 2.47 (3H, s), 4.51 (2H, dt, J=5.0 Hz, 1.5 Hz), 4.58 (2H, dt, J=5.5 Hz, 1.5 Hz), 5.15-5.50 (4H, m), 5.91-6.15 (2H, m), 6.90 (1H, d, J=8.5 Hz), 6.96 (2H, d, J=9.0 Hz), 7.21 (1H, dd, J=8.5 Hz, 2.5 Hz), 7.29 (1H, d, J=2.5 Hz), 7.47 (2H, d, J=9.0 Hz).

Compound of Example 65: 3.36 (2H, d, J=6.5 Hz), 3.45 (2H, d, J=6.5 Hz), 4.49 (2H, dt, J=5.0 Hz, 1.5 Hz), 4.58 (2H, dt, J=5.0 Hz, 1.5 Hz), 5.01-5.50 (8H, m), 5.89-6.17 (4H, m), 6.85-7.20 (4H, m), 7.34-7.38 (2H, m).

Compound of Example 66: 1.26 (3H, t, J=7.5 Hz), 2.64 (2H, q, J=7.5 Hz), 2.65 (3H, s), 3.80 (3H, s), 6.92 (1H, d, J=8.5 Hz), 7.02 (1H, d, J=8.5 Hz), 7.10-7.19 (2H, m), 7.65 (1H, dd, J=8.5 Hz, 2.0 Hz), 7.89 (1H, d, J=2.0 Hz), 12.26 (1H, s).

Compound of Example 67: 1.24 (3H, t, J=7.5 Hz), 2.62 (2H, q, J=7.5 Hz), 2.67 (3H, s), 4.49-4.53 (2H, m) 4.65-4.70 (2H, m), 5.17-5.50 (4H, m), 5.90-6.19 (2H, m), 6.88 (1H, d, J=8.5 Hz) 6.98 (1H, d, J=8.5 Hz), 7.09 (1H, dd, J=8.5 Hz, 2.5 Hz), 7.16 (1H, d, J=2.0 Hz) 7.70 (1H, dd, J=8.5 Hz, 2.5 Hz), 7.97 (1H, d, J=2.5 Hz).

Compound of Example 68: 1.44 (3H, d, J=6.5 Hz), 2.67 (3H, s), 3,23 (3H, s), 4.28 (1H, q, J=6.5 Hz) 4.50-4.55 (2H, m), 4.65-4.70 (2H, m), 5.15-5.55 (4H, m), 5.95-6.20 (2H, m) 6.95-7.05 (2H, m), 7.20-7.25 (2H, m), 7.70 (1H, dd, J=8.5 Hz, 2.5 Hz), 7.94 (1H, d, J=2.5 Hz).

Compound of Example 69: 1.21 (3H, t, J=7.5 Hz), 2.58 (2H, q, J=7.5 Hz), 5.56 (2H, bs), 6.88 (2H, d, J=8.5 Hz) 7.02 (1H, d, J=2.5 Hz), 7.27 (1H, d, J=2.5 Hz), 7.39 (2H, dd, J=8.5 Hz).

Compound of Example 70: 1.22 (3H, t, J=7.5 Hz), 2.58 (2H, q, J=7.5 Hz), 5.55 (1H, s), 5.65 (1H, s), 7.02 (1H, d, J=2.0 Hz), 7.06 (1H, d, J=8.5 Hz), 7.28 (1H, d, J=2.0 Hz), 7.39 (1H, dd, J=8.5 Hz, 2.0 Hz), 7.66 (1H, d, J=2.0 Hz).

Compound of Example 71: 1.50-2.25 (6H, m), 3.35-3.45 (4H, m), 4.55-4.65 (1H, m), 5.03-5.15 (4H, m) 5.70-5.80 (1H, m), 5.85-6.09 (3H, m), 6.90-7.20 (6H, m).

Compound of Example 72: 1.50-1.85 (4H, m), 2.00-2.20 (2H, m), 3.30-3.40 (4H, m), 3.65-3.80 (1H, m), 5.03-5.14 (4H, m), 5.56 (1H, s), 5.70 (1H, s), 5.80-6.04 (4H, m), 6.90-7.15 (5H, m).

Compound of Example 73: 1.15-1.80 (16H, m), 3.30-3.45 (4H, m), 3.63 (2H, t, J=6.5 Hz), 4.01 (2H, t, J=6.5 Hz), 5.00-5.15 (4H, m), 5.85-6.10 (2H, m), 6.59 (1H, s) 6.90-7.20 (6H, m).

Compound of Example 74: 3.34 (4H, d, J=6.5 Hz), 3.45 (4H, d, J=6.5 Hz), 5.00-5.20 (8H, m), 5.37 (2H, s) 5.85-6.15 (4H, m), 6.94 (2H, d, J=2.0 Hz), 7.00 (2H, d, J=2.0 Hz).

Compound of Example 75: 3.30-3.45 (4H, m), 3.78 (2H, t, J=4.5 Hz), 4.09 (2H, t, J=4.5 Hz), 5.00-5.15 (4H, m), 5.85-6.05 (2H, m), 6.75-7.20 (7H, m).

Compound of Example 76: 1.02 (6H, t, J=7.0 Hz), 2.62 (4H, q, J=7.0 Hz), 2.76 (2H, t, J=5.0 Hz) 3.37 (4H, d, J=7.0 Hz), 4.13 (2H, t, J=5.0 Hz), 5.00-5.15 (4H, m), 5.30 (1H, s), 5.90-6.10 (2H, m), 6.85-7.20 (6H, m).

Compound of Example 77: 2.04 (3H, s), 2.79 (2H, t, J=6.5 Hz), 3.30-3.45 (4H, m), 4.17 (2H, t, J=6.5 Hz) 5.00-5.15 (4H, m), 5.85-6.08 (2H, m), 6.22 (1H, s), 6.90-7.20 (6H, m).

Compound of Example 78: 3.41 (4H, d, J=7.0 Hz), 4.00-4.15 (2H, m), 4.30-4.50 (2H, m), 5.00-5.20 (4H, m), 5.90-6.10 (2H, m), 7.00-7.20 (6H, m).

Compound of Example 79: 1.10 (3H, t, J=7.0 Hz), 2.64 (2H, q, J=7.0 Hz), 2.92 (2H, t, J=5.0 Hz), 3.37 (4H, d, J=6.5 Hz), 4.14 (2H, t, J=5.0 Hz), 5.00-5.15 (4H, m), 5.90-6.10 (2H, m), 6.85-7.15 (6H, m).

Compound of Example 80: 0.97 (3H, t, J=7.0 Hz), 2.02 (3H, s), 3.12 (2H, q, J=7.0 Hz), 3.30-3.50 (4H, m) 3.59 (2H, t, J=5.0 Hz), 4.18 (2H, t, J=5.0 Hz), 5.00-5.15 (4H, m), 5.90-6.06 (3H, m), 6.85-7.20 (6H, m).

Compound of Example 81: 2.00-2.15 (2H, m), 3.30-3.45 (4H, m), 3.84 (2H, t, J=6.5 Hz), 4.01 (2H, t, J=6.0 Hz), 5.00-5.15 (4H, m), 5.90-6.10 (2H, m), 6.40 (1H, s), 6.90-7.20 (6H, m), 7.65-7.85 (4H, m).

Compound of Example 82: 1.23 (3H, t, J=7.5 Hz), 1.60-1.80 (4H, m), 2.31 (2H, t, J=7.0 Hz), 3.35-3.40 (4H, m) 4.02 (2H, t, J=6.5 Hz), 5.00-5.13 (5H, m), 5.85-6.05 (2H, m), 6.90-7.19 (6H, m).

Compound of Example 83: 1.15-1.95 (24H, m), 3.25-3.50 (6H, m), 3.65-3.93 (2H, m), 4.01 (2H, t, J=6.5 Hz) 4.58 (1H, t, J=5.0 Hz), 5.00-5.15 (4H, m), 5.90-6.10 (2H, m), 6.58 (1H, s), 6.90-7.20 (6H, m).

Compound of Example 84: 3.30-3.45 (4H, m), 3.70 (2H, t, J=6.0 Hz), 4.23 (2H, t, J=6.0 Hz), 5.00-5.15 (4H, m), 5.85-6.05 (2H, m), 6.07 (1H, s), 6.95-7.21 (6H, m).

Compound of Example 85: 1.23 (3H, t, J=7.0 Hz), 2.00-2.10 (2H, m), 2.37 (2H, t, J=7.5 Hz), 3.30-3.40

(4H, m) 4.00-4.15 (4H, m), 5.00-5.15 (4H, m), 5.88-6.09 (2H, m), 6.23 (1H, s), 6.85-7.20 (6H, m).

Compound of Example 86: 1.60-1.85 (4H, m), 2.31 (2H, t, J=7.0 Hz), 3.30-3.40 (4H, m), 4.02 (2H, t, J=7.0 Hz), 5.00-5.14 (4H, m), 5.85-6.05 (2H, m), 6.91-7.19 (6H, m).

Compound of Example 87: 1.30-1.50 (4H, m), 1.70-1.90 (4H, m), 3.33 (2H, t, J=6.0 Hz), 3.35-3.45 (4H, m) 4.03 (2H, t, J=6.5 Hz), 5.00-5.15 (4H, m), 5.85-6.10 (2H, m), 6.48 (1H, s) 6.90-7.20 (6H, m).

Compound of Example 88: 1.25-1.80 (8H, m), 2.03 (3H, s), 3.35-3.45 (4H, m), 3.95-4.10 (4H, m) 5.00-5.15 (4H, m), 5.90-6.10 (2H, m), 6.51 (1H, s), 6.90-7.20 (6H, m).

Compound of Example 89: 1.20-1.80 (9H, m), 3.35-3.45 (4H, m), 3.55-3.65 (2H, m), 4.03 (2H, t, J=6.5 Hz) 5.00-5.15 (4H, m), 5.85-6.10 (2H, m), 6.58 (1H, s), 6.90-7.20 (6H, m).

Compound of Example 90: 1.30-1.80 (8H, m), 1.42 (18H, s), 2.77 (2H, t, J=7.0 Hz), 3.35-3.45 (4H, m), 4.01 (2H, t, J=6.5 Hz), 5.00-5.15 (4H, m), 5.18 (1H, s), 5.90-6.10 (2H, s), 6.52 (1H, s), 6.90-7.20 (6H, m), 7.21 (2H, s).

Compound of Example 91: 1.23-1.80 (8H, m), 3.30-3.45 (4H, m), 3.83 (2H, t, J=7.0 Hz), 4.01 (2H, t, J=6.0 Hz) 5.00-5.15 (4H, m), 5.85-6.10 (2H, m), 6.85-7.20 (8H, m), 7.14 (1H, s).

Compound of Example 92: 1.20-1.50 (4H, m), 1.65-1.95 (4H, m), 2.05-2.20 (4H, m), 2.85-3.50 (10H, m) 4.02 (2H, t, J=6.0 Hz), 5.00-5.15 (4H, m), 5.90-6.10 (2H, m), 6.90-7.20 (6H, m).

Compound of Example 93: 1.30-1.65 (5H, m), 1.70-1.79 (2H, m), 3.30-3.45 (4H, m), 3.55-3.62 (2H, m) 4.04 (2H, t, J=7.0 Hz), 5.03-5.13 (4H, m), 5.85-6.05 (2H, m), 6.54 (1H, s) 6.92-7.20 (6H, m).

Compound of Example 94: 3.45 (4H, d, J=6.5 Hz), 5.02 (2H, s), 5.15-5.30 (4H, m), 5.95-6.15 (2H, m) 7.03 (2H, d, J=1.5 Hz), 7.09 (2H, dd, J=8.0 Hz, 1.5 Hz), 7.16 (2H, d, J=8.0 Hz).

Compound of Example 97: 3.46 (8H, d, J=6.5 Hz), 5.10-5.25 (10H, m), 5.95-6.15 (4H, m), 7.18 (4H, s).

Compound of Example 99:
4.53-4.65 (4H, m), 5.27-5.52 (4H, m), 6.00-6.20 (2H, m), 6.87 (1H, m), 6.95-7.03 (2H, m), 7.08-7.18 (2H, m), 7.32 (1H, m), 7.47-7.57 (2H, m).

Compound of Example 100: 3.40-3.52 (4H, m), 5.10-5.27 (6H, m), 5.96-6.17 (2H, m), 6.86 (1H, m), 7.00-7.18 (3H, m), 7.30-7.40 (2H, m).

EXAMPLE 101

A solution was prepared by dissolving 43 g of 5-ethyl-2,4'-biphenyldiol into 200 ml of DMF. The solution, wherein 20 g of sodium hydride was added in small portions, was stirred at room temperature until generation of hydrogen gas stops, followed by dropwise addition of 50 ml of allyl-bromide thereinto, and stirred overnight at room temperature. The solvent in the reactant was distilled away under reduced pressure. Water was added to the residue to extract with diethylether. An organic part of the extract was washed with an aqueous solution saturated with NaCl, dried by sodium sulfate and concentrated. The concentrate was purified with a silica gel column-chromatography (n-hexane:ethylacetate=50:1) to yield 58.4 g of 2,4'-diallyloxy-5-ethylbiphenyl.

NMR (CDCl$_3$) δ: 1.24 (3H, t, J=7.5 Hz), 2.63 (2H, q, J=7.5 Hz), 4.50 (2H, dt, J=5.0 Hz, 2.0 Hz), 4.58 (2H, dt, J=5.5 Hz, 1.5 Hz), 5.15-5.48 (4H, m), 5.90-6.11 (2H, m), 6.88 (1H, d, J=8.5 Hz), 6.95 (2H, d, J=9.0 Hz), 7.06 (1H, dd, J=8.5 Hz, 2.5 Hz), 7.15 (1H, d, J=2.5 Hz), 7.49 (2H, d, J=9.0 Hz).

In a manner analogous to that described in Examples 101 hereinabove, the compounds, which are described in Examples 64, 65, 67, 68, 71 and 99, were obtained from those of pertinent starting materials.

EXAMPLE 102

A solution was prepared by dissolving 58.4 g of 2,4'-diallyloxy-5-ethylbiphenyl into 200 ml of tetrahydronaphthalene. The solution was heated at 200° C. with nitrogen gas blowing for 8 hours with stirring, cooled, extracted with 10% sodium hydroxide and washed with n-hexane. The extract, which was acidified with hydrochloric acid, was extracted with diethylether. The extract was washed with an aqueous solution saturated with NaCl, and 10% water solution of sodium hydrogencarbonate, dried with sodium sulfate and concentrated. The concentrate was purified by a silica gel column-chromatography (n-hexane:ethylacetate=15:1) and recrystallized from n-hexane to yield white powder 40 g of 3,3'-diallyl-5-ethyl-2,4'-biphenyldiol having a m.p. of 47°-48° C.

NMR (CDCl$_3$) δ (ppm): 1.22 (3H, t, J=7.5 Hz), 2.59 (2H, q, J=7.5 Hz), 3.43 (2H, d, J=5.0 Hz), 3.48 (2H, d, J=4.5 Hz), 5.05-5.25 (4H, m), 5.10 (1H, m), 5.17 (1H, s), 5.95-6.15 (2H, m), 6.85-7.00 (3H, m), 7.20-7.25 (2H, m).

In a manner analogous to that described in Example 102 hereinabove, the compounds, which were described in Examples 18, 21-32, 34, 35, 37-60, 72, 74, 94-97 and 100, were obtained from those of pertinent starting materials.

EXAMPLE 103

A solution was prepared by dissolving 0.16 g of 3,3'-diallyl-5-methylmercapto-2,4'-biphenyldiol into 5 ml of methanol. The solution was cooled with ice, 2 ml water solution of 0.2 g of sodium metaperiodate was added thereinto, was cooled by an ice bath for 4 hours while stirring. The precipitate produced therein was filtered off, and washed with chloroform. The filtrate and the washing were mixed together, and water was added thereinto to extract with chloroform. The organic layer of the extract was washed twice with water and once with an aqueous solution saturated with NaCl, dried with sodium sulfate and concentrated. The concentrate was recrystallized from ethyl acetate/n-hexane to yield 0.1 g of white powder 3,3'-diallyl-5-methylsulfinyl-2,4'-biphenyldiol having a m.p. of 155.5°-156.5° C.

In a manner analogous to that described in Example 103 hereinabove, the compound, which is described in Example 28, was obtained from those of pertinent starting materials.

EXAMPLE 104

A solution was prepared by dissolving 0.62 g of 5-ethyl-2,4'-biphenyldiol into 20 ml of chloroform. The solution was cooled with ice, followed by dropwise addition of 0.48 g of bromine and stirred for 1 hour at the same temperature. The reaction mixture was washed with water, 10% water solution of sodium hydrogencarbonate and an aqueous solution saturated with NaCl in turn, dried with sodium sulfate and concentrated. The concentrate was separated by a silica gel column-chromatography (n-hexane:ethyl acetate=5:1) to yield 0.25 g of 3,3'-dibromo-5-ethyl-2,4'-biphenyldiol (I) from the first fraction, 0.12 g of 3-bromo-5-ethyl- 2,4'-biphenyldiol (II) from the 2nd fraction and 0.12 g of 3'-bromo-5-ethyl-2,4'-biphenyldiol (III) from the 3rd fraction.

(I) NMR (CDCl₃) δ: 1.22 (3H, t, J=7.5 Hz), 2.58 (2H, q, J=7.5 Hz), 5.55 (1H, s), 5.65 (1H, s), 7.02 (1H, d, J=2.0 Hz), 7.06 (1H, d, J=8.5 Hz), 7.28 (1H, d, J=2.0 Hz), 7.39 (1H, dd, J=8.5 Hz, 2.0 Hz), 7.66 (1H, d, J=2.0 Hz).

(II) NMR (CDCl₃) δ: 1.21 (3H, t, J=7.5 Hz), 2.58 (2H, q, J=7.5 Hz), 5.58 (2H, bs), 6.88 (2H, d, J=8.5 Hz), 7.02 (1H, d, J=2.5 Hz), 7.27 (1H, d, J=2.5 Hz), 7.39 (2H, d, J=8.5 Hz).

(III) NMR (CDCl₃) δ: 1.23 (3H, t, J=7.5 Hz), 2.60 (2H, q, J=7.5 Hz), 5.05 (1H, s), 5.67 (1H, s), 6.86 (1H, d, J=8.0 Hz), 7.00-7.15 (3H, m), 7.35 (1H, dd, J=8.5 Hz, 2.0 Hz), 7.61 (1H, d, J=2.0 Hz).

In a manner analogous to that described in Example 104 hereinabove, the compounds, which are described in Examples 14, 41, 43 and 47, were obtained from those of pertinent starting materials.

EXAMPLE 105

A mixture was prepared by suspending 5.0 g of aluminium chloride into 25 ml of 1,2-dichloroethane. The mixture was added 1.0 ml of acetylchloride, stirred for 1 hour at room temperature. The reaction mixture, wherein 2.4 g of 5-ethyl-2,4'-dimethoxybiphenyl was added, was stirred for 2 hours with cooling by the ice bath and stirred from further 2 hours at room temperature. Ice water was added into the reaction mixture, and extracted with chloroform. The extract was washed with 10% water solution of sodium hydrogencarbonate and an aqueous solution saturated with NaCl, dried with sodium sulfate and concentrated. The concentrate was purified by a silica gel column-chromatography (n-hexane:ethyl acetate=50:1) to yield 1.6 g of 3'-acetyl-5-ethyl-4'-hydroxy-2-methoxybiphenyl.

NMR (CDCl₃) δ: 1.26 (3H, t, J=7.5 Hz), 2.64 (2H, q, J=7.5 Hz), 2.65 (3H, s), 3.80 (3H, s), 6.92 (1H, d, J=8.5 Hz), 7.02 (1H, d, J=8.5 Hz), 7.10-7.19 (2H, m), 7.65 (1H, dd, J=8.5 Hz, 2.0 Hz), 7.89 (1H, d, J=2.0 Hz), 12.26 (1H, s).

In a manner analogous to that described in Example 105 hereinabove, the compounds, which are described in Example 17, 42, 48, 49, 67 and 68, were obtained from those of pertinent starting materials.

EXAMPLE 106

A solution was prepared by dissolving 0.10 g of 5'-acetyl-3,3'-diallyl-5-ethyl-2,4'-biphenyldiol into 2 ml of 40% metanol solution of methylamine. The solution was reflexed by heating for 3 hours, cooled, 0.2 g of sodium boron hydride was added thereinto, was reflexed by heating. The solution was added 0.2 g of sodium boron hydride and stirred from 1 hour at room temperature. The reaction mixture, wherein an excess of reagent was decomposed with hydrochloric acid, was neutralized with water solution of sodium hydrogencarbonate and extracted with diethylether. The extract was washed with an aqueous solution saturated with NaCl, dried with sodium sulfate and concentrated. The concentrate was purified by silica gel column-chromatography (dichloroethane:methanol=50:1) to yield 80 mg of 3,3'-diallyl-5-ethyl-5'-(1-methylaminoethyl)-2,4'-biphenyldiol.

NMR (CDCl₃) δ: 1.22 (3H, t, J=7.5 Hz), 1.46 (3H, d, J=6.5 Hz), 2.44 (3H, s), 2.56 (2H, q, J=7.5 Hz), 3.40-3.50 (4H, m), 3.85 (1H, q, J=6.5 Hz), 5.00-5.20 (4H, m), 5.95-6.20 (2H, m), 6.90-6.95 (3H, m), 7.10 (1H, d, J=2.0 Hz).

In a manner analogous to that described in Example 106 hereinabove, the compounds, which are described in Examples 32, 40, 44 and 45, were obtained from those of pertinent starting materials.

EXAMPLE 107

A solution was prepared by dissolving 50 mg of 3,3'-diallyl-5-ethyl-5'-(1-methylaminoethyl)-2,4'-biphenyldiol into 1 ml of ethanol. The solution, wherein 0.1 ml of acetic acid anhydride was added and stirred for 1 hour at room temperature. The reaction mixture was neutralized with solution of sodium hydrogencarbonate, and water was added thereinto and extracted with diethylether. The extract was washed with an aqueous solution saturated with NaCl, dried with sodium sulfate and concentrated. The concentrate was purified by a silica gel column-chromatography (n-hexane:ethyl acetate=3:1) to yield 40 mg of 5'-[1- (N-acetyl-N-methyl)ethyl]-3,3'-diallyl-5-ethyl-2,4'-biphenyldiol.

NMR (CDCl₃) δ: 1.23 (3H, t, J=7.5 Hz), 1.56 (3H, d, J=7.0 Hz), 2.14 (3H, s), 2.60 (2H, q, J=7.5 Hz), 2.87 (3H, s), 3.35-3.55 (4H, m) 5.00-5.20 (5H, m), 5.90-6.15 (3H, m), 6.90 (1H, d, J=2.0 Hz), 6.95 (1H, d, J=2.0 Hz), 7.10-7.20 (2H, m), 9.54 (1H, s).

In a manner analogous to that described in Example 107 hereinabove, the compound, which was described in Example 80, was obtained from those of pertinent starting materials.

EXAMPLE 108

A solution was prepared by dissolving 0.53 g of Magnolol into DMF. The solution, wherein 80 mg of sodium hydride (60% oiliness) was added, was stirred at room temperature until generation of hydrogen gas stopped. The reaction mixture, added 1.0 g of 2-(10-iododecyloxy)tetrahydropyrane, was heated to 70° C. with stirring for 3 hours. The solvent in the reaction mixtures was removed under reduced pressure, and an aqueous solution of ammonium chloride was added into the residue to extract with diethylether. The extract was washed with an aqueous solution saturated with NaCl, dried with sodium sulfate and concentrated. The concentrate was purified by a silica gel column-chromatography (n-hexane:ethyl acetate=10:1) to yield 0.27 g of 4-allyl-2-[5-allyl-2-(10-tetrahydropyranyloxydecyloxy)phenyl]phenol. The subject thus obtained was dissolved into 10 ml of ethanol, 1 ml of hydrochloric acid was added thereinto and stirred for 3 hours at room temperature. The reactant, wherein 100 ml of water was added, was extracted with diethylether. The extract was washed with water, sodium hydrogencarbonate and an aqueous solution saturated with NaCl in turn, dried with sodium sulfate and concentrated. The concentrate was purified by a silica gel column-chromatography (n-hexane:ethyl acetate=15:1) to yield 0.16 g of 4-allyl-2-[5-allyl-2-(10-hydroxy-decyloxy)-phenyl]phenol.

NMR (CDCl₃) δ: 1.15-1.80 (16H, m), 3.30-3.45 (4H, m), 3.63 (2H, t, J=6.5 Hz), 4.01 (2H, t, J=6.5 Hz), 5.00-5.15 (4H. m), 5.85-6.10 (2H, m), 6.95 (1H, s), 6.90-7.20 (6H. m).

In a manner analogous to that described in Example 108 hereinabove, the compounds, which are described in Examples 1, 2, 53, 54-59, 66, 73 and 75-93, were obtained from those of pertinent starting materials.

EXAMPLE 109

A solution was prepared by dissolving 0.2 g of 3,3',5,5'-tetraallyl-2,4'-biphenyldiol in 10 ml of ethyl acetate. The solution was catalytic reduced with 50 mg of 5% palladium-carbon catalyst at room temperature under normal pressure. The catalyst was filtered out, and the filtrate was concentrated and purified by a silica gel column-chromatography (n-hexane:ethyl acetate=5:1) to yield 0.15 g of 3,3',5,5'-tetrapropyl-2,4'-biphenyldiol.

NMR (CDCl$_3$) δ: 0.92–1.05 (12H, m), 1.60–1.80 (8H, m), 2.45–2.70 (8H, m), 4.74 (1H, s), 5.22 (1H, s), 6.85–7.15 (4H, m).

In a manner analogous to that described in Example 109 hereinabove, the compounds, which are described in Examples 1, 4–6, 12–16, 19, 20, 22, 24, 33, 37–39, 43–48, 50–53, 60–62 and 66–70, were obtained from those of pertinent starting materials.

EXAMPLE 110

A solution was prepared by dissolving 150 mg of paraformaldehyde and 0.5 ml of pyrrolidine into 5 ml of ethanol. The solution was heated with stirring until it was uniformalized. 2ml of the solution aforesaid was added to the ethanol solution of 0.3 g of 3,3'-diallyl-5-ethyl-2,4'-biphenyldiol. The reaction mixture was refluxed by heating for 4 hours and concentrated. The concentrate was purified by a silica gel column-chromatography (n-hexane:ethyl acetate=5:1). The fraction was concentrated, hydrochlorinated with hydrochloric acid/ethanol and recrystallized from ethanol-diethylether to yield 280 mg of light yellow powder 3,340-diallyl-5-ethyl-5'-pyrrolidinomethyl-2,4'-biphenyldiol hydrochloride having a b.p. of 105°–108° C.

In a manner analogous to that described in Example 110 hereinabove, the compounds, which are described in Examples 32, 40 and 45, were obtained from those of pertinent starting materials.

EXAMPLE 111

A solution was prepared by dissolving 5.16 g of 5-ethyl 2,4-dimethoxybiphenyl in 200 ml of methylene chloride. The solution was cooled by an ice bath, dropwised addition of 500 ml of methylene chloride solution (1M) of boron tribromide. The addition was took 1 hour. The reaction mixture was stirred for 5 hours at room temperature, and methanol was added thereinto with cooling by ice to decompose excess of agents. The solvent in the reaction mixture was distilled away under reduced pressure, and water was added to the residue, precipitated crystal. The crystal was filtered out, washed with water and n-hexane, and dried to yield 43 g of white powder 5-ethyl-2,4'-biphenyldiol having a bp of 109.0°–111.0° C.

In a manner analogous to that described in Example 111 hereinabove, the compounds, which are described in Examples 3, 5–61, 63, 66, 69–98 and 100, were obtained from those of pertinent starting materials.

EXAMPLE 112

20 ml of the solution was prepared by dissolving 1.0 g of 2,4'-bis-(methoxymethoxy)-5-methylthiobiphenyl in methanol. 1 ml of conc. hydrochloric acid was added to the solution. The solution is stirred for 5 hours in room temperature, neutralized with water solution of sodium hydrogencarbonate and extracted with diethylether. The extract was washed with saturated salt water, dried with sodium sulfate and concentrated. The concentrate was purified by a silica gel column-chromatography (n-hexane:ethyl acetate=15:1) and recrystallized from dichloromethane/n-hexane to yield 0.6 g of white powder 5-methylthio-2,4'-biphenyldiol having a m.p. of 108.0°–111.0° C.

In a manner analogous to that described in Example 112 hereinabove, the compounds, which are described in Examples 3, 5–61, 63, 66, 69–98 and 100, were obtained from those of pertinent starting materials.

EXAMPLE 113

A mixture was prepared by mixing 0.5 g of 4-allyl-2-[5allyl-2-(2-chloroethoxy)phenyl]phenol and 1.5 g of sodium iodide with 20 ml of acetonitryl. The mixture was refluxed by heating for 4 hours with stirring, 1 ml of diethylamine was added thereinto, refluxed for 3 hours with stirring and concentrated. The concentrate, wherein water solution of sodium hydrogencarbonate was added, was extracted with chloroform, dried with sodium sulfate and concentrated. The concentrate was purified by a silica gel column-chromatography (dichloromethane:methanol=30:1) to yield 0.3 g of 4-allyl-2-{5-allyl-2-[2-(N, N-diethyl-amino)ethoxy]phenyl}phenol.

NMR )CDCl$_3$) δ: 1.02 (8H, t, J=7.0 Hz), 2.62 (4H, q, J=7.0 Hz), 2.76 (2H, t, J=5.0 Hz), 3.37 (4H, d, J=7.0 Hz), 4.13 (2H, t, J=5.0 Hz), 5.00–5.15 (4H, m), 5.30 (1H, s), 5.90–6.10 (2H, m), 6.85–7.20 (6H, m).

EXAMPLE 114

A solution was prepared by dissolving 0.42 g of 4-allyl-2-[5-allyl-2-(2-chloroethoxy)-phenyl]phenol and 1.0 g of sodium iodide into 20 ml of acetonitril. The solution was refluxed by heating with stirring for 4 hours, added 1 ml of 15% water solution of sodium methylmercaptan, refluxed with stirring for 3 hours and concentrated. The concentrate, wherein an aqueous solution of ammonium chloride was added and extracted with diethylether. The extract was washed with an aqueous solution saturated with NaCl, dried with sodium sulfate and concen- trated. The concentrate was purified by a silica gel column- chromatography (n-hexane:ethyl acetate=20:1) to yield 0.12 g of 5,5'-diallyl-2,2'-ethylenedioxy-biphenyl (I) from the 1st fraction and 0.12 g of 5-allyl-2-[5-allyl-2-(2-methylthio)-ethoxyphenyl]phenol (II) by concentrating the 2nd fraction.

(I) NMR (CDCl$_3$) δ: 3.41 (4H, d, J=7.0 Hz), 4.00–4.15 (2H, m), 4.30–4.50 (2H, m), 5.00–5.20 (4H, m), 5.90–6.10 (2H, m), 7.00–7.20 (6H, m).

(II) NMR (CDCl$_3$) δ: 2.04 (3H, s), 2.79 (2H, t, J=6.5 Hz), 3.30–3.45 (4H, m), 4.17 (2H, t, J=6.5 Hz), 5.00–5.15 (4H, m), 5.85–6.08 (2H, m), 6.22 (1H, s), 6.90–7.20 (6H, m).

EXAMPLE 115

A mixture was prepared by adding 0.3 g of 2,6-di-tert-buthyl- 4-mercaptophenol and 0.5 g of potassium carbonate into 5 ml of DMF. The mixture was stirred for 1 hour at room temperature, 0.5 g of 4-allyl-2-[5-allyl-2-(6-bromohexyloxy)phenyl]phenol was added thereinto and stirred overnight at room temperature with nitrogen gas blowing. An aqueous solution of ammonium chloride was added into the reaction mixture, and the mixture was extracted with diethylether. The extract was washed with an aqueous solution saturated with NaCl, dried with sodium sulfate and concentrated. The concentrate was purified by a silica gel column-chormatography (n-hexane:ethyl acetate=15:1) to yield 0.3 g of 4-allyl-2-{5-allyl-2-[6-(3,5-di-tert-butyl-4-hydroxyphenylthio)hexyloxy]phenyl}phenol.

NMR (CDCl$_3$) δ: 1.30–1.80 (8H, m), 1.42 (18H, s), 2.77 (2H, t, J=7.0 Hz), 3.35–3.45 (4H, m), 4.01 (2H, t, J=6.5 Hz), 5.00–5.15 (4H, m), 5.18 (1H, s), 5.90–6.10 (2H, s), 6.52 (1H, s), 6.90–7.20 (6H, m), 7.21 (2H, s).

In a manner analogous to that dissolving in Example 113–115 hereinabove, the compounds, which are described in Examples 79, 80, 81, 91 and 92, were obtained from those of pertinent starting materials.

EXAMPLE 116

A solution was prepared by dissolving 1.2 g of 5-[4-allyl-2-(5-allyl-2-hydroxyphenyl)phenoxy]veleric acid ethylester into 20 ml of ethanol. The solution, wherein 10 ml of 10% water solution of sodium hydroxide was added, was refluxed by heating with nitrogen gas blowing for 2 hours and concentrated. The concentrate was acidified with water and hydrochloric acid added thereinto and extracted with diethylether. The extract was washed with water until the washing comes neutral, and then washed with an aqueous solution saturated with NaCl, dried with sodium sulfate and concentrated to yield 1.0 g of 5-[4-allyl-2-(5-allyl-2-hydroxyphenyl)phenoxy]veleric acid.

NMR (CDCl$_3$) δ: 1.60–1.85 (4H, m), 2.31 (2H, t, J=7.0 Hz), 3.30–3.40 (4H, m), 4.02 (2H, t, J=7.0 Hz), 5.00–5.14 (4H, m), 5.85–6.05 (2H, m), 6.91–7.19 (6H, m).

EXAMPLE 117

A mixture was prepared by suspending 50 mg of lithium aluminium hydride into 10 ml of tetrahydrofuran. The mixture was dropwise added, while cooling, tetrahydrofuran solution of 0.2 g of 5-[4-allyl-2-(5-allyl-2-hydroxyphenyl)phenoxyl]valeric acid ethyl ester. The reaction mixture was stirred for 4 hours at room temperature, added water, acidified with hydrochloric acid and extracted with diethylether. The extract was washed with water and solution sodium hydrogencarbonate, dried with sodium sulfate and concentrated. The concentrate was purified by a silica gel column-chromatography (n-hexane:ethyl acetate=4:1) to yield 0.14 g of 4-allyl-2-[5-allyl-2-(5-hydroxypentoxyphenyl)-phenol].

NMR (CDCl$_3$) δ: 1.30–1.65 (5H, m), 1.70–1.79 (2H, m), 3.30–3.45 (4H, m), 3.55–3.62 (2H, m), 4.04 (2H, t, J=7.0 Hz), 5.03–5.13 (4H, m), 5.85–6.05 (2H, m), 6.54 (1H, s), 6.92–7.20 (5H, m).

In a manner analogous to that described in Example 117 hereinabove, the compounds, which are described in Examples 73, 75 and 89, were obtained from those of pertinent starting materials.

EXAMPLE 118

A mixture was prepared by adding 0.2 g of 4-allyl-2-[5-allyl- 2-(6-bromohexyloxy)phenyl]phenol and 0.1 g of silver acetate to 3 ml of acetic acid. The mixture was refluxed by heating for 2 hours and concentrated. The concentrate was extracted with diethylether. The extract was washed with solution sodium hydrogencarbonate and an aqueous solution saturated with NaCl, dried with sodium sulfate and concentrated. The concentrate was purified by a silica gel column-chromatography (n-hexane:ethyl acetate=15:1) to yield 0.12 g of 4-allyl-2-[5allyl-2-(6-acetoxyhexyloxy)phenyl]phenol.

NMR (CDCl$_3$) δ: 1.25–1.80 (8H, m), 2.03 (3H, s), 3.35–3.45 (4H, m), 3.95–4.10 (4H, m), 5.00–5.15 (4H, m), 5.90–6.10 (2H, m), 6.51 (1H, s), 6.90–7.20 (6H, m).

EXAMPLE 119

A mixture was prepared by adding 0.1 g of 4-allyl-2-[5-allyl-2-(6-acetoxyhexyloxy)phenl]phenol and 0.1 g of pottasium carbonate into 5 ml of methanol. The mixture was stirred overnight at room temperature, 0.1 g of ammonium chloride was added thereinto and concentrated. Water was added into the concentrate to extract with diethylether. The extract was washed with an aqueous solution saturated with NaCl, dried with sodium sulfate and concentrated. The concentrate was purified by a silica gel column-chromatography (n-hexane:ethylacetate=5:1) to yield 80 mg of 4-allyl-2-[5-allyl-2-(6-hydroxyhexyloxy)phenyl]phenol.

NMR (CDCl$_3$) δ: 1.20–1.80 (9H, m), 3.5–3.45 (4H, m), 3.55–3.65 (2H, m), 4.03 (2H, t, J=6.5 Hz), 5.00–5.15 (4H, m), 5.85–6.10 (2H, m), 6.58 (1H, s), 6.90–7.20 (6H, m).

In a manner analogous to that described in Example 119 hereinabove, the compounds, which are described in Examples 73, 75 and 93, were obtained from those of pertinent starting materials.

EXAMPLE 120

30 kg of *Magnolia obovata* T$_{HUNB}$ (Japanese drug "Wakoboku") was extracted with methanol at room temperature. 100 g of the extract was injected into silica gel column-chromatography (Wakogel C-200, 1.5 kg) and divided into fraction 1 to 6 by gradient elution with chloroform to chloroform-methanol (7/3; v/v).

12.45 g of fraction 1 was injected into silica gel column-chromatography (Wakogel C-300, 200 kg) and eluted with n-hexane/ethyl acetate (1/1: v/v) to divide the elute into fraction A and B. 2.33 g of fraction B was injected into column-chromatography (Sefadex LH-20, manufactured by Pharmacia, 1 liter) and eluted with methanol to yield 42.3 g of colorless and oily piperitylmagnolol.

14.28 g of the fraction 2 was injected into column-chromatography (HW-40F, manufactured by Toyo Soda, 1 liter) and eluted with methanol/dichloromethane (4/1; v/v) to yield 8.43 g of crystal of magnolol.

4.48 g fraction 3 was injected into column-chromatography packed in the column (HW-40F, Toyo Soda made, 1 liter) and eluted with methanol/dichloromethane (4/1; v/v) to yield fraction C and C. 2 g of fraction D was injected into solica gel-column-chromatography (Wakogel C-300, 100 g) and eluted with n-hexane/ethyl acetate (13/1: v/v) to yield 0.5 g of white crystal of Honokiol.

Various physical properties of piperitylmagnolol, magnolol and Honokiol obtained by the method aforesaid are in accord with that mentioned in the literature.

The physical properties of piperitilmagnolol was reported in the Digest of Lecture of the 102nd Annual Meeting of the Institute of Japanese Pharmacy (Osaka), p. 545 (1982), by Seiji Yahara, et al. and the physical properties on Magnolol and Honokiol are reported in the Chemical Pharmacutical Bulletin, 20, 212 (1972), by Fujita, et al.

EXAMPLE 121

A solution was prepared by dissolving 13 mg of Honokiol into 2 ml of 95% ethanol. The solution, added with 0.5 mg of 10% palladium-carbon thereinto as catalyst, was hydrogenated overnight at room temperature. The reaction was continued overnight. The catalyst in the reactant was removed and the solvent thereof was also removed under reduced pressure to yield 10 mg of colorless crystal of tetrahydro Honokiol.

The physical properties of the tetrahydroxy Honokiol obtained by the method described hereinabove was in accord with that reported in the literature.

Various physical properties of tetrahydroxy Honokiol was reported in the Shoyakugaku Zasshi (Bio-pharmacy), 36, 222 (1982), by Namba, et. al.

EXAMPLE 122

An extract was prepared by extracting 8 kg of *Magnolia obovata* T$_{HVNB}$ (bark of phipsophyllum), which was cut into pieces, added with 20 liter of methanol and extracted for 1 week at room temperature. The extract was concentrated under reduced pressure to produce rough extract. The rough extract was suspended into 8 liter of water and extracted three times with each 5 liter of ethyl acetate to yield primary extract. The primary extract was suspended into water/methanol (4:6, v/v, 10 liter), extracted three times with each 5 liter of n-hexane and concentrated under reduced pressure to yield 140 g n-hexane extract. The n-hexane extract was concentrated under reduced pressure until the water/methanol part thereof diminishes in quantity down to 5 liter. The concentrate was extracted three times with each 5 liter of ethyl acetate, and concentrated under reduced pressure to yield 274 g of ethyl acetate extract.

140 g of the n-hexane extract was injected into column-chromatography (Sefadex LH-20; 6000 ml), and the fraction was eluted with methanol/methylene chloride (7:3, v/v 12 liter) to yield 28.5 g of fraction 1, 62.9 g of fraction 2 and 46.0 g of fraction 3. 62.9 g of fraction 2 was again extracted in the same manner as aforesaid with Sefadex LH-20 silica gel column-chromatography to yield 11.3 g of fraction 4, 24.9 g of fraction 5, 22.5 g of fraction 6 and 1.9 g of fraction 7. 24.9 g of fraction 5 was injected into silica gel column-chromatography, wherein 500 g Wakogel C-300 was packed in the column, and eluted with n-hexane/ethyl acetate, wherein the ratio of n-hexane and ethyl acetate varies as; (9:1, v/v, liter), (8.5:1.5, v/v, 1 liter), (8:2, v/v, 1 liter (and (7:3, v/v, 1 liter) in turn, to yield respectively 14.4 g of fraction 8, 4.5 g of fraction 9, 3.6 g of fraction 10 and 2.2 g of fraction 11.

About 10 ml of methanol was added into 3.6 g of the fraction 10 to produce precipitate. The precipitate was filtered out to yield 2.6 g of methanol-soluble substance. The methanol-soluble substance was injected into column-chromatography wherein 50 ml of YMC-Gel (manufactured by Yamamoura Kagaku, ODS-A, 60-03; 230/70 mesh) was packed in the column and eluted with 100 ml of methanol. The eluate was injected into a negative-phase middle pressure LH column-chromatography (manufactured by Merck, Lichroprap RP-8, Grösse C), eluted with methanol/water (9:1, 1 liter) and 1 water of methanol to yield 0.19 g of fraction 11, 0.22 g of fraction 12, 1.58 g of fraction 13 and 0.303 g of fraction 14. 1.58 g of fraction 13 was injected into column-chromatography, wherein 50 g of Wakogel C-300 was packed in the column, and eluted with n-hexane/ethylacetate (85:15, v/v) to yield 0.6149 g of fraction 15 and 0.8851 g of fraction 16.

0.6149 g of fraction 15 was injected into almina column-chromatography (manufactured by Merck, Aluminiumoxide 90 active neutral III, 40 g), and purified by eluting with n-hexane/ethylacetate (8:2, v/v) to yield 0.0911 g of Compound 35.

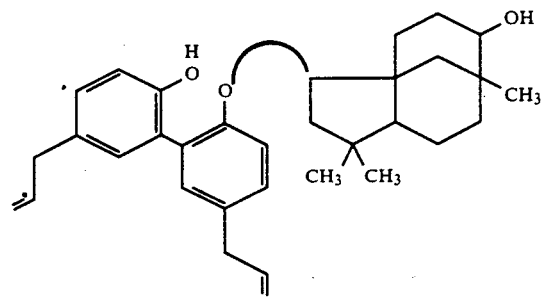

PHYSICAL PROPERTIES OF THE COMPOUND 35

Colorless and oily substance.
$[\alpha]_D^{25} = 17.0°$ (C=0.93, CHCl$_3$).
EIMS (70 ev), m/z (vel.int.): 486 [M+](7), 266(100), 237(12), 223(13), 221(5), 203(15), 197(11), 184(6)
High Resolving Power MS Observed value 486, 3127 Calculated value 486, 3134 (C$_{33}$H$_{42}$O$_3$)
UV λmax (EtOH) nm (ε): 204(46000), 208(41000), 286(5800).

The IR absorption spectrum was shown in FIG. 1, wherein main peaks of the absorptions were; νmax (CHCl$_3$) cm$^{-1}$: 3550, 3350, 1640, 1500.

Figure 2:
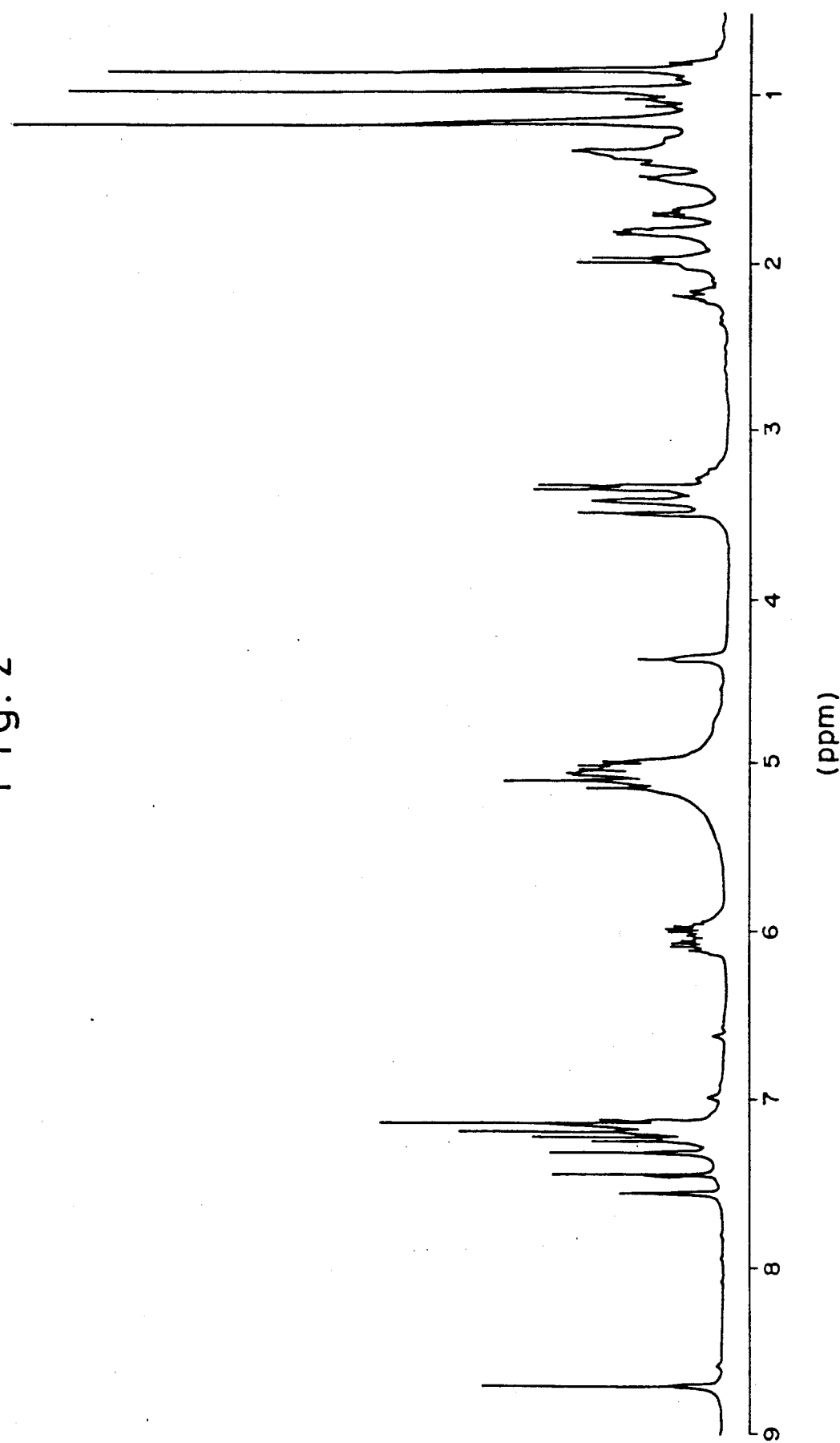
FIGS. 2 and 4 are $^1$H-NMR spectra of compounds of this invention.

The $^1$H-NMR spectrum was shown in FIG. 2, wherein main peaks of the absorption are; (400 MHz, Pyridine-d$_5$) δ ppm: 0.85 (3H, s, CH$_3$), 0.96 (3H, s, CH$_3$), 0.99 (1H, m), 1.15 (3H, s, CH$_3$), 1.16 (1H, m), 1.35 (4H, m), 1.50 (1H, dd, J=10.3, 5.4 Hz), 1.69 (1H, dd, J=12.8, 6.9 Hz), 1.81 (1H, m), 1.98 (2H, m), 2.21 (1H, td, J=13.3, 4.9 Hz), 3.34 (2H, ddd, J=6.7, 2.5, 2.5 Hz), 3.49 (1H, bs), 4.36 (1H, dd, J=6.9, 5.9 Hz), 5.00 (1H, ddt, J=10.3, 2.5, 2.5 Hz), 5.05 (1H, ddt, J=10.3, 2.5, 2.5 Hz), 5.09 (1H, ddt, J=17.2, 2.5, 2.5 Hz), 5.14 (1H, ddt, J=17.2, 2.5, 2.5 Hz), 5.98 (1H, ddt, J=17.2, 10.3, 6.7 Hz), 6.08 (1H, ddt, J=17.2, 10.3, 6.7 Hz), 7.13 (1H, d, J=8.4 Hz), 7.13 (1H, dd, J=8.4 Hz, 2.0 Hz), 7.17 (1H, dd, J=8.4 Hz, 2.0 Hz), 7.24 (1H, d, J=8.4 Hz), 7.32 (1H, d, J=2.0 Hz), 7.44 (1H, d, J=2.0 Hz), $^{13}$C-NMR (100 Hz, Pyridine-d$_5$) δ ppm: 21.90(t), 26.22(q), 28.26(t), 28.45(t), 29.77(q), 32.18(q), 34.04(t), 35.56(s), 36.70(t), 38.97(s), 40.12(t), 40.20(t), 44.83(t), 46.69(s), 51.05(d), 74.61(d), 88.38(d), 115.67(t), 115.72(t), 115.91(d), 116.99(d), 127.53(s), 128.99(d), 129.24(d), 130.46(s), 130.57(s), 132.31(s), 133.03(d), 133.14(d), 138.81(d), 139.29(d), 154.35(s), 156.05(s).

EXAMPLE 123

A mixture was prepared by adding 1 ml of piridine, 1 ml of acetic acid anhydride and 2 ml of N,N-dimethylaminopyridine into 0.303 g of the fraction 14, which was obtained in Example 122. The mixture was stirred for 5 days at room temperature, about 30 ml of ice water was added thereinto, and extracted with about 50 ml of diethylether. The diethylether part was washed with about 30 ml of 10% hydrochloric acid, about 30 ml of saturated water solution of sodium hydrogencarbonate and about 30 ml of an aqueous solution saturated with NaCl in turn, and dried with sodium sulfate anhydrite. The diethylether in the reaction mixture was distilled off under reduced pressure to yield 0.3487 g of colorless and oily substance. The substance was injected into silica gel column-chromatography (Wakogel C-300, 300 g, manufactured by Wako Jun-yaku KK), and the fraction obtained therefrom was extracted with a mixed-solvent of n-hexane/ethylacetate (95/5, v/v, 1 liter) to yield 0.1608 g of colorless and oily Compound 36.

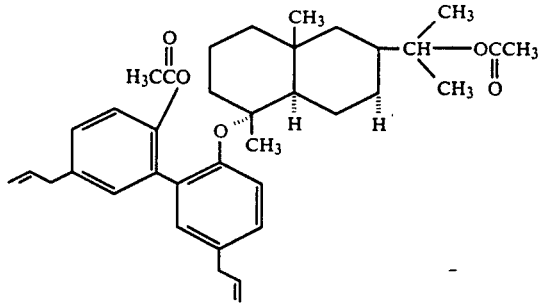

PHYSICAL PROPERTIES OF COMPOUND 36

Colorless oily substance. $[\alpha]_D^{25} = -49.4°$ (C=0.91, CHCl$_3$).

EIMS (70 ev), m/z (vel.int.): 308(22), 266(55), 237(6), 223(6), 204(12), 197(5)

Molecular-weight C$_{37}$H$_{48}$O$_5$, 572.

FDMS m/z 572[M+] (100), 307(48), 264(10), 205(55).

UV λmax (EtOH) nm (ε): 274(3900), 234(17500), 304(62700).

Figure 3:
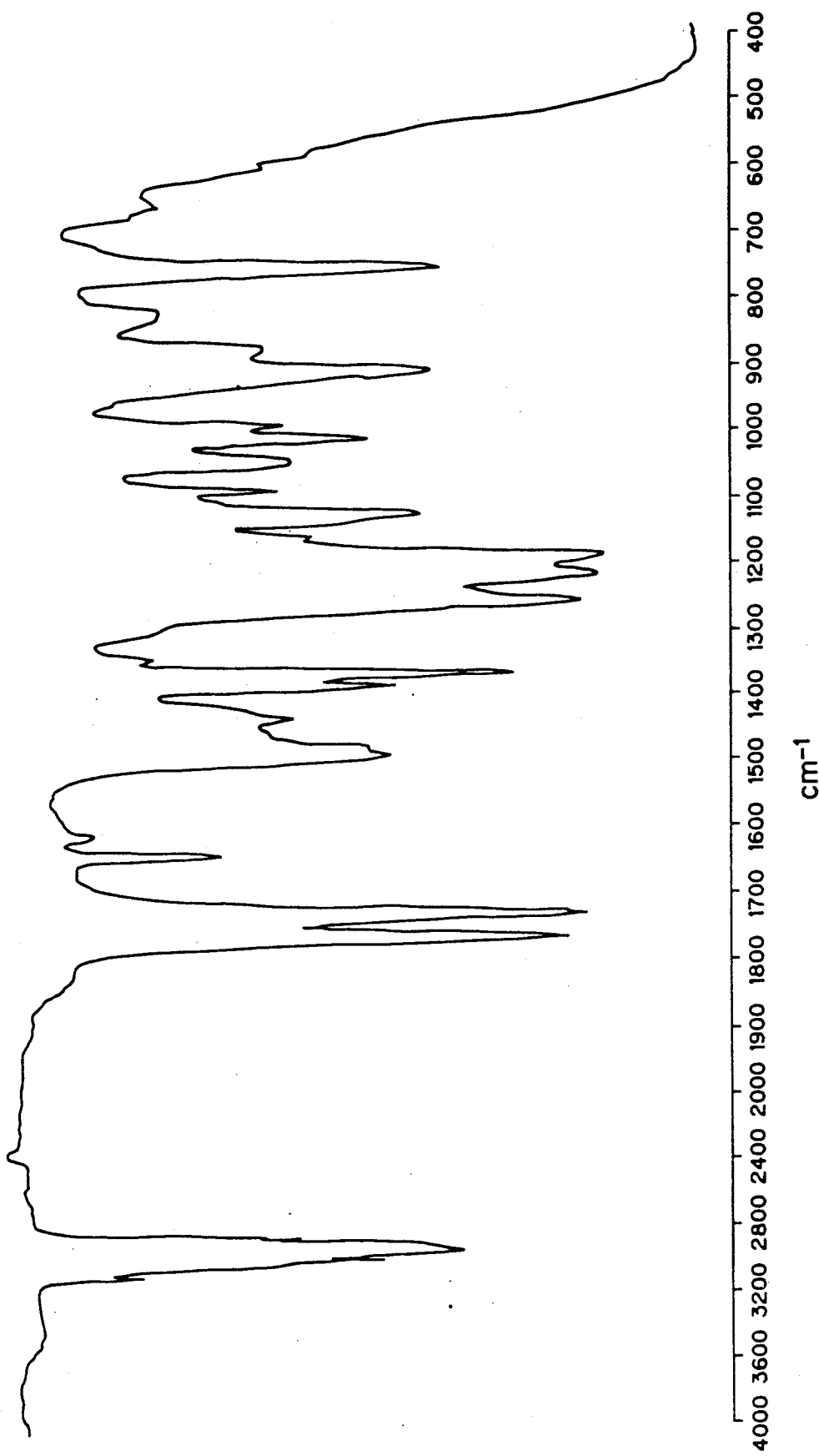

The IR absorption spectrum was shown in FIG. 3, wherein main peaks of the absorptions are;

νmax (neat) cm$^{-1}$: 2940, 1760, 1725, 1635, 1490, 1380, 1360, 1255, 1215, 1195, 1110.

Figure 4:
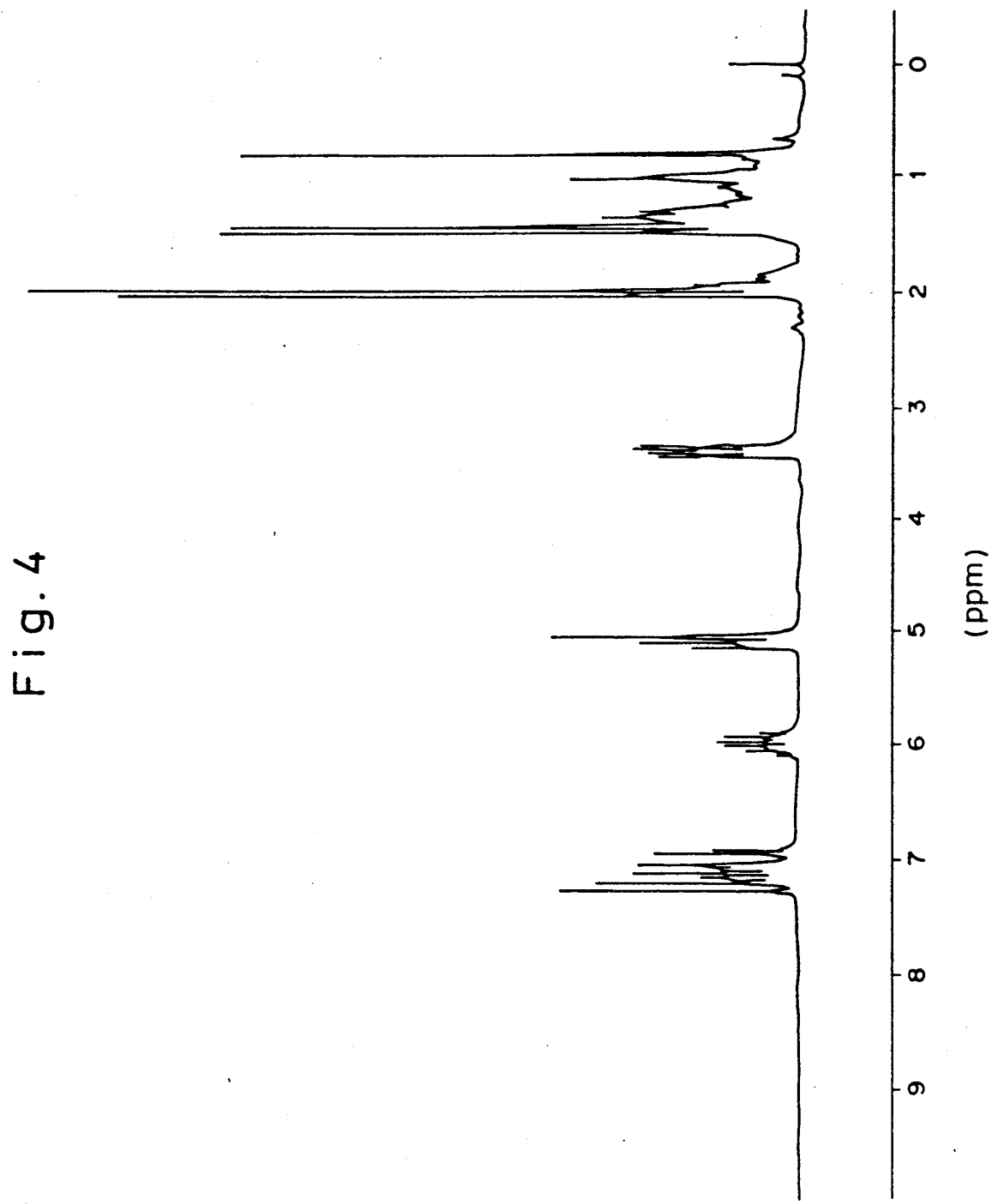

The $^1$H-NMR spectrum was shown in FIG. 4, wherein main peak of the absorption are; (200 MHz, CDCl$_3$) δ ppm: 0.81 (3H, s, CH$_3$), 1.01 (3H, s, CH$_3$), 1.42 (3H, s, CH$_3$), 1.47 (3H, s, CH$_3$), 0.85-1.47 (13H, m), 1.88 (1H, m), 1.98 (3H, s, COCH$_3$), 2.03 (3H, s, COCH$_3$), 3.36 (2H, d, J=6.8 Hz), 3.41 (2H, d, J=6.6 Hz), 5.09 (4H, m), 6.00 (2H, m), 6.90-7.27 (6H, m).

$^{13}$C-NMR (50.3 Hz, CDCl$_3$) δ ppm: 19.10(q), 19.99(t), 21.03(q, C×2), 21.63(t), 22.10(t), 22.61(q), 23.47(q), 23.92(q), 34.76(s), 38.25(t), 39.57(t), 39.71(t), 40.57(t), 44.74(t), 47.10(d), 51.60(d), 84.27(s), 85.22(s), 115.78(t), 115.98(t), 122.48(d), 124.12(d), 128.21(d), 131.26(d), 132.13(d), 133.16(s), 133.40(s), 134.34(s), 136.99(s), 137.43(d), 137.64(d), 146.70(s), 151.09(s), 169.34(s), 170.49(s).

EXAMPLE 124

A mixture was prepared by suspending 120 mg of magnesium into 10 ml of tetrahydrofuran. The mixture was dropwise added 10 ml of tetrahydrofuran solution of 1.1 g of 2-bromo-4-ethyl-anisole. The reaction mixture was refluxed by heating until magnesium in the mixture completely disappeared, cooled, 2.0 g of 2,6-tert-butyl-p-benzoquinone is added thereinto, stirred for 2 hours at room temperature, and 0.3 g of lithium aluminum hydride was added thereinto and stirred overnight at room temperature. Followed by dropwise addition of 10 ml of ethylacetate into the reaction mixture while cooling to decompose an excess of hydrides in the reaction mixture. The reaction mixture, wherein 20 ml of 10% hydrochloric acid was added, was stirred for 24 hours at room temperature, and water was added thereinto to extract with diethylether. The extract was with water, water solution of sodium hydrogencarbonate and an aqueous solution saturated with NaCl in turn, dried and concentrated. The concentrate was purified by a silica gel column chromatography (n-hexane:acetic acid=50:1) and recrystallized from water/ethanol to yield 150 mg of colorless and prism 2,6-di-tert-butyl-4-(5-ethyl-2-methoxyphenyl)-phenol having a m.p. of 78.0°-79.0° C.

In a manner analogous to that described in Example 124 hereinabove, the compounds, which are described in Examples 3-54, 56, 58, 60, 61, 63, 66, 69, 70, 96 and 97, were obtained from those of pertinent starting materials.

In a manner analogous to that described in Example 1 and 2 hereinabove, the following compounds were obtained from those of pertinent starting materials.

TABLE 2

| Example | R¹ | R² | R³ | R⁴ | R⁵ | R⁶ | R$^C$ | Crystal form (Solvent for recristallization) | Melting point (°C.) (salt) |
|---|---|---|---|---|---|---|---|---|---|
| 125 | —C(CH₃)₃ | OH | —C(CH₃)₃ | —SCH₃ | H | OH | H | colorless prism (n-hexan) | 74–75 (—) |
| 126 | —C(CH₃)₃ | OH | —C(CH₃)₃ | H | H | OH | H | colorless needle (n-hexan) | 98–100 (—) |
| 127 | —C(CH₃)₃ | OH | H | H | H | OH | H | white prism (ethyl acetate - n-hexan) | 157–157.5 (—) |
| 128 | —C(CH₃)₃ | OH | —C(CH₃)₃ | —(CH₂)₂CH₃ | OCH₃ | OCH₃ | H | colorless needle (n-hexan) | 99–100 (—) |
| 129 | H | OH | H | —(CH₂)₂CH₃ | OCH₃ | OCH₃ | H | colorless prism (ethyl acetate - n-hexan) | 114.5–115.5 (—) |
| 130 | —C(CH₃)₃ | OH | —C(CH₃)₃ | —(CH₂)₂CH₃ | OH | OH | H | colorless prism (ethyl acetate - n-hexan) | 123–124 (—) |
| 131 | —C(CH₃)₃ | OH | H | —(CH₂)₂CH₃ | OH | OH | H | colorless prism (ethyl acetate - n-hexan) | 116.5–117.5 (—) |
| 132 | —CH₂CH=CH₂ | OH | H | —(CH₂)₂CH₃ | OH | OH | H | white powder (dichloro methan - n-hexan) | 109–112 (—) |
| 133 | H | OH | H | —CH₂CH₃ | H | OCH₃ | H | white powder (ethanol - H₂O) | 103–105 (—) |
| 134 | H | OH | (2-methylthiazol-5-yl) | —CH₂CH₃ | (2-methylthiazol-5-yl) | OH | H | Light-yellow powder (ethyl acetate - n-hexan) | 148–149 (—) |
| 135 | —CH₂CH=CH₂ | OH | H | —CH₂CH₃ | H | OH | H | colorless needle (ethyl acetate - n-hexan) | 107–108.5 (—) |
| 136 | —(CH₂)₂CH₃ | OH | —CH₂(pyrazol-N-yl) | —CH₂CH₃ | —(CH₂)₂CH₃ | OH | H | white powder (n-hexan) | 166–168 (—) |

TABLE 2-continued

[Structure: biphenyl with R¹, R², R³ on one ring (with R^C), and R⁴, R⁵, R⁶ on the other ring]

| Example | R¹ | R² | R³ | R⁴ | R⁵ | R⁶ | R^C | Crystal form (Solvent for recristallization) | Melting point (°C.) (salt) |
|---|---|---|---|---|---|---|---|---|---|
| 137 | H | OH | $\underset{\parallel}{\overset{O}{-CCH_2Cl}}$ | —CH₂CH₃ | H | OCH₃ | H | Light-yellow powder (chloroform - n-hexan) | 67–68 (—) |
| 138 | H | OH | $\underset{\parallel}{\overset{O}{-CCH_2Cl}}$ | —CH₂CH₃ | $\underset{\parallel}{\overset{O}{-CCH_2Cl}}$ | OH | H | white powder (chloroform - n-hexan) | 154–155.5 (—) |
| 139 | —(CH₂)₂CH₃ | OH | —CH₂N(CH₃)₃⁺ | —CH₂CH₃ | —(CH₂)₂CH₃ | OH | H | Light-brown powder (chloroform - diethyl ether) | 185–187 (decomposition) (I⁻) |
| 140 | —(CH₂)₂CH₃ | OH | H | —CH₂CH₃ | —(CH₂)₂CH₃ | OH | —(CH₂)₂CH₃ | NMR | (—) |
| 141 | H | OH | OH | —CH₂CH₃ | —CH₂CH=CH₂ | OH | —(CH₂)₂CH₃ | NMR | (—) |
| 142 | H | OCH₃ | —OCH₃ | —CH₂CH₃ | H | OH | —(CH₂)₂CH₃ | NMR | (—) |
| 143 | H | OCH₃ | —OCH₃ | —CH₂CH₃ | —CH₂CH=CH₂ | OH | H | NMR | (—) |
| 144 | H | OH | H | —CH₂CH₃ | —CH₂CH=CH₂ | OH | H | NMR | (—) |
| 145 | —(CH₂)₂CH₃ | OH | $-CH_2N\underset{\text{(pyrrolidinone)}}{\bigcirc}$ | —CH₂CH₃ | —(CH₂)₂CH₃ | OH | H | NMR | (—) |
| 146 | —(CH₂)₂CH₃ | OH | —CH₂OCH₂CH₃ | —CH₂CH₃ | —(CH₂)₂CH₃ | OH | H | NMR | (—) |
| 147 | —(CH₂)₂CH₃ | OH | —CH₂OCH₂CH₃ | $\underset{-CHOCH_2CH_3}{CH_3}$ | —(CH₂)₂CH₃ | OH | H | NMR | (—) |
| 148 | —(CH₂)₂CH₃ | OH | —CH₂OH | —CH₂CH₃ | —(CH₂)₂CH₃ | OH | H | NMR | (—) |
| 149 | —C(CH₃)₃ | OH | —C(CH₃)₃ | —SCH₃ | H | —OCH₂OCH₃ | H | NMR | (—) |
| 150 | —C(CH₃)₃ | —OCH₂CH=CH₂ | H | H | H | —OCH₂CH=CH₂ | H | NMR | (—) |

TABLE 2-continued

[Structure: biphenyl with substituents R¹, R², R³ on one ring, R^C at the 2-position, and R⁴, R⁵, R⁶ on the other ring]

| Example | R¹ | R² | R³ | R⁴ | R⁵ | R⁶ | R^C | Crystal form (Solvent for recristallization) | Melting point (C.) (salt) |
|---|---|---|---|---|---|---|---|---|---|
| 151 | —CH₂CH=CH₂ | —OCCH₃ (O=) | H | —CH₂CH₃ | —CH₂CH=CH₂ | —OCCH₃ (O=) | H | NMR | (—) |
| 152 | —C(CH₃)₃ | OH | —CH₂CH=CH₂ | —SCH₃ | —CH₂CH=CH₂ | OH | H | NMR | (—) |
| 153 | —CH₂CH=CH₂ | OH | H | —(CH₂)₂CH₃ | OCH₃ | OCH₃ | H | NMR | (—) |
| 154 | —C(CH₃)₃ | OH | —CH₂CH=CH₂ | H | —CH₂CH=CH₂ | OH | H | NMR | (—) |

TABLE 3

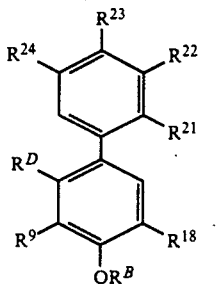

| Example | $R^{21}$ | $R^{21}$ | $R^{23}$ | $R^{24}$ | $R^9$ | $R^{18}$ | $R^B$ | $R^D$ | Crystal form (Solvent for recristallization) | Melting point (C.) (salt) |
|---|---|---|---|---|---|---|---|---|---|---|
| 155 | H | H | OH | —CH$_2$CH=CH$_2$ | H | OCH$_3$ | CH$_3$ | —(CH$_2$)$_2$CH$_3$ | Colorless needle (dichloro methan-n-hexan) | 79–81 (—) |
| 156 | H | H | OH | —CH$_2$CH=CH$_2$ | H | OH | OH | —(CH$_2$)$_2$CH$_3$ | NMR | (—) |
| 157 | H | H | OH | H | H | OCH$_3$ | CH$_3$ | —(CH$_2$)$_2$CH$_3$ | NMR | (—) |

NMR (CDCl$_3$) δ (ppm):

Compound of example 140: 0.99 (3H, t, J=7.5Hz), 1.00 (3H, t, J=7.5Hz), 1.22 (3H, t, J=7.5Hz), 1.60–1.75 (4H, m), 2.60–2.70 (6H, m), 4.86 (1H, s), 5.13 (1H, s), 6.80–6.90 (2H, m), 6.93 (1H, d, J=2.0Hz), 7.15 (1H, dd, J=8.0Hz, 2.0Hz), 7.21 (1H, d, J=2.0Hz).

Compound of example 141: 0.77 (3H, t, J=7.5Hz), 1.20 (3H, t, J=6.5Hz), 1.42 (2H, m), 2.20–2.35 (2H, m), 2.57 (2H, q, J=7.5Hz), 3.42 (2H, d, J=6.5Hz), 4.76 (1H, s), 5.00–5.20 (3H, m), 5.29 (1H, s), 5.95–6.15 (1H, m), 6.72 (1H, s), 6.78 (1H, d, J=2.5Hz), 6.85 (1H, s), 6.94 (1H, d, J=2.5Hz).

Compound of example 142: 0.80 (3H, t, J=7.5Hz), 1.23 (3H, t, JU=7.5Hz), 1.40–1.52 (2H, m), 2.35–2.50 (2H, m), 2.61 (2H, q, J=7.5Hz), 3.84 (3H, s), 3.93 (3H, s), 4.70 (1H, s), 6.72 (1H, s), 6.84 (1H, s), 6.90 (1H, d, J=8.0Hz), 6.95 (1H, d, J=2.0Hz), 7.10 (1H, dd, J=8.0Hz, 2.0Hz).

Compound of example 143: 0.79 (3H, t, J=7.5Hz), 1.22 (3H, t, J=7.5z), 1.37–1.55 (2H, m), 2.27–2.47 (2H, m), 2.59 (2H, q, J=7.5Hz), 3.43 (3H, d, J=6.5Hz), 3.84 (3H, s), 3.93 (3H, s), 4.76 (1H, s), 5.05–5.17 (2H, m), 6.00–6.17 (1H, m), 6.72 (1H, s), 6.82 (1H, d, J=2.0z), 6.83 (1H, s), 6.96 (1H, d, J=2.0Hz).

Compound of example 144: 1.22 (3H, t, J=7.5Hz), 2.58 (2H, q, J=7.5Hz), 3.44 (2H, d, J=6.5Hz), 4.99 (1H, s), 5.05–5.20 (2H, m), 5.13 (1H, s), 6.00–6.15 (1H, m), 6.90–7.00 (4H, m), 7.30–7.40 (2H, m)

Compound of example 145: 0.95–1.05 (6H, m), 1.23 (3H, t, J=7.5Hz), 1.55–1.70 (4H, m), 2.00–2.15 (2H, m), 2.40–2.70 (8H, m), 3.53 (2H, t, J=7.0Hz), 4.37 (2H, s), 5.14 (1H, s), 6.87 (1H, d, J=2.0Hz), 6.94 (1H, d, J=2.0Hz), 7.03 (1H, d, J=2.0Hz), 7.20 (1H, d, J=2.0Hz), 9.41 (1H, s).

Compound of example 146: 0.98 (3H, t, J=7.5Hz), 1.00 (3H, t, J=7.5Hz), 1.22 (3H, t, J=7.5Hz), 1.30 (3H, t, J=7.0Hz), 1.56–1.76 (4H, m), 2.50–2.70 (6H, m), 3.65 (2H, q, J=7.0Hz), 4.73 (2H, s), 5.13 (1H, s), 6.85 (1H, d, J=2.5Hz), 6.90–7.00 (2H, m), 7.16 (1H, d, J=2.0Hz), 7.96 (1H, s).

Compounds of example 147: 0.99 (6H, t, J=7.5Hz), 1.18 (3H, t, J=7.0Hz), 1.31 (3HY, t, J=7.0Hz), 1.44 (3H, d, J=6.5Hz), 1.60–1.75 (4H, m), 2.60–2.70 (4H, m), 3.30–3.50 (2H, m), 3.66 (2H, q, J=7.0Hz), 4.33 (1H, q, J=6.5Hz), 4.74 (2H, s), 5.25 (1H, s), 6.90–7.00 (2H, m), 7.04 (1H, d, J=2.0Hz), 7.16 (1H, d, J=2.0Hz), 7.97 (1H, s).

Compound of example 348: 0.98 (3H, t, J=7.5Hz), 0.99 (3H, t, J=7.5Hz), 1.22 (3H, t, J=7.5Hz), 2.50–2.75 (6H, m), 4.89 (2H, s), 5.13 (1H, s), 6.84 (1H, d, J=2.0Hz), 6.93 (1H, d, J=2.0Hz), 6.95 (1H, d, J=2.0Hz), 7.17 (1H, d, J=2.0Hz), 7.95 (1H, s).

Compound of example 149: 1.47 (18H, s), 2.48 (3H, s), 3.42 (3H, s), 5.10 (2H, s), 5.26 (1H, s), 7.14 (1H, d, J=9.0Hz), 7.18 (1H, dd, J=9.0Hz, 2.0Hz), 7.29 (1H, d, J2.0Hz), 7.34 (2H, s).

Compound of example 150: 1.43 (9H, s), 4.54 (2H, d, J=5.0Hz), 4.61 (2H, d, J=5.0Hz), 5.17–5.53 (4H, m), 5.90–6.20 (2H, m), 6.90–7.10 (3H, m), 7.20–7.40 (3H, m), 7.54 (1H, d, J=2.0Hz).

Compound of example 151: 1.25 (3H, t, J=7.5Hz), 2.03 (3H, s), 2.32 (3H, s), 2.65 (2H, q, J=7.5Hz), 3.25–3.35 (4H, m), 5.00–5.18 (4H, m), 5.80–6.00 (2H, m), 7.00–7.10 (3H, m), 7.25–7.29 (2H, m).

Compound of example 152: 1.42 (9H, s), 2.46 (3H, s), 3.40–3.50 (4H, m), 5.05–5.40 (6H, m), 5.90–6.10 (2H, m), 7.00–7.10 (3H, m), 7.23 (1H, d, J=2.0Hz).

Compound of example 153: 0.97 (3H, t, J=7.5Hz), 1.60–1.75 (2H, M), 2.57 (2H, t, J=7.5Hz), 3.46 (2H, d, J=6.5Hz), 3.55 (3H, s), 3.89 (3H, s), 4.99 (1H, s), 5.13–5.25 (2H, m), 6.00–6.15 (1H, m), 6.70 (1H, d, J=2.0Hz), 6.73 (1H, d, J=2.0Hz), 6.85 (1H, d, J=9.0Hz), 7.30–7.40 (2H, m).

Compound of example 154: 1.42 (9H, s), 3.46 (4H, d, J=6.5Hz), 5.05–5.45 (6H, m), 5.95–6.15 (2H, m), 6.90–7.15 (5H, m).

Compound of example 156: 0.80 (3H, t, J=7.5Hz), 1.40–1.55 (2H, m), 2.42 (2H, t, J=7.5hz), 3.42 (2H, d, J=6.5Hz), 5.00 (1H, s), 5.10–5.20 (4H, m), 5.95–6.13 (1H, m), 6.70 (1H, s), 6.75 (1H, s), 6.81 (1H, d, J=9.0Hz), 7.00–7.05 (2H. m).

Compound of example 157: 0.82 (3H, t, J=7.5Hz), 1.40–1.55 (2H, m), 2.40–2.55 (2H, m), 3.85 (3H, s), 3.91 (3H, s), 4.95 (1H, s), 6.70 (1H, s) 6.77 (1H, s), 6.86 (2H, d, J=8.5Hz), 7.16 (2H, d, J=8.5Hz).

EXAMPLE 158

In a manner analogous to that described in Example 101 hereinabove, the compound, which was described in Example 150, was obtained from those of pertinent starting materials.

EXAMPLE 159

In a manner analogous to that described in Example 102 hereinabove, the compound, which are described in Examples 141, 143, 152, 153, 154, 155 and 156, were obtained from those of pertinent starting materials.

EXAMPLE 160

In a manner analogous to that described in Example 111 and 112 hereinabove, the compounds, which were described in Example s137-149 and 152-157, were obtained from those of pertinent starting materials.

EXAMPLE 161

In a manner analogous to that described in Example 124 hereinabove, the compound, which are described in Example 137-141, 144-149 152-157, were obtained from those of pertinent starting materials.

EXAMPLE 162

A mixture was prepared by suspending 25 g of aluminium chloride into 100 ml of 1,2-dichloroethane. The mixture, wherein 5 ml chloroacetyl chloride was added, was stirred for 1 hour at room temperature, followed by dropwise addition of 5-ethyl-2,4'-dimethoxy-biphenyl, wherein 10 g of 1.2-dichloroethane was dropwise and stirred overnight at room temperature. The reaction mixture was transferred into ice water to extract with dichloroethane. The extract was washed with saturated salt water, dried with sodium sulfate and concentrated. The concentrate was purified by a silica gel column chromatography (10:1, n-hexane:ethyl acetate) and recrystallized from chloroform/n-hexane to yield 2.5 g of light yellow and powdered 2-chloroacetyl-4-(5-ethyl-2-methoxyphenyl)phenol having a m.p. of 67.0°-68.0° C. Then, the fraction which was eluted with n-hexane/ethyl acetate: 3/1, was concentrated. The concentrate was recrystallized from chloroform/n-hexane to yield 1.5 g of white powder 3,3-bischloroacetyl-5-ethyl-2,4'-biphenyldiol having a m.p. of 154.0°-155.5° C.

EXAMPLE 163

A mixture was prepared by adding 0.7 g of 2-chloroacetyl-4-(5-ethyl-2-methoxyphenyl)phenol and 0.5 g of thioacetoamido into 10 ml of ethanol. The mixture was refluxed by heating for 4 hours and concentrated. The concentrate, wherein 10% water solution of sodium hydrogencarbonate was added, was extracted with dichloromethane, dried with sodium sulfate and concentrated. The concentrate was purified with p-hexane. The precipitate which appears by the purification was filtered out and recrystallized from methanol/water to yield 0.3 g of white powder 4-(5-ethyl-2-methoxyphenyl)-2-(2-ethyl-4-thiazolyl)-phenol having a m.p. of 103°-105° C.

EXAMPLE 184

A mixture was prepared by adding 1 g of paraformaldehyde and 3 ml of 40% water solution of dimethylamine into 20 ml of ethanol. The mixture was stirred at room temperature until the mixture comes homogeneous solution. The solution, wherein 5.0 g of 5-ethyl-3,3'-dipropyl-2,4'-biphenyldiol was added, was refluxed by heating for 5 hours. The solvent in the reaction mixture was removed by an evaporator. The residue thereof was dissolved into 100 ml of chloroform, 10 ml of methyl iodide was added thereinto, let standing the solution overnight and diethylether was added thereinto. The precipitate produced therein was filtered out, dried, and recrystallized from chloroform-diethylether to yield 5.0 g of light brown and power N-[5-(5-ethyl-2-hydroxy-3propylphenyl)-2-hydroxy-3-propylbenzyl]-N,N,N-trimethyl-ammonium iodide having a m.p. of 185.0°÷187.0° C. (decomposed).

EXAMPLE 165

A mixture was prepared by adding 1.0 g of N-[5-(5-ethyl-2-hydroxy-3-propylphenyl)-2-hydroxy-3-propylbenzyl)-N,N,N,-trimethyl-ammonium iodide into 30 ml of ethanol saturated with ammonia, refluxed by heating for 2 hours and concentrated. 5-ethyl-3,3'-dipropyl-5'-aminomethyl-2,4-biphenyldiol thus obtained was dissolved into 20 ml of acetonitryl, 0.4 ml of ethyl 4-bromobutylate and 0.5 ml of triethylamine were added thereinto. The reaction mixture was refluxed by heating for 2hours and concentrated to obtain 5-ethyl-3,3'-dipropyl-5'-(3-ethoxycarbonyl-propylaminomethyl)-2,4-biphenyldiol. 30 ml of toluene was added into the subject thus obtained. The reaction mixture and refluxed b heating for 8 hours and purified by a silica gel column-chromatography (5:1, n-hexane:methanol) to yield 0.1 g of colorless and oily 5-ethyl-3,3'-dipropyl-5'-(2-oxopyrrolidinyl)-methyl-2,4'-biphenyldiol. The NMR analysis on the compound was in accord with that of the substance described hereinabove in Example 145.

EXAMPLE 166

A mixture was prepared by mixing 0.5 g of N-[5-5-ethyl-2-hydroxy-3-propylphenyl)-2-hydroxy-3-propylbenzyl]-N,N,N,-trimethyl-ammonium iodide and 0.5 g of imidazol into 20 ml ethanol. The mixture was refluxed by heating for 4 hours and concentrated. The concentrate was purified by a silica gel column-chromatography (dichloromethane:methanol=50:1), and the eluate was recrystallized from n-hexane to yield 0.3 g white powder 5-ethyl-3'-(1-imidzolylmethyl)-3,5'-dipropyl-2,4'-biphenyldiol having a m.p. of 166.0°-168.0° C.

In a manner analogous to that described in example 188 hereinabove, the compounds, which are described in Examples 146, 147 and 148, were obtained from those of pertinent starting materials.

EXAMPLE 167

A mixture was prepared by mixing 0.52 g of magnesium, 7.5 g of 3,4-dimethoxy-2,5-bismethoxymethoxy-6-methylbromobenzen and 0.2 ml of ethyl bromide into 30 ml of tetrahydrofurananhydride. The mixture was refluxed by heating until magnesium in the mixture disappears. The reaction mixture was cooled, 4.4 g 2,6-di-tert-butyl-p-benzoquinone was added thereinto, stirred for 2 hours, 1.5 g of lithium aluminium hydroxide was added thereinto, and stirred overnight at room temperature. An excess of hydrides in the reaction mixture was decomposed with ethylacetate, wherein 20 ml of 10% hydrochloric acid was added. The reaction mixture was stirred for 4 hours at room temperature, refluxed by heating for futher 2hours, cooled and extracted with diethylether. The extract was washed with 10% water solution of sodium hydrogencarbonate and an aqueous solution saturated with NaCl in turn, dried with sodium sulfate and concentrated. The concentrate was injected into a silica gel column-chromatography. The fraction eluted with the solvent (n-hexane:ethyl acetate=20:1) was concentrated, dissolved into 30 ml of methanol and stirred in addition of water solution of ferric chloride for 1hour, and then methanol in the reaction mixture was removed. The reactant was extracted with diethylether, and the extract was washed with an aqueous solution saturated with NaCl, dried with sodium sulfate and concentrate. The concentrated was recrystallized from ethylacetate/n-hexane to yield 0.5 g of reddish orange prism 2-(3,5-di-tert-butyl-4-hydroxyphenyl-5,6-dimethoxy-3-methyl-p-benzoquinone having a mp of 147.0°–148.0° C.

EXAMPLE 168–169

In a manner analogous to that described in Example 1, 2, and 124 hereinabove, the compound, which are described in Examples 168 and 169, were obtained from those of pertinent starting materials.

8. 2,3'-diallyl-3,4'-biphenyldiol
9. 3', 4-diallyl-3,4'-biphenyldiol
10. 5,5'-diallyl-2-(10-hydroxydecyloxy)-2'-hydroxybiphenyl
11. 5,5'-diallyl-2-[3-phthalimido-1-yl)propoxy]-2-hydroxybiphenyl
12. 5,5'-diallyl-2-(3-acethylaminopropoxy)-2'-hydroxybiphenyl
13. 5.5'-diallyl-2-(3-aminopropoxy)-2'-hydroxybiphenyl
14. 3,5'-diethyl-2,4'-biphenyldiol
15. 3,3'-diallyl-2,4'-biphenyldiol
16. 3,3'-di-n-propyl-2,4'-biphenyldiol
17. 3,3'-diallyl-5-ethyl-2,4'-biphenyldiol
18. 3,3'-diallyl-5-phenyl-2,4'-biphenyldiol
19. 3,3'-diallyl-5-t-butyl-2,4'-biphenyldiol
20. 3,3'-diallyl-5-methoxy-2,4'-biophenyldiol

TABLE 4

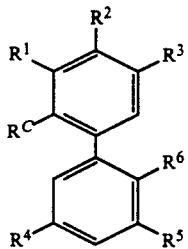

| Example | R¹ | R² | R³ | R^C | R⁴ | R⁵ | R⁶ | Crystal form (Solvent for recristallization) | Melting point (°C.) (salt) |
|---|---|---|---|---|---|---|---|---|---|
| 168 | —C(CH₃)₃ | OH | —C(CH₃)₃ | H | —CH₂CH₃ | H | —OCH | Colorless prisum (ethanol-n-H₂O) | 78–79 (—) |
| 169 | —C(CH₃)₃ | OH | —C(CH₃)₃ | H | H | H | —OCH₃ | Colorless needle (ethanol-n-H₂O) | 106–108.5 (—) |

PHARMACOLOGICAL EXAMINATION 1

The specimen for the examination was nerve cell of cerebral cortex which was aseptically separated from a rat fetus (17 days living). The method cultivation was in accordance with the method of Asou, et al. [Asou, H. Brain Res., 332, p. 335–357 (1985). The process is: The cerebral hemisphere, of which the mininx and the blood vessel were removed, was mencerated by stainless steel mesh (140 μm in Pore-size). The mecerated cell was floated on the cultural medium (10% Calf's Blood serum and 1 g/liter D-glucose contained Eagle media) and sowed by $1.5 \times 10^6$ pcs. of the cell into each dish, 35 mm in diameter, coated with poly-L-lysine. The cultivation was continued at 37° C. in 3% $CO_2$ for 24 hours. After 24 hours passed, the culture medium was changed by that containing those of test compounds. The cultivation was continued for more 9 days.

On the 10th day from the starting day of the cultivation, degree of elongation of neural processes (NS), formation of neural network (NN) and elongation of neurofibral bundle (NBV) were comparatively observed with a phase contrast microscope to evaluate. The results of the evaluation was shown in table 5.

TEST COMPOUNDS

1. Honokiol
2. Tetrahydro honokiol
3. Magnolol
4. Pyperityl magnolol
5. The compound 35
6. 5,5'-diallyl-3-(3cyclohxenyloxy)-2'-hydroxybiphenyl
7. 5,5'-diallyl-2-(3-cyclohexenyl)-2,2'-biophenyldiol
21. 3,3'-diallyl-5-methylthio-2,4'-biphenyldiol
22. 3,5'-diallyl-5'-(3-cyclohexenyl)-2,4'-biphenyldiol
23. 3',5,5'-triallyl-2,4'-biphenyldiol
24. 3',5-diallyl-5'-diethylaminoethyl-2,4'-biphenyldiol
25. 5-ethyl-3',5'-di-t-butyl-2,4'-biphenyldiol
26. 3,3',5,5'-tetrallyl-2,4'-biphenyldiol
27. 3,5'-diallyl-3',5'-(3-cyclohexenyl)-2,4'-biphenyldiol
28. 3,3',5,5'-n-propyl-2,4'-biphenyldiol
29. 3,3'-diallyl-5,5'-diethyl-2,4'-biphenyldiol
30. 3,3'-diallyl-5-ethyl-5'-fluoro-2,4'-biphenyldiol
31. 3,3'-diallyl-5-ethyl-5'-[(2-dimethylamido-pyrrolidine-1 -yl)-methyl]2,4'-biphenyldiol
32. 3,3'-diallyl-5-ethyl-5'-bromo-2,4'-biphenyldiol
33. 3,3'-diallyl-5-ethyl-5'-acetyl-2,4'-biphenyldiol
34. 3,3'-diallyl-5-ethyl-5'-t-butyl-2,4'-biphenyldiol
35. 3,3'-diallyl-5-ethyl-5'-(1-methylaminoethyl)-2,4'-bipheyldiol
36. 3,3'-diallyl-5-ethyl-5'-[1-(N-methylamino) ethyl]-2,4'-biphenyldiol
37. 3'-phenyl-5-ethyl-2,4'-biphenyldiol
38. 5-ethyl-3'-furuoro-2,4'-biphenyldiol
39. 3'-5-butyl-5-ethyl-2,4'-biphenyldiol
40. 3,3'-diallyl-5-isopropyl-2,4'-biphenyldiol
41. 3,3'-diallyl-5-benzyl-2,4'-biphrenyldiol
42. 2-(3,5-di-tert-4-hydroxyphenyl)-5,6-dimethoxy-3-methyl-p-benzoquinon
43. 3'-allyl-2-propyl-4,4',5-biphenyltriol
44. 3'-allyl-5-ethyl-2'-propyl-2,4',5'-biphenyltriol
45. 3'-allyl-5-propyl-2,3,4'-biphenyltriol
46. 3,3'-diallyl-5-ethyl-5'-phenyl-2,4'-biphenyldiol
47. 3',5'-di-t-butyl-2-methoxy-5-ethyl-4'-hydroxybiphenyl
48. 2-allyl-4-(4,5-dimethoxy-2-prpopylenyl)phenol 49. 8-allyl-4-ethyl-2-(4,5-dimethoxy-2-propylphenyl)-phenol
50. 3',5'-di-t-buthyl-5-propyl-2,3,4'-biphenyltriol
51. 2-allyl-4-(2,3-dimethoxy-5-propylphenyl)phenol
52. 5-ethyl-3,3'--dipropyl-2,4'-biphenldiol
53. 3',5'-di-t-buthyl-5-methylthio-2,4'-biphenyldiol
54. 3'5'-di-t-buthyl-2,4'-biphenyldiol
55. 3'-5-butyl-2,4'-biphenyldiol
56. 3,5-di-t-butyl-4-(2,3-dimethoxy-5-propylphenyl)-phenol
57. 3,3'-diallyl-5'-t-butyl-5-methylthio-2,4'-biphenyldiol
58. 3'-5-buthl-5-propyl-2,3,4'-biphenyltriol
59. 3,3'-diallyl-5'-t-butyl-2,4'-biphenyldiol
60. 2,6-di-t-butyl-4-(2-methoxyphenyl)phenol

TABLE 5

| Test compound No. | Dose (mole) | Cultured |
|---|---|---|
| 1 | $10^{-5}$ | NS(+),NN(++) |
| 2 | $10^{-5}$ | NS(+) |
| 3 | $10^{-5}$ | NS(+−) |
| 4 | $10^{-5}$ | NS(+) |
| 5 | $10^{-5}$ | NS(+) |
| 6 | $10^{-7}$ | NS(+) |
| 7 | $10^{-5}$ | NS(++),NN(++) |
| 8 | $10^{-6}$ | NS(++),NB(+) |
| 9 | $10^{-7}$ | NB(+) |
| 10 | $10^{-5}$ | NS(++) |
| 11 | $10^{-6}$ | NS(+),NB(+) |
| 12 | $10^{-6}$ | NS(+),NB(+) |
| 13 | $10^{-7}$ | NS(+) |
| 14 | $10^{-5}$ | NS(++) |
| 15 | $10^{-7}$ | NS(+) |
|  | $10^{-6}$ | NS(+),NB(+) |
| 16 | $10^{-7}$ | NS(+),NB(+) |
| 17 | $10^{-6}$ | NS(++) |
| 18 | $10^{-7}$ | NS(+) |
| 19 | $10^{-6}$ | NS(+) |
| 20 | $10^{-7}$ | NS(+),NN(+) |
| 21 | $10^{-7}$ | NS(+),NB(+) |
| 22 | $10^{-6}$ | NS(+) |
| 23 | $10^{-5}$ | NS(++) |
| 24 | $10^{-6}$ | NS(+) |
| 25 | $10^{-6}$ | NS(+) |
| 26 | $10^{-6}$ | NS(+) |
| 27 | $10^{-6}$ | NS(+) |
| 28 | $10^{-5}$ | NS(+) |
| 29 | $10^{-5}$ | NS(++) |
| 30 | $10^{-6}$ | NS(++),NB(+) |
|  | $10^{-5}$ | NS(++),NN(+) |
| 31 | $10^{-6}$ | NS(+) |
| 32 | $10^{-6}$ | NS(+),NB(+) |
| 33 | $10^{-7}$ | NS(+) |
| 34 | $10^{-5}$ | NS(++) |
| 35 | $10^{-6}$ | NS(+) |
| 36 | $10^{-5}$ | NS(+) |
| 37 | $10^{-6}$ | NS(++) |
| 38 | $10^{-5}$ | NS(++),NB(+) |
| 39 | $10^{-5}$ | NS(++),NB(+) |
| 40 | $10^{-6}$ | NS(+) |
| 41 | $10^{-6}$ | NS(+) |
| 42 | $10^{-5}$ | NS(+) |
| 43 | $10^{-7}$ | NB(+) |
|  | $10^{-6}$ | NS(+) |
| 44 | $10^{-6}$ | NS(++) |
| 45 | $10^{-6}$ | NS(++),NB(+) |
| 0.5%-ethanol (Control) | — | NS(+−) |

(++): Very strong in comparison with control
(+): Strong in comparison with control
(+−): Equal to control
(−): Inferior to control

PHARMACOLOGICAL EXAMINATION 2

The specimen for the examination was nerve cell of cerebral cortex which was aseptically separated from a rat fetus (17 days living). The nerve cells was mencerated by 70 mesh of stainless steel mesh (210 μm in Pore-size) and 100 mesh of that (150 μm in Pore-size) to make single cells. The single cells were sowed to cultivation plate having 24 halls (caliber: 17 mm) for cultivation coated with poly-L-lysine, in density of $1.5 \times 10^5$ cell/cm$^2$. The medium was consist of calf's blood serum contained EAGLE'S MEM medium (manufactured by Nissui Seiyaku). The cultivation was continued at 37° C. in 3% CO$_2$ - 97% air for 24 hours. After 24 hours passed, the culture medium was changed to that not containing serum (containing hormone), and test compound dissolved by 50% ethanol was added to the medium at the concentration of $1 \times 10^{-6}$ mol/liter.

The cultivation was continued for 3 days, the medium was changed to that not having serum, and adding 10% MTT ([3-(4,5-Dimethylthiazol-2-yl)-2,5-dipheneyltetrazolium bromide]). In this medium, it was maintained at 37° C. in 3% Co$_3$ - 97 % air for 4 hours. Then, MTT coloring matter introduced in to a cell was extracted by 10% sodium dodecyl sulfate/0.01N HCl, and three days later, the 200 μl of extract was poured in the hall of plate having 96 halls. The absorbance at 595 nm of each the extract was measured by mulch-schan. The obtained values were estimated as percentage wherein value of solvent adding group is set to standard.

The result of the estimate was shown in the table 6.

TABLE 6

| Test compound No. | Absorbance (%) |
|---|---|
| 1 | 193 |
| 3 | 159 |
| 17 | 266 |
| 25 | 150 |
| 26 | 213 |
| 45 | 257 |
| 46 | 259 |
| 47 | 121 |
| 48 | 138 |
| 49 | 123 |
| 50 | 167 |
| 51 | 124 |
| 52 | 420 |
| 53 | 391 |
| 54 | 375 |
| 55 | 230 |
| 56 | 270 |
| 57 | 270 |
| 58 | 155 |
| 59 | 320 |
| 60 | 280 |

PHARMACEUTICAL EXAMPLE 1

| | |
|---|---|
| 3,3'-tertalkyl-2,4'-biphenyldiol | 5 mg |
| Starch | 132 mg |
| Magnesium stealate | 19 mg |
| Lactose | 43 mg |

The tablet of the formula disclosed hereinabove was produced by a normal procedure.

PHARMACEUTICAL EXAMPLE 2

| | |
|---|---|
| 3,3'-diallyl-5-ethyl-5'-fluoro-2,4'-biphenyldiol | 150 mg |
| Avicel (Asahi Kasei's brand name) | 40 g |
| Corn starch | 30 g |
| Magnesium stealate | 2 g |
| Hydroxypropylmethylcellulose | 10 g |
| Polyethylene glychohol 6000 | 3 g |
| Castor oil | 40 g |
| Methanol | 40 g |

The mixture of the compound of this invention, Avisel, corn starch and magnesium stealate were milled togather and tableted by means of R 10 mm punch (for sugar coated tablets). The resulting tablets were carted with a film coating composition of hydroxymethlcellulose, polyethyleneglycole 6000, castor oil, and methanol to give film-coated tablets of the above composition.

What is claimed is:

1. A biphenyl derivative or a salt thereof, represented by the general formula (B):

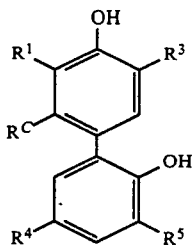
(B)

wherein $R^1$ and $R^5$ are lower alkenyl groups, $R^3$ is a hydroxyl group, a lower alkoxy group, a hydrogen atom, a lower alkyl group which may have a lower alkoxy group or hydroxyl group as a substituent, a lower alkenyl group, a cycloalkenyl group, a phenyl group, a halogen atom, a lower alkanoyl group which may have a halogen atom as a substituent, a thiazolyl group which may have a lower alkyl group as a substituent, group:

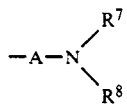

(where A is a lower alkylene group, $R^7$ and $R^8$ are the same or different, a hydrogen atom, lower alkyl group or lower alkanoyl group, these $R^7$ and $R^8$ together with nitrogen atom to which $R^7$ and $R^8$ are bonded may form a saturated or unsaturated heterocyclic 5- or 6-membered ring with or without a nitrogen atom or an oxygen atom, and said ring may have an amide group which may have a lower alkyl group as a substituent or an oxo group), or group:

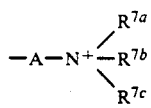

(where $R^{7a}$, $R^{7b}$ and $R^{7c}$ are lower alkyl groups, A is a lower alkylene group), $R^4$ is a hydrogen atom, a lower alkyl group which may have a hydroxyl group or a lower alkoxy group as a substituent, a lower alkoxy group, a phenyl group, a phenyl-lower alkyl group, a phenoxy group, a lower alkenyl group, a lower alkylthio group, a lower alkylsulfinyl group, a lower alkylsulfonyl group, a halogen atom, a lower alkoxy-lower alkyl group or a lower alkanoyl group, $R^c$ is a hydrogen atom or a lower alkyl group.

2. A biphenyl derivative or a salt thereof according to claim 1, wherein $R^3$ is a hydrogen atom, a lower alkyl group which may have a lower alkoxy group or hydroxyl group as a substituent, a lower alkenyl group, a phenyl group or a halogen atom.

3. A biphenyl derivative or a salt thereof according to claim 1, wherein $R^3$ is a hydrogen atom, a lower alkyl group which may have a lower alkoxy group or hydroxyl group as a substituent, a lower alkenyl group, a phenyl group or a halogen atom, $R^c$ is a hydrogen atom or a lower alkyl group, and $R^4$ is a hydrogen atom, a lower alkyl group which may have a lower alkoxy group or hydroxyl group as a substituent, a lower alkenyl group or a lower alkylthio group.

4. A biphenyl derivative or a salt thereof according to claim 1, wherein $R^3$ is a cycloalkenyl group, a lower alkanoyl group which may have a halogen atom as a substituent, a thiazolyl group which may have a lower alkyl group as a substituent, group:

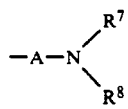

(where A is a lower alkylene group, $R^7$ and $R^8$ are, the same or different, a hydrogen atom, lower alkyl group or lower alkanoyl group, these $R^7$ and $R^8$ together with nitrogen atom to which $R^7$ and $R^8$ are bonded may form a saturated or unsaturated heterocyclic 5- or 6-membered ring with or without a nitrogen atom or an oxygen atom, and said ring may have an amide group which may have a lower alkyl group as a substituent or an oxo group), or group:

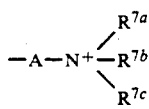

where $R^{7a}$, $R^{7b}$ and $R^{7c}$ are lower alkyl groups, A is a lower alkylene group.

5. A biphenyl derivative or a salt thereof according to claim 2, wherein $R^4$ is a hydrogen atom, a lower alkyl group which may have a hydroxyl group or a lower alkoxy group as a substituent, a lower alkenyl group, or a lower alkylthio group.

6. A biphenyl derivative or a salt thereof according to claim 2, wherein $R^4$ is a lower alkoxy group, a phenyl group, a phenyl-lower alkyl group, a phenoxy group, a lower alkylsulfinyl group, a lower alkylsulfonyl group, a halogen atom, a lower alkoxy-lower alkyl group or a lower alkanoyl group.

7. A biphenyl derivative or a salt thereof according to claim 3, wherein $R^3$ and $R^c$ are hydrogen atom, and $R^4$ is a lower alkyl group.

8. A biphenyl derivative or a salt thereof according to claim 4, wherein $R^4$ is a hdyrogen atom, a lower alkyl group which may have a hydroxyl group or a lower alkoxy group as a substituent, a lower alkenyl group, a lower alkylthio group.

9. A biphenyl derivative or a salt thereof according to claim 4, wherein $R^4$ is a lower alkoxy group, a phenyl group, a phenyl-lower alkyl group, a phenoxy group, a lower alkylsulfinyl group, a lower alkylsulfonyl group, a halogen atom, a lower alkoxy-lower alkyl group or a lower alkanoyl group.

10. A biphenyl derivative or a salt thereof according to claim 5 or 8, wherein $R^1$ and $R^5$ are allyl groups, $R^4$ is a lower alkyl group.

11. A biphenyl derivative or a salt thereof according to claim 6, 7 or 9, wherein $R^1$ and $R^5$ are allyl groups.

12. 3,3'-diallyl-5-ethyl-2,4'-biphenyldiol 13. 3,3'-diallyl-5-ethyl-5'-fluoro-2,4'-biphenyldiol.

14. 3,3'-diallyl-5-methylthio-2,4'-biphenyldiol.

15. 3,3',5,5'-tetraallyl-2,4'-biphenyldiol.

16. 3,3'-diallyl-5-ethyl-5'-phenyl-2,4'-biphenyldiol.

* * * * *